US009482663B2

(12) United States Patent
Jose et al.

(10) Patent No.: US 9,482,663 B2
(45) Date of Patent: Nov. 1, 2016

(54) METHOD FOR BINDING A RECOMBINANT POLYPEPTIDE TO A CARRIER

(75) Inventors: Joachim Jose, Duesseldorf (DE); Jae-Chul Pyun, Seoul (KR)

(73) Assignee: Autodisplay Biotech GmbH, Duesseldorf (DE)

( * ) Notice: Subject to any disclaimer, the term of this patent is extended or adjusted under 35 U.S.C. 154(b) by 399 days.

(21) Appl. No.: 13/395,148

(22) PCT Filed: Sep. 9, 2010

(86) PCT No.: PCT/EP2010/063256
§ 371 (c)(1),
(2), (4) Date: Jun. 26, 2012

(87) PCT Pub. No.: WO2011/029881
PCT Pub. Date: Mar. 17, 2011

(65) Prior Publication Data
US 2012/0264144 A1 Oct. 18, 2012

Related U.S. Application Data

(60) Provisional application No. 61/240,736, filed on Sep. 9, 2009.

(51) Int. Cl.
| | | |
|---|---|---|
| *C12P 19/58* | (2006.01) | |
| *G01N 33/543* | (2006.01) | |
| *C07K 17/06* | (2006.01) | |
| *C07K 17/14* | (2006.01) | |
| *C12N 11/00* | (2006.01) | |
| *C12N 11/14* | (2006.01) | |
| *C12N 15/70* | (2006.01) | |

(52) U.S. Cl.
CPC ......... *G01N 33/54353* (2013.01); *C07K 17/06* (2013.01); *C07K 17/14* (2013.01); *C12N 11/00* (2013.01); *C12N 11/14* (2013.01); *C12N 15/70* (2013.01); *C07K 2319/02* (2013.01); *C07K 2319/03* (2013.01); *C07K 2319/034* (2013.01); *C07K 2319/035* (2013.01); *G01N 2800/102* (2013.01); *G01N 2800/2821* (2013.01); *G01N 2800/302* (2013.01)

(58) Field of Classification Search
CPC .............................. C07K 17/06; C07K 17/14
USPC ........................................................ 435/77
See application file for complete search history.

(56) References Cited

FOREIGN PATENT DOCUMENTS

| WO | 9735022 A1 | 9/1997 |
| WO | 2004088307 A2 | 10/2004 |
| WO | WO 2008111855 A1 * | 9/2008 |

OTHER PUBLICATIONS

Nieba et al., Analytical Biochemistry vol. 252, p. 217-228, 1997.*
Kanno et al., Journal of Biotechnology, vol. 76, p. 207-214, 2000.*
Abdiche et al., Protein Science, vol. 17, p. 1326-1335, 2008.*
Wang et al., Journal of Virology, vol. 79, No. 12, p. 7933-7937, 2005.*
Steffner et al., Biacore Journal, vol. 1, No. 1, p. 10-15, 1997.*
Noel et al., Biacore Journal, vol. 1, No. 1, p. 24-25, 1997.*
Samuelson et al. (Journal of Biotechnology, vol. 96, p. 129-154, 2002).*
Jose et al. (Biosensor and Bioelectronics, vol. 24, p. 1324-1329, 2009).*
Sexton et al. (Sensors and Actuators, vol. A 141, p. 471-475, 2008).*
I. R. Henderson et al: "Type V Protein Secretion Pathway: the Autotransporter Story", Microbiology and Molecular Biology Reviews, vol. 68, No. 4, Dec. 1, 2004, pp. 692-744, XP55002817, ISSN: 1092-2172, DOI: 10.1128/MMBR.68.4.692-744.2004.
Jose J et al: "The autodisplay story, from discovery to biotechnical and biomedical applications", Microbiology and Molecular Biology Reviews, American Society for Microbiology, US, vol. 71, No. 4, Dec. 1, 2007, pp. 600-619, XP002577399, ISSN: 1092-2172, DOI: DOI:10.1128/MBR.00011-07.
Jose J et al: "*Escherichia coli* with autodisplayed Z-domain of protein A for signal amplification of SPR biosensor", Biosensors and Bioelectronics, Elsevier BV, NL, vol. 24, No. 5, Jan. 1, 2009, pp. 1324-1329, XP025868525, ISSN: 0956-5663, DOI: DOI:10.1016/J.BIOS.2008.07.067 [retrieved on Aug. 8, 2008].
Kanno S et al: "Assembling of engineered IgG-binding protein on gold surface for highly oriented antibody immobilization", Journal of Biotechnology 20000121 Elsevier NL, vol. 76, No. 2-3, Jan. 21, 2000, pp. 207-214, XP002651277, DOI: DOI:10.1016/S0168-1656(99)00186-8.
Schultheiss E et al: "Functional esterase surface display by the autotransporter pathway in *Escherichia coli*", Journal of Molecular Catalysis. B, Enzymatic, Elsevier, Amsterdam, NL, vol. 18, No. 1-3, Sep. 13, 2002, pp. 89-97, XP002296796, ISSN: 1381-1177, DOI: D01:10.1016/S1381-1177(02) 00063-2.

* cited by examiner

*Primary Examiner* — Tekchand Saidha
(74) *Attorney, Agent, or Firm* — Rothwell, Figg, Ernst & Manbeck, P.C.

(57) ABSTRACT

The present invention refers to a method for binding a recombinant polypeptide to a carrier, wherein a layer is bound to a carrier, and the layer comprises a recombinant polypeptide on the surface distal to the carrier.

13 Claims, 24 Drawing Sheets

SEQ ID NO: 7

SEQ ID NO: 8

Figure 1:
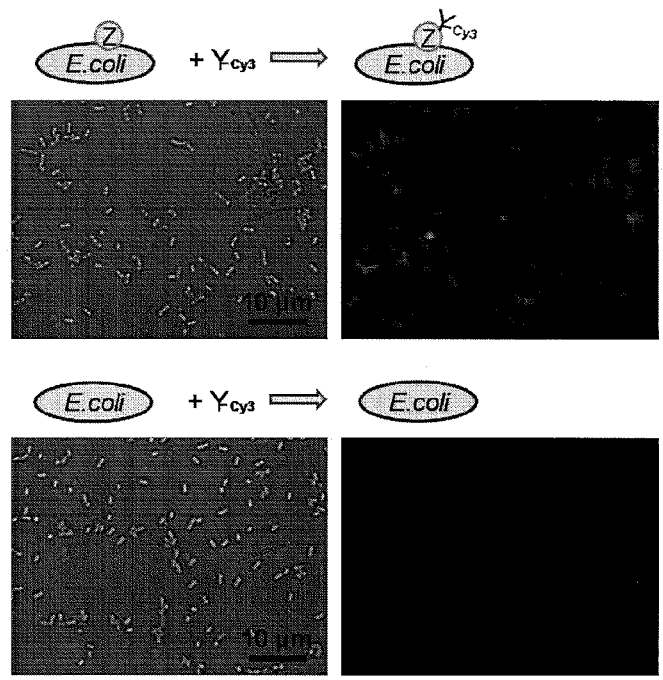

- AFM analysis of OM coated Au surface
  - AFM analysis: non-contact mode (XE-100)
  - Scan area: 100 x 100 μm ⇨ Significant change of surface morphology after OM coating !

SEQUENCE LISTING

```
<160> NUMBER OF SEQ ID NOS: 8

<210> SEQ ID NO 1
<211> LENGTH: 27
<212> TYPE: DNA
<213> ORGANISM: Artificial
<220> FEATURE:
<223> OTHER INFORMATION: forward primer

<400> SEQUENCE: 1
ctcgaggacc cctccaagga ctcgaag                                        27

<210> SEQ ID NO 2
<211> LENGTH: 26
<212> TYPE: DNA
<213> ORGANISM: Artificial
<220> FEATURE:
<223> OTHER INFORMATION: reverse primer

<400> SEQUENCE: 2
ggtaccctgc tgaacggcgt cgagcg                                         26

<210> SEQ ID NO 3
<211> LENGTH: 24
<212> TYPE: DNA
<213> ORGANISM: Artificial
<220> FEATURE:
<223> OTHER INFORMATION: partial sequence pST001
<220> FEATURE:
<221> NAME/KEY: CDS
<222> LOCATION: (1)..(24)
<220> FEATURE:
<221> NAME/KEY: misc_feature
<222> LOCATION: (10)..(15)
<223> OTHER INFORMATION: Xho I site

<400> SEQUENCE: 3 act gat ttg ctc gag gac ccc tcc                                      24
Thr Asp Leu Leu Glu Asp Pro Ser
1               5
```

```
<210> SEQ ID NO 4
<211> LENGTH: 8
<212> TYPE: PRT
<213> ORGANISM: Artificial
<220> FEATURE:
<223> OTHER INFORMATION: Synthetic Construct

<400> SEQUENCE: 4

Thr Asp Leu Leu Glu Asp Pro Ser
1               5

<210> SEQ ID NO 5
<211> LENGTH: 24
<212> TYPE: DNA
<213> ORGANISM: Artificial
<220> FEATURE:
<223> OTHER INFORMATION: partial sequence pST001
<220> FEATURE:
<221> NAME/KEY: CDS
<222> LOCATION: (1)..(24)
<220> FEATURE:
<221> NAME/KEY: misc_feature
<222> LOCATION: (10)..(15)
<223> OTHER INFORMATION: Kpn I site

<400> SEQUENCE: 5 gtt cag cag ggt acc ctt aat cct                                   24
Val Gln Gln Gly Thr Leu Asn Pro
1               5

<210> SEQ ID NO 6
<211> LENGTH: 8
<212> TYPE: PRT
<213> ORGANISM: Artificial
<220> FEATURE:
<223> OTHER INFORMATION: Synthetic Construct

<400> SEQUENCE: 6

Val Gln Gln Gly Thr Leu Asn Pro
1               5

<210> SEQ ID NO 7
<211> LENGTH: 27
<212> TYPE: DNA
<213> ORGANISM: Artificial
<220> FEATURE:
<223> OTHER INFORMATION: partial sequence Z domain
<220> FEATURE:
<221> NAME/KEY: misc_feature
<222> LOCATION: (3)..(8)
<223> OTHER INFORMATION: Xho I site

<400> SEQUENCE: 7
cgctcgagga caacaaattc aacaaag                                     27

<210> SEQ ID NO 8
<211> LENGTH: 23
<212> TYPE: DNA
<213> ORGANISM: Artificial
<220> FEATURE:
<223> OTHER INFORMATION: partial sequence Z domain
<220> FEATURE:
<221> NAME/KEY: misc_feature
<222> LOCATION: (16)..(21)
<223> OTHER INFORMATION: Kpn I site

<400> SEQUENCE: 8
taggtaccta ctttcggcgc ctg                                         23
```

METHOD FOR BINDING A RECOMBINANT POLYPEPTIDE TO A CARRIER

CROSS REFERENCE TO RELATED APPLICATION

This application is a 35 U.S.C. 371 National Phase Entry Application from PCT/EP2010/063256, filed Sep. 9, 2010, which claims the benefit of Provisional Application No. 61/240,736, filed on Sep. 9, 2009, the disclosure of which is incorporated herein by reference.

The present invention refers to a method for binding a recombinant polypeptide to a carrier, wherein a layer is bound to a carrier and comprises a recombinant polypeptide on the surface distal to the carrier. The present invention also refers to a carrier comprising a recombinant polypeptide in a layer, wherein said layer is bound to the carrier and comprises the recombinant polypeptide on the surface distal to the carrier. The present invention also refers to a host cell displaying the recombinant polypeptide on the surface. The present invention also refers to a membrane preparation comprising the recombinant polypeptide.

Immunoassays have been widely used for medical diagnosis, environmental monitoring, forensic tests. Based on the highly specific antigen-antibody interactions, the immunoassays can detect target analytes in complex mixture samples, such as human blood. Conventional immunoassays have exploited solid supports such as microplates, immunosticks, and so on for the immobilization of antibodies (or antigens). For the sensitive detection of a target analyte, the immobilized antibodies should be oriented to expose the binding pockets at $F_{ab}$ regions of each antibody molecule towards target analytes. The portion of such well-oriented antibodies was reported to be less than 20% by physical adsorption of antibodies.

Until recently, various methods have been tried for the orientation control of antibodies in order to improve the sensitivity of immunoassays. Protein A has been most frequently used for the orientation control of antibodies by using the affinity of protein A towards the $F_c$ region of the antibodies (IgG). For immunoassays, protein A was first coated on a microplate, and then the antibodies were immobilized to the microplate with a controlled orientation. The high affinity of avidin or streptavidin toward the biotin molecule was also used for the orientation control of antibodies. For immunoassays, avidin or streptavidin was first coated on a microplate, and then antibodies conjugated with biotin were bound to the avidin or streptavidin on the microplate. As the amino groups used for the biotinylation were known to be located at the Fc region of the antibodies, the biotinylated antibodies could be immobilized with a controlled orientation. In both cases, the sensitivity of each immunoassay was reported to be improved in comparison to the conventional immunoassays by the orientation control effects.

Generally, the immunoaffinity (IA) biosensors utilize the highly selective binding affinity of antibodies for the molecular recognition of a target analyte in a complex mixture such as serum. The antigen binding sites of antibodies (e.g. IgGs) are known to be localized at Fab region, which is a relatively small part compared with the whole antibody structure (Deisenhofer, 1981; Amit et al., 1986; Liddell, 2001). Therefore, the antigen binding sites (Fab region) of antibodies should be exposed to the analyte solution for the analytes to bind effectively to the IA biosensor (Luppa, 2001). Additionally, the antibodies should be immobilized with a high density for the sensitive detection of a target analyte at a very low concentration. These requirements are called 'orientation control' and 'density control' of antibodies, respectively (Chung et al., 2006a, see FIG. 21).

For the orientation control of antibodies, the specific affinity of protein A to the Fc region of antibodies has been exploited for IA biosensors as well as conventional immunoassays (Anderson et al., 1997; Bae et al., 2005; Chung et al., 2006a; Kanno et al., 2000; Lu et al., 1996; Owaku et al., 1995). Protein A originates from *Staphylococcus aureus* and has five domains including the Z-domain with Fc-binding activity (Deisenhofer et al., 1978). The IgG-binding affinity $K_a(rIgG)$ is $4.1 \times 10^8$. Protein A has molecular weight of 42 kDa. However, protein A molecules should also be aligned with a suitable orientation for the orientation control of antibodies on two dimensional transducer surfaces.

Different systems have been applied for the surface display of heterologous proteins in yeast, gram-positive, and gram-negative bacteria. Autodisplay is a very elegant way to express a recombinant protein on the surface of a gram-negative bacterium. Autodisplay is based on the secretion mechanism of the autotransporter family of proteins. These proteins are synthesized as polyprotein precursors that contain structural requirements sufficient for secretion. They cross the inner membrane using a typical signal peptide at the very N-terminus. Arrived in the periplasm, the C-terminal part of the precursor folds into the outer membrane as a porin-like structure, a so-called β-barrel. Through this pore, the N-terminal attached passenger domain is translocated to the surface. There, it might be cleaved off—either autoproteolytically or by an additional protease—or remains anchored to the cell envelope by the transporter domain. Replacing the natural passenger by a recombinant protein results in its proper surface translocation. For this purpose an artificial precursor must be constructed by genetic engineering, consisting of a signal peptide, the recombinant passenger, the β-barrel and a linking region in between, which is needed to achieve full surface access. The AIDA-I autotransporter was successfully used in this way for efficient surface display of various passenger domains (Henderson et al., 2004).

In particular, the autodisplay technology is an expression method for predetermined proteins on the surface of the outer membrane of *E. coli* and other Gram-negative bacteria. The recombinant passenger protein can be transported simply by introducing its coding sequence in-frame between the signal peptide and the translocating domain of the autodisplaying vector. The signal peptide can be obtained from the cholera toxin-subunit (CTB) and may be combined with an artificial promoter. Therefore, the passenger protein, intended for the translocation across the outer membrane, is expressed as a recombinant-fusion protein with another protein called autotransporter at the outer membrane of *E. coli* (AIDA-I) (Jose, 2006). The C-terminal part of the auto-transporter proteins forms a porin-like structure (β-barrel) within the outer membrane of *E. coli*. By the aid of this pore, the recombinant passenger protein is translocated to the surface of the outer membrane of *E. coli* (Jose, 1995, 2006, 2007).

There is a need for better controlling the orientation of recombinantly expressed polypeptides when attaching them to a carrier, so that a large proportion of the polypeptide exposes a desired portion which may be specifically accessed by binding molecules. A method is required to increase the proportion of well-oriented polypeptides bound to the surface of a carrier. Furthermore, a high density of the recombinantly expressed polypeptides on the surface should be achieved. By improvement of orientation, sensitivity of sensors for analyte detection could be improved.

A first aspect of the present invention is a method for binding a recombinant polypeptide to a carrier, wherein a layer is bound to a carrier, and the layer comprises a recombinant polypeptide on the surface distal to the carrier, said method comprising the steps:
(a) providing a host cell transformed with a nucleic acid fusion operatively linked with an expression control sequence, said nucleic acid fusion comprising:
  (i) a portion encoding a signal peptide,
  (ii) a portion encoding the recombinant polypeptide to be displayed,
  (iii) a portion encoding a transmembrane linker, and
  (iv) a portion encoding the transporter domain of an autotransporter,
(b) culturing the host cell under conditions wherein the nucleic acid fusion is expressed and the expression product comprising the recombinant polypeptide is displayed on the surface of the host cell, and
(c) preparing membrane particles from the host cell of (b),
(d) contacting the membrane particles prepared in step (c) with a surface of a carrier so that the membrane particles form a layer bound to the surface, wherein the recombinant polypeptide is located on the surface distal to the carrier.

Another aspect of the present invention is a method for producing a carrier, wherein a layer is bound to a carrier, and the layer comprises a recombinant polypeptide on the surface distal to the carrier, said method comprising the steps:
(a) providing a host cell transformed with a nucleic acid fusion operatively linked with an expression control sequence, said nucleic acid fusion comprising:
  (i) a portion encoding a signal peptide,
  (ii) a portion encoding the recombinant polypeptide to be displayed,
  (iii) a portion encoding a transmembrane linker, and
  (iv) a portion encoding the transporter domain of an autotransporter,
(b) culturing the host cell under conditions wherein the nucleic acid fusion is expressed and the expression product comprising the recombinant polypeptide is displayed on the surface of the host cell, and
(c) preparing membrane particles from the host cell of (b),
(d) contacting the membrane particles prepared in step (c) with a surface of a carrier so that the membrane particles form a layer bound to the surface, wherein the recombinant polypeptide is located on the surface distal to the carrier.

The methods of the present invention provide carriers with an improved limit of detection by improvement of orientation and density of the recombinant polypeptide to be attached to the carrier. The sensitivity may be increased by a factor of at least 10 compared with a carrier comprising the recombinant polypeptide randomly oriented on the surface.

The recombinant polypeptide to be displayed may also be termed "passenger", "passenger polypeptide" or "passenger protein".

"Distal surface" of the membrane preparation indicates the surface which is exposed to the surrounding medium, in contrast to that part of the membrane preparation which is in contact with the carrier.

Step (a) of the methods of the present invention refers to the provision of a host cell. The host cell used in the method of the present invention is preferably a bacterium, more preferably a gram-negative bacterium, particularly an enterobacterium such as *E. coli*.

According to the present invention, a host cell, particularly a host bacterium is provided which is transformed with a nucleic acid fusion operatively linked with an expression control sequence, i.e. a promoter, and optionally further sequences required for gene expression in the respective host cell. The skilled person knows suitable promoters and expression control sequences. The promoter or/and the expression control sequence may be homologous or heterologous to the host cell. Preferably, the nucleic acid fusion is located on a recombinant vector, e.g. a plasmid vector. The host cell may be transformed with at least one nucleic acid fusion, for instance two, three, four, five or even more nucleic acid fusions. If two or more nucleic acid fusions are transformed into a host cell, the nucleic acid fusions preferably encode different recombinant polypeptides as described herein. If a host cell transformed with several nucleic acid fusions is used, these nucleic acid fusions may be located on a single vector or on a plurality of vectors.

At least one host cell as described herein, for instance two, three, four, five, six or even more host cells as described herein may be provided in the methods of the present invention. Each of these host cells is transformed with one nucleic acid fusion or at least one nucleic acid fusion, as described herein. Preferably, the nucleic acid fusions transformed in the at least one host cell encode different recombinant polypeptides as described herein.

The different recombinant polypeptides which may be provided in one or at least one host cell may form a functional unit, for instance the subunits of a functional unit, such as the subunits of an enzyme or the subunits or/and components of an enzyme complex.

The nucleic acid fusion comprises (i) a portion encoding a signal peptide, preferably a portion coding for a gram-negative signal peptide allowing for transport into the periplasm through the inner cell membrane. The signal peptide may be a signal peptide homologous to the host cell. The signal peptide may also be a signal peptide heterologous to the host cell.

Further, the nucleic acid fusion comprises (ii) a portion encoding the recombinant polypeptide to be displayed.

Furthermore, the nucleic acid fusion comprises (iii) a portion encoding a transmembrane linker which is required for the presentation of the passenger polypeptide (ii) on the outer surface of the outer membrane of the host cell. A transmembrane linker domain may be used which is homologous with regard to the autotransporter, i.e. the transmembrane linker domain is encoded by a nucleic acid portion directly 5' to the autotransporter domain. Also a transmembrane linker domain may be used which is heterologous with regard to the autotransporter. The length of the transmembrane linker is preferably 30-160 amino acids.

Further, the nucleic acid fusion comprises (iv) a transporter domain of an autotransporter. In the context of the present invention, autodisplay may be the recombinant surface display of proteins or polypeptides by means of an autotransporter in any Gram-negative bacterium. The transporter domain of the autotransporter according to the invention can be any transporter domain of an autotransporter and is preferably capable of forming a β-barrel structure. A detailed description of the β-barrel structure and preferred examples of β-barrel autotransporters are disclosed in WO97/35022 incorporated herein by reference. Henderson et al. (2004) describes autotransporter proteins which comprise suitable autotransporter domains (for summary, see Table 1 of Henderson et al., 2004). The disclosure of Henderson et al. (2004) is included herein by reference. For example, the transporter domain of the autotransporter may be selected from Ssp (P09489, *S. marcescens*), Ssp-h1 (BAA33455, *S. marcescens*), Ssp-h2 (BAA11383, *S. marcescens*), PspA (BAA36466, *P. fluorescens*), PspB (BAA36467, *P. fluorescens*), Ssa1 (AAA80490, *P. haemolytica*), SphB1 (CAC44081, *B. pertussis*), AspA/NalP (AAN71715, *N. meningitidis*), VacA (Q48247, *H. pylori*), AIDA-I (Q03155, *E. coli*), IcsA (AAA26547, *S. flexneri*), MisL (AAD16954, *S. enterica*), TibA (AAD41751, *E. coli*), Ag43 (P39180, *E. coli*), ShdA (AAD25110, *S. enterica*), AutA (CAB89117, *N. meningitidis*), Tsh (I54632, *E. coli*), SepA (CAC05786, *S. flexneri*), EspC (AAC44731, *E. coli*), EspP (CAA66144, *E. coli*), Pet (AAC26634, *E. coli*), Pic (AAD23953, *E. coli*), SigA (AAF67320, *S. flexneri*), Sat (AAG30168, *E. coli*), Vat (AAO21903, *E. coli*), EpeA (AAL18821, *E. coli*), EatA (AAO17297, *E. coli*), EspI (CAC39286, *E. coli*), EaaA (AAF63237, *E. coli*), EaaC (AAF63038, *E. coli*), Pertactin (P14283, *B. pertussis*), BrkA (AAA51646, *B. pertussis*), Tef (AAQ82668, *B. pertussis*), Vag8 (AAC31247, *B. pertussis*), PmpD (O84818, *C. trachomatis*), Pmp20 (Q9Z812, *C. pneumoniae*), Pmp21 (Q9Z6U5, *C. pneumoniae*), IgA1 protease (NP_283693, *N. meningitidis*), App (CAC14670, *N. meningitidis*), IgA1 protease (P45386, *H. influenzae*), Hap (P45387, *H. influenzae*), rOmpA (P15921, *R. rickettsii*), rOmpB (Q53047, *R. rickettsii*), ApeE (AAC38796, *S. enterica*), EstA (AAB61674, *P. aeruginosa*), Lip-1 (P40601, *X. luminescens*), McaP (AAP97134, *M. catarrhalis*), BabA (AAC38081, *H. pylori*), SabA (AAD06240, *H. pylori*), AlpA (CAB05386, *H. pylori*), Aae (AAP21063, *A. actinomycetemcomitans*), NanB (AAG35309, *P. haemolytica*), and variants of these autotransporters. Given in brackets for each of the exemplary autotransporter proteins are examples of suitable genbank accession numbers and species from which the autotransporter may be obtained. Preferably the transporter domain of the autotransporter is the *E. coli* AIDA-I protein or a variant thereof, such as e.g. described by Niewert U., Frey A., Voss T., Le Bouguen C., Baljer G., Franke S., Schmidt M A. The AIDA Autotransporter System is Associated with F18 and Stx2e in *Escherichia coli* Isolates from Pigs Diagnosed with Edema Disease and Postweaning Diarrhea. Clin. Diagn. Lab. Immunol. 2001 Jan, 8(1):143-149;9.

Variants of the above indicated autotransporter sequences can e.g. be obtained by altering the amino acid sequence in the loop structures of the β-barrel not participating in the transmembrane portions. Optionally, the nucleic acid portions coding for the surface loops can be deleted completely. Also within the amphipathic β-sheet conserved amino exchanges, i.e. the exchange of an hydrophilic by another hydrophilic amino acid or/and the exchange of a hydrophobic by another hydrophobic amino acid may take place. Preferably, a variant has a sequence identity of at least 70%, at least 90%, at least 95% or at least 98% on the amino acid level to the respective native sequence of the autotransporter domain, in particular in the range of the β-sheets.

Step (b) of the methods of the present invention refers to culturing the host cell under conditions wherein the nucleic acid fusion is expressed and the expression product comprising the recombinant polypeptide is displayed on the surface of the host cell. The person skilled in the art knows suitable culture conditions. The method according to the invention allows for an efficient expression of passenger proteins on the surface of host cells, particularly *E. coli* or other gram-negative bacterial cells up to 100 000 or more molecules per cell by using a liquid medium of the following composition: 5 g/l to 20 g/l, preferably about 10 g/l trypton, 2 g/l to 10 g/l, preferably about 5 g/l yeast extract, 5 g/l to 20 g/l, in particular about 10 g/l NaCl and the remaining part water. The medium should possibly contain as little as possible divalent cations, thus preferably Aqua bidest or highly purified water, e.g. Millipore water is used. The liquid medium may contain in addition preferably EDTA in a concentration of 2 µM to 20 µM, in particular 10 µM. Moreover, it contains preferably reducing reagents, such as 2-mercapto ethanol or dithioreitol or dithioerythritol in a preferred concentration of 2 mM to 20 mM. The reducing reagents favour a non-folded structure of the polypeptide during transport. The liquid medium can further contain additional C-sources, preferably glucose, e.g. in an amount of up to 10 g/l, in order to favour secretion i.e. transfer of the passenger to the surrounding medium. For surface display preferably no additional C-source is added. Preferred culture conditions for Gram-negative cells, such as *E. coli*, are described in the Examples.

The components (i) to (iv) in the nucleic acid fusion of the present invention are preferably oriented from 5' to 3'. In the expression product obtained in step (b), the amino acid sequences encoded by nucleic acid sequences (i) to (iv) are preferably arranged N terminal to C terminal.

Step (c) of the methods of the present invention refers to preparing membrane particles. The membrane particles may be membrane vesicles. Preferred membrane particles are outer membrane particles. In particular step (c) refers to preparing outer membrane particles of cells displaying a recombinant polypeptide on the surface, e.g. of Gram-negative bacterial cells. The person skilled in the art knows suitable conditions (e.g. Hantke, 1981, Schultheiss et al., 2002). Typical conditions for preparing membrane particles are employed in the examples of the present invention. Outer membrane particles from a host cell as described herein may be performed by a method comprising the steps:

(a) treating the host cell with a hydrolase (such as lysozyme) and optionally with a DNAse. This enzymatic treatment may be performed at room temperature. The hydrolase hydrolyses the cell wall within the periplasmatic space. The cell wall comprises peptidoglycans to be hydrolyzed.

(b) optionally solubilizing the preparation of (a) with a tenside, such as Triton X-100, or/and with sarcosine, followed by optional centrifugation of cell debris. The thus obtained preparation of outer membrane particles may be centrifuged, washed and resuspended.

In a host cell being a Gram-negative bacterium, such as *E. coli*, after translocation, the recombinant passenger remains attached to the surface of the outer membrane by the β-barrel, which is serving as an anchor within the outer membrane. Due to the controlled integration of the β-barrel within the outer membrane, the C terminal part of the β-barrel is directed to the inner side of the outer membrane, whereas the N-terminal part of the linker, to which the recombinant passenger protein is covalently bound, is directed to the outer surface of the outer membrane, i.e. the environment. The recombinant passenger protein has an oriented location after transport, namely it is directed to the cellular surface. The recombinant passenger protein has the identical orientation as the lipopolysaccharide (LPS) layer which may be present in the outer membrane.

In the present invention, membrane particles, in particular outer membrane particles are prepared and used for the orientation controlled coating of carriers with recombinant proteins. Membrane particles of the present invention prepared from the host cell of the present invention comprise the recombinant peptide at the surface directed to the environment. In contrast to the inner membrane which is a unit membrane, the outer membrane of Gram-negative bacteria, in particular *E. coli*, is asymmetric. The outer membrane may comprise an inner layer comprising phospholipids and an outer layer comprising LPS. LPS is hydrophilic and may contain several negative charges. By using outer membrane particles with anchored passenger proteins by a β-barrel for the coating of carriers, the outer side of the outer membrane, in particular the LPS side will be directed to the surface distal to the carrier. As a consequence the recombinant protein or a domain thereof, which are integrated in the outer membrane by autodisplay, will be directed to the surface distal to the carrier as well. The core part of the membrane particles may stabilize the interaction of the outer membrane layer obtained by applying outer membrane particles to the carrier by hydrophobic interactions and may contain lipoproteins or peptidoglycans.

Step (d) of the methods of the present invention refers to contacting the membrane particles with a surface of a carrier so that the membrane particles form a layer bound to the surface, wherein the recombinant polypeptide is located on the surface distal to the carrier. Contacting the membrane particles with the surface may performed in a hydrophilic medium, such as an aqueous medium, for instance a buffer such as PBS.

When the membrane particles with a hydrophilic surface are contacted with a surface, in particular a hydrophobic surface, the particles form an ordered layer through the hydrophobic interactions. In the method of the present invention, membrane preparations comprising a recombinantly expressed polypeptide are used. As described herein, the membrane particles may comprise hydrophilic LPS and the recombinant protein located at the surface. When the membrane particles form a layer on the surface of the carrier, hydrophobic interactions may induce a contact between the surface and the core portion of the membrane particles. That portion of the membrane particles comprising the recombinant polypeptide and the LPS is oriented to the surrounding medium, which may be a hydrophilic medium. Thus, formation of a layer on the surface of the carrier leads to recombinant polypeptides located at the distal surface with respect to the carrier.

A layer bound to the surface may be formed by contacting the surface with a liquid comprising membrane particles of the present invention, in particular outer membrane particles, as described herein. The membrane particles preferably form a suspension. The liquid comprising the membrane particles may be prepared at a protein concentration in the range of 50 to 500 μg/ml, wherein the protein is the protein contained in the membrane particles. Preferred is a concentration of about 100 μg/ml or about 300 μg/ml protein. The liquid may be prepared in a buffer, for instance PBS.

The membrane particles of the present invention may comprise a hydrophilic surface. The hydrophilic surface of the membrane particles may be caused by negative charges on the surface, for instance by the LPS layer at the surface of the host cell, such as an *E. coli* cell. Bacterial cells, in particular Gram-negative bacterial cells, may contain a lipopolysaccharide layer on the surface. The negative surface charge of the host cell used for preparing the membrane particles and displaying the recombinant polypeptide, for instance an *E. coli* cell, may be in the range of −20 mV to −30 mV, −21 mV to −26 mV, or −22 to −25 mV in terms of the zeta potential.

The diameter of the membrane particles may be in the range of 1 nm to 1000 nm, in the range of 50 nm to 500 nm, in the range of 75 to 200 nm, or in the range of 90 to 120 nm. At least 80%, at least 90%, at least 95%, or at least 98% of the membrane particles may have a diameter in a range selected from the ranges described herein.

In the method of the present invention, the surface of the carrier is a hydrophobic surface. Hydrophilic surfaces may have a contact angle below 30°. Hydrophobic surfaces may have a contact angle of more than 90°. A increasing surface angle of more than 30° indicates a gradually increasing hydrophobicity of a surface. In the context of the present invention, a hydrophobic surface may have a contact angle of at least 40°. The surface preferably has a hydrophobicity described by a contact angle of at least 40°, at least 50°, at least 60°, at least 65°, at least 70°. Contact angles are preferably determined by the sessile drop method. The sessile drop method is a standard method for determining contact angles. Measurements may be performed with a contact angle goniometer. Preferred contact angles of the hydrophobic surface are in a range of 40° to 100°, 50° to 90°, or 60° to 80°.

The surface employed in the method of the present invention may be a metal surface. A suitable metal surface has a contact angle e.g. in the range of 50° to 80°. A suitable metal may be selected from gold, silver, titanium, aluminium and alloys such as brass. A preferred surface is a gold surface. The gold surface may be employed as it is. An untreated gold surface has a hydrophobicity suitable for the method of the present invention. A treatment of the gold surface with thiolated hydrocarbons or hydrocarbons with functional groups such as carboxylic acids or hydroxyl groups is not required.

Another preferred surface comprises a polymer, for instance a surface usually employed in disposable materials for use in biochemical or/and medical science. The polymer may be an artificial polymer. Examples of artificial polymers include a polymer selected from polystyrenes, polypropylenes, and polycarbonates. The polystyrene may be produced from [2,2]paracyclophane monomers. Polystyrene surfaces may be treated with oxygene plasma introducing OH or/and methylene groups in order to modify the hydrophobicity. Examples of such modified surfaces include Maxi-sorp, Medi-sorp, Multi-sorp, and Poly-sorp surfaces. Another suitable polystyrene surface is Parylene N produced from [2,2]paracyclophane monomers. Yet another suitable surface is Parylene A [Poly(monoamino-p-xylene)]. Especially suitable are surfaces comprising a polymer having a hydrophobicity described by a contact angle of at least 50°. Suitable surfaces are selected from polystyrene, Parylene A, Parylene N, Maxi-sorp, Medi-sorp, Multi-sorp, and Poly-sorp. Preferred surfaces are selected from polystyrene, Parylene A, Parylene N, Maxi-sorp, Medi-sorp, and Poly-sorp.

The surface may comprise a natural polymer. Suitable natural polymers include polybutyrate and cellulose and derivatives thereof.

A further surface is provided by latex particles, in particular latex beads.

Yet another surface is provided by C18-modified particles, in particular C18-modified monolithic silica particles. C18 refers to an alkyl group comprising 18 carbon atoms. C18-modified particles are known in the art.

Yet another suitable surface is a glass surface.

The surface may be modified is order to adjust the hydrophobicity. Modification may be performed by chemical treatment (i.e. by oxygen plasma), physical treatment (e.g. by laser irradiation or/and radioactive irradiation), or by mechanical treatment.

In the method of the present invention, any polypeptide capable of being surface displayed may be employed. The length of the recombinant polypeptide to be displayed, i.e.

the passenger polypeptide, may be in the range of from 5-3000 amino acids, in the range from 10-1500 amino acids, in the range of 20 to 1000 amino acids or in the range of 50 to 500 amino acids.

The recombinant polypeptide of the present invention may be a polypeptide capable of specifically binding a molecule. Such molecule may be an analyte molecule in a sample, or may be a binding molecule. In the context of the present invention, "binding molecule" may be any molecule capable of binding a molecule, either by convalent or non-covalent binding. Binding may be specific or non-specific binding. Examples of binding molecules employed in the present invention are antibodies, streptavidin, avidin, protein A, protein M and protein G. The binding molecule may also be any molecule, as described herein, which is capable of specifically binding a recombinant polypeptide of the present invention, wherein the recombinant polypeptide may be selected from antibodies, fragments and variants thereof, protein A, fragments and variants thereof, streptavidin, fragments and variants thereof, avidin, fragments and variants thereof, M proteins from Streptococci, fragments and variants thereof, protein G, fragments and variants thereof. An example of polypeptides binding the A protein are IgG antibodies. The antibody may for instance be an anti-CRP antibody or an anti-S100B antibody. The binding molecule may also be biotin, optionally coupled to a third molecule, which third molecule may be a detectable label.

The skilled person knows detectable labels. A detectable label, as used herein, may include luminescent label, such as fluorescein and derivatives thereof.

Example 4 describes the use of streptavidin in the production of a carrier (biosensor) of the present invention by the method of the present invention.

Specific embodiments of the present invention refer to combinations of the recombinant polypeptide and binding molecules as follows: The recombinant polypeptide may be protein A or the Z domain thereof, as described herein, and the binding molecule may be an IgG antibody, such as an anti-CRP antibody or an anti-S100B antibody. The recombinant polypeptide may be streptavidin or avidin, and the binding molecule may be biotin, which biotin may be coupled to a third molecule, which third molecule may be a detectable label.

The recombinant polypeptide employed in the method of the present invention may be a protein capable of specifically binding the $F_c$ region of an antibody, for instance an IgG antibody. An example is the A protein from *Staphylococcus aureus* or a fragment or variant thereof capable of binding an $F_c$ domain. The Z domain is an example of such fragment. Another example of an $F_c$ binding protein is the M protein from *Streptococcus*, or a fragment and variant thereof. The variants and fragments of the A protein and the M protein are capable of specifically binding the $F_c$ domain. Another example of a protein capable of binding IgG is the protein G from *Streptococcus*, or a fragment and variant thereof, wherein fragments and variants are capable of binding IgG.

The recombinant polypeptide employed in the method the present invention may be a molecule capable of specifically binding biotin. Examples of such polypeptides are avidin, streptavidin and variants and fragments thereof, wherein the variant and fragments are capable of specifically binding biotin.

The recombinant polypeptide employed in the method of the present invention may be an antibody, in particular an IgG antibody, or a fragment or variant thereof, wherein the fragment or variant has the antigen binding properties of the antibody. A suitable fragment comprises the $F_{ab}$ region. The person skilled in the art knows suitable methods for the preparation of a nucleic acid encoding an antibody which is capable of specifically binding a predetermined target structure. Different nucleic acids may be prepared encoding the heavy chain, the light chain, or/and a fragment or variant thereof. Said nucleic acid may form part of the nucleic acid fusion as described in step (a), item (ii) in the methods of the present invention, wherein the heavy chain, the light chain, fragments or/and variants thereof may be encoded by separate nucleic acid fusions. The chains of the antibody may be coupled to the autotransporter domain so that display of the fusion protein of the present invention comprising the antibody sequence exposes the antigen binding sites ($F_{ab}$ region) to the surrounding medium, and the $F_c$ region, if present, is located close to the membrane layer.

For display of the antibody on the host cell, the host cell may comprise a first nucleic acid fusion and a second nucleic acid fusion, wherein the first nucleic acid fusion comprises a sequence encoding the heavy chain or a variant or fragment thereof, and the second nucleic acid comprises a sequence encoding the light chain or a variant of fragment thereof, wherein the variants and fragments have the antigen binding properties of the antibody. The nucleic acid fusions may be provided in different host cells.

The antibody as described in the various embodiments and aspects of the present invention may be a human antibody, an antibody from rabbit, horse, or goat, or may be obtained from any species the antibodies of which are known to be employed in immunoassays or/and diagnostic methods.

Preferably, a variant has a sequence identity of at least 70%, at least 90%, at least 95% or at least 98% on the amino acid level to the respective native sequence. In an antibody variant, the degree of identity may refer to the framework region or/and the complementary determining region. In case of different complementary determining regions, the degree of identity may refer to the framework region.

Preferably, a fragment has a length of at least 70%, at least 90%, at least 95% or at least 98% on the amino acid level to the respective native sequence.

The recombinant polypeptide may be protein A, a fragment or variant thereof, streptavidin, a fragment or variant thereof, avidin, a fragment or variant thereof, an M protein from Streptococci, a fragment or variant thereof, protein G, a fragment or variant thereof.

The recombinant polypeptide may be an antibody, an antibody fragment e.g. a scFv fragment, a Fc fragment, a Fab fragment, a monovalent antibody (e.g. from camelids), a bivalent antibody, a nanobody, or any other polypeptide derived directly or indirectly from antibodies with human, mouse, rat, goat, sheep or any other animal origin. The antibody may be selected from a library by a laboratory evolution approach (directed evolution approach) or may be constructed by rational design.

The recombinant polypeptide may be a receptor, of prokaryotic or eukaryotic origin, e.g. eukaryotic cellular surface receptor, nuclear receptor, hormone receptor, G-protein coupled receptor, receptor of the receptor-tyrosine kinase type, MHC-molecule or a domain derived thereof, a T cell receptor or a domain derived thereof, a CD receptor in general or a domain derived therefrom.

The recombinant polypeptide may be a ligand of prokaryotic or eukaryotic origin, or maybe of artifical origin, i.e. may be selected from a library or designed by a rational approach.

The recombinant polypeptide may be an enzyme, monomoeric, dimeric, oligomeric, homodimeric, heterodimeric, homooligomeric, heterooligomeric of eyucaryotic or prokaryotic origin.

It is preferred that the polypeptide comprises a sequence capable of specifically binding an analyte molecule in a sample, or/and to a binding molecule, such as a second polypeptide, which may be an antibody. The binding sequence of the recombinant polypeptide of the present invention may be a partial sequence of the recombinant polypeptide. The binding sequence may be an epitope. The binding sequence may have a length of 5 to 10 amino acids, 5 to 15, or 5 to 20 amino acids. The binding sequence may be located in the N terminal domain of the recombinant polypeptide. As described herein, the autotransporter domain may form a β-barrel structure which upon expression in a host cell is anchored in the outer membrane of the host cell. The autotransporter domain may be fused to the C-terminal portion of the recombinant polypeptide by the linker. In this case, the C terminus of the recombinant polypeptide is located proximal to the membrane layer, and the N terminus is located distally. Location of the binding sequence in the distal portion of the recombinant polypeptide ensures best exposure of the sequence to the surrounding medium. In the context of the present invention, "proximal sequence" indicates those sequences of the bound recombinant polypeptide located close to the membrane layer on the carrier. "Distal sequence" indicates those sequences which are distant to the membrane layer on the carrier.

The method of the present invention may further comprise binding a binding molecule, as described herein, to the carrier, wherein the binding molecule specifically binds to the recombinant polypeptide.

Yet another aspect of the present invention is a carrier comprising a recombinant polypeptide in a layer, wherein said layer is bound to the carrier. Said layer comprises the recombinant polypeptide on the surface distal to the carrier, and said layer comprises membrane components of a host cell expressing the recombinant polypeptide. The carrier is preferably a biosensor. The carrier may be suitable for immunoassays, such as ELISA immunoassays.

The carrier may comprise a metal surface, in particular a gold surface. Such a carrier may be an SPR (surface plasmon resonance) biosensor or a capacitive biosensor. The carrier may also comprise a polymeric surface, wherein said surface comprise artificial or/and natural polymers. The carrier may also comprise a glass surface, wherein said surfaces contact to layer. Suitable surfaces including metal surfaces, polymeric surfaces and glass surfaces are described herein in the context of the methods of the present invention. The carrier may be provided in the form of beads, or may be provided in the form of a material suitable for chromatographic separation, for instance in a column. For example, magnetic beads may be used as carriers.

The carrier of the present invention may be produced by the methods of the present invention, as described herein. The methods of the present invention result in a carrier wherein the recombinant polypeptides are exposed to the surrounding medium. In particular, a predetermined sequence is exposed to the surrounding medium. This goal is attained by contacting the surface of the carrier with a membrane particle comprising a fusion polypeptide. The fusion polypeptide comprises an autotransporter domain anchored in the membrane and a passenger polypeptide (recombinant polypeptide) which is exposed to the surrounding medium. By this procedure, essentially all recombinant polypeptides expose a particular sequence to the surrounding medium. This particular sequence can be a predetermined sequence. The autotransporter domain may be located in the C terminal region of the fusion polypeptide, and the recombinant polypeptide may be located in the N terminal region. In this case, essentially all molecules expose the N-terminal region of the fusion polypeptide to the surrounding medium. Contacting the carrier with the membrane particles is described herein in the context of the methods of the present invention.

"Biosensor" in the context of the present invention refers to a carrier comprising a recombinant polypeptide, wherein the recombinant polypeptide is capable of specifically binding an analyte in a sample, or may be capable of specifically binding a binding molecule, as described herein. In particular, said binding molecule is capable of binding an analyte. Binding of the binding molecule may be directly, or indirectly via at least one further molecule, for instance a linker molecule. The analyte may be contained in a sample. The analyte bound to the carrier can be detected or/and determined by a further antibody specific for the analyte, wherein the further antibody may comprise a label. Suitable labeled antibodies are known. The analyte may also be detected by surface plasmon resonance or/and capacitance measurement. Suitable techniques include cyclic voltammetry (CV) and impedance spectroscopy analysis.

The biosensor of the present invention may be an SPR biosensor. The biosensor may also be a capacitive biosensor, in particular suitable for cyclic voltammetry (CV) or/and impedance spectroscopy analysis.

The carrier may comprise a molecular recognition layer which is the surface bound layer comprising membrane components. "Molecular recognition layer" indicates that molecules, such as binding molecules or/and analytes, may specifically recognize a predetermined portion of the recombinant polypeptide.

The recombinant polypeptide on the carrier may be selected from recombinant polypeptides employed in the method for binding a recombinant polypeptide to a carrier, as described herein, or/and the method for producing a carrier, as described herein. The recombinant polypeptide on the carrier may be selected from antibodies, fragments and variants thereof, protein A, fragments and variants thereof, streptavidin, fragments and variants thereof, avidin, fragments and variants thereof, M proteins from Streptococci, fragments and variants thereof, protein G, fragments and variants thereof. The recombinant polypeptide on the carrier may also be selected from receptors, ligands, and enzymes.

Furthermore, the carrier may further comprise a binding molecule, as described herein, specifically bound to the recombinant polypeptide. The binding molecule may be any molecule, as described herein, which is capable of specifically binding a recombinant polypeptide of the present invention, wherein the recombinant polypeptide may be selected from antibodies, fragments and variants thereof, protein A, fragments and variants thereof, streptavidin, fragments and variants thereof, avidin, fragments and variants thereof, M proteins from Streptococci, fragments and variants thereof, protein G, fragments and variants thereof. An example of polypeptides binding the A protein are IgG antibodies. The antibody may for instance be an anti-CRP antibody or an anti-S100B antibody. The binding molecule may also be biotin, optionally coupled to a third molecule, which third molecule may be a detectable label.

Specific embodiments of the present invention refer to carriers comprising combinations of recombinant polypeptide and binding molecules as follows: The recombinant polypeptide may be protein A or the Z domain thereof, as described herein, and the binding molecule may be an IgG antibody, such as an anti-CRP antibody or an anti-S100B antibody. The recombinant polypeptide may be streptavidin or avidin, and the binding molecule may be biotin, which biotin may be coupled to a third molecule, which third molecule may be a detectable label.

The carrier as described herein may be employed in a method for determining an analyte, or/and for detecting an analyte in a sample. The analyte may be a molecule in a sample, for instance a biological sample obtained from a patient. Examples of methods for determining an analyte include immunoassays, such as ELISA, capacitance measurement, as described herein, and surface plasmon resonance, as described herein. The method for determination an analyte may be a diagnostic method.

A carrier of the present invention produced by the method of the present invention is described in the Example 1, 2, 3 and 4. Example 1 describes the use of a biosensor of the present invention in analyte detection by an immunoassy. Example 2 describes the use of a biosensor of the present invention in anayte detection by surface plasmon resonance measurement. Example 3 describes the use of a biosensor of the present invention in anayte detection by capacitance measurement. Example 4 describes the use of streptavidin in the production of a biosensor.

The carrier of the present invention may achieve a higher electric isolation than conventional SAM carriers. The total charge transfer of carriers of the present invention may be at least 10 mC, or at least 20 mC. The charge transfer resistance of a carrier of the present invention may be at least 220 mOhm/mm$^2$, at least 250 mOhm/mm$^2$, at least 300 mOhm/mm$^2$, at least 350 mOhm/mm$^2$, or at least 400 mOhm/mm$^2$.

The carrier of the present invention, in particular a capacitive biosensor of the present invention, may provide an LOD (limit of detection) for an analyte of less than 10 pg/ml, less than 5 pg/ml, less than 4 pg/mg, less than 3 pg/ml, less than 2 pg/ml, less than 1 pg/ml, or about 100 fg/ml, wherein the LOD is determined as the concentration where the response is three times higher than that of the standard deviation from the baseline response by a blank sample.

The carrier of the present invention, in particular a SPR biosensor of the present invention, may provide an LOD (limit of detection) for an analyte of less than 100 ng/ml, less than 10 ng/ml, less than 5 ng/ml, less than 4 ng/mg, less than 3 ng/ml, less than 2 ng/ml, or about 1.5 g/ml, wherein the LOD is determined as the concentration where the response is three times higher than that of the standard deviation from the baseline response by a blank sample.

The analyte may specifically bind to the recombinant polypeptide exposed on the surface of the carrier to the surrounding medium. Examples of suitable carriers include carriers wherein the recombinant polypeptide is an antibody, fragment or variant thereof, as described herein. By orientation control and density control of the antibodies as described in the present invention, the sensitivity of the immunoassays can be increased. The carrier of the present invention exposes the fusion polypeptide comprising the antibody sequence so that essentially all antibody molecules expose the antigen binding site to the surrounding medium, and the analyte can bind to the recombinant polypeptide with minimal sterical hindrance.

The analyte may specifically bind to an analyte binding molecule which is coupled to the recombinant polypeptide exposed on the surface of the carrier to the surrounding medium. Coupling of the analyte binding molecule may be directly, or indirectly via at least one further molecule, for instance a linker molecule or binding molecule, as described herein. The analyte binding molecule can be an antibody. The recombinant polypeptide of the present invention may be a molecule capable of specifically recognizing the analyte binding molecule (for instance the $F_c$ region of the antibody). Suitable recombinant polypeptides include protein A, protein M, protein G or an antibody capable of specifically recognizing the analyte binding molecule. Suitable antibodies include anti-IgG-antibodies. By orientation control and density control of the recombinant polypeptide as described in the present invention, the sensitivity of the immunoassays can be increased. The carrier of the present invention exposes the fusion polypeptide so that essentially all fusion polypeptides expose the binding site to the surrounding medium, which binding site is capable of recognizing the analyte binding molecule. When the analyte binding molecule binds to the recombinant polypeptides, the analyte binding molecule can be oriented so that the analyte binding site of the analyte binding molecule exposes to the surrounding medium so that an analyte can bind with minimal sterical hindrance. A specific example of an immunoassay of the present invention is an immunoassay for determination of C reactive protein, for instance as described in Example 2 or 3.

Yet another aspect of the present invention is a diagnostic method comprising the determination of an analyte with a carrier or/and biosensor of the present invention. The diagnostic method of the present invention may be a method for determination of C reactive protein (CRP), comprising determination of the amount of CRP in a sample from a patient with a carrier or/and biosensor as described herein, wherein the presence of CRP indicates inflammatory diseases, such as rheumatoid arthritis. In particular, an increased level of CRP compared with persons not suffering from an inflammatory disease may indicate the presence of an inflammatory disease. In the method, the sample may be contacted with the carrier or/and biosensor under conditions suitable for binding of the CRP to the carrier. CRP may be detected by an anti-CRP antibody. Suitable antibodies are known. The antibody may be a binding molecule, as described herein. The antibody may be bound to a carrier of the present invention exposing a recombinant polypeptide capable of recognizing the $F_c$ portion of the anti-CRP antibody. Suitable recombinant polypeptides include protein A, fragments and variants thereof, protein M, fragments and variants thereof, protein G, fragments and variants thereof and antibodies capable of recognizing the $F_c$ portion.

Example 5 describes the use of a biosensor of the present invention for detection of CRP in sera obtained from rheumatoid arthritis positive patients and control patients. An improved sensitivity of the biosensor of the present to invention compared to standard ELISA test could be demonstrated.

The diagnostic method of the present invention may also be a method for determination of S100B protein, comprising determination of the amount of S100B in a sample from a patient with a carrier or/and biosensor as described herein, wherein the presence of S100B indicates schizophrenia or/and Alzheimer disease. In particular, an increased level of S100B compared with persons not suffering from schizophrenia or/and Alzheimer disease may indicate schizophrenia or/and Alzheimer disease. In the method, the sample may be contacted with the carrier or/and biosensor under conditions suitable for binding of the S100B protein to the carrier. The sample may be a cerebrospinal fluid sample. S100B may be detected by an anti-S100B antibody. Suitable antibodies are known. The antibody may be a binding molecule, as described herein. The antibody may be bound to a carrier of the present invention exposing a recombinant polypeptide capable of recognizing the $F_c$ portion of the anti-S100B antibody. Suitable recombinant polypeptides include protein A, fragments and variants thereof, protein M, fragments and variants thereof, protein G, fragments and variants thereof and antibodies capable of recognizing the $F_c$ portion.

Example 6 describes the use of a biosensor of the present invention for detection of S100B protein in cerebrospinal fluid of patients.

The carrier of the present invention may be used in a diagnostic method. An example of a diagnostic method is the determination of CRP in a patient sample, wherein the carrier may comprise an anti-CRP antibody. Another example of a diagnostic method is the determination of S100B in a patient sample, wherein the carrier may comprise an anti-S100B antibody. The carrier of the present invention may be used for diagnosis of Alzheimer disease, schizophrenia, or/and an inflammatory disease, as described herein.

Yet another aspect of the present invention is a host cell displaying the recombinant polypeptide on the surface, wherein the recombinant polypeptide is capable of specifically binding a binding molecule or/and an analyte. The host cell may be any host cell as described herein.

Yet another aspect of the present invention is a membrane preparation comprising a recombinant polypeptide, wherein the membrane preparation is suitable of forming a layer on a carrier. The membrane preparation may be obtained from a host cell as described herein, for instance by step (c) of the method of the present invention. The recombinant polypeptide of the may be any recombinant polypeptide as described herein.

Yet another aspect of the present invention is the use of a membrane preparation comprising a recombinant polypeptide in the manufacture of a carrier comprising a recombinant polypeptide. The carrier may be any carrier as described herein.

The invention is further illustrated by the following figures and examples.

FIGURE LEGENDS

FIG. 1. IgG binding activity test of *E. coli* by treatment of Cy3 labeled IgG to (a) *E. coli* with Z-domain on the outer membrane and (b) intact *E. coli* without Z-domain on the surface of outer membrane.

Figure 2:
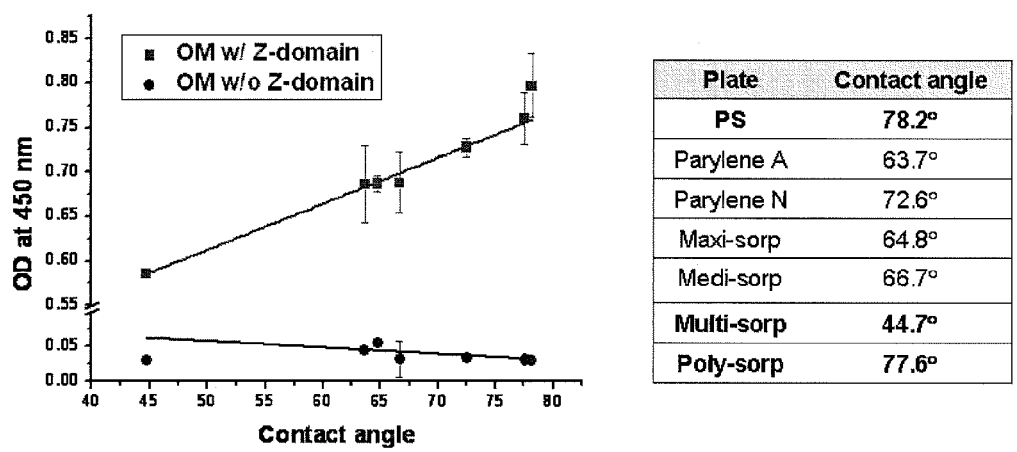

FIG. 2. IgG binding activity of the outer membrane layer formed on various microplate surfaces with controlled hydrophobicity.

Figure 3:
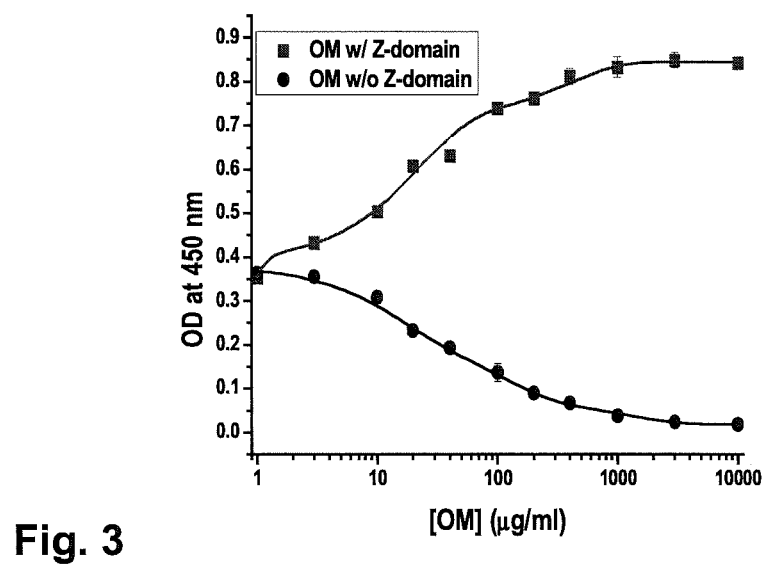
Figure 4A:
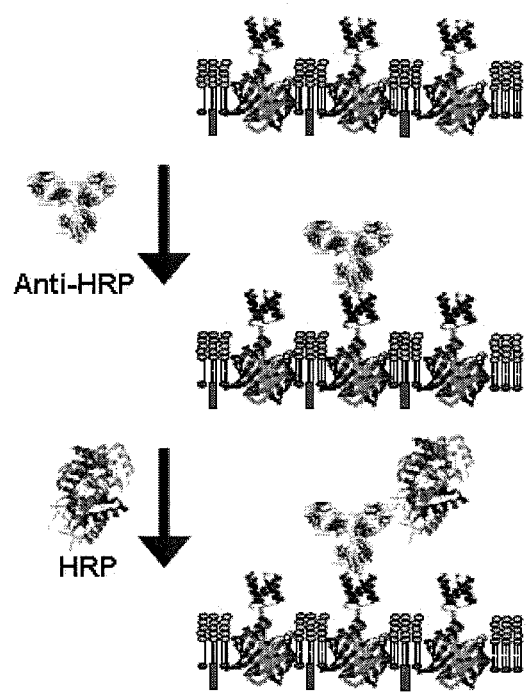
Figure 4B:
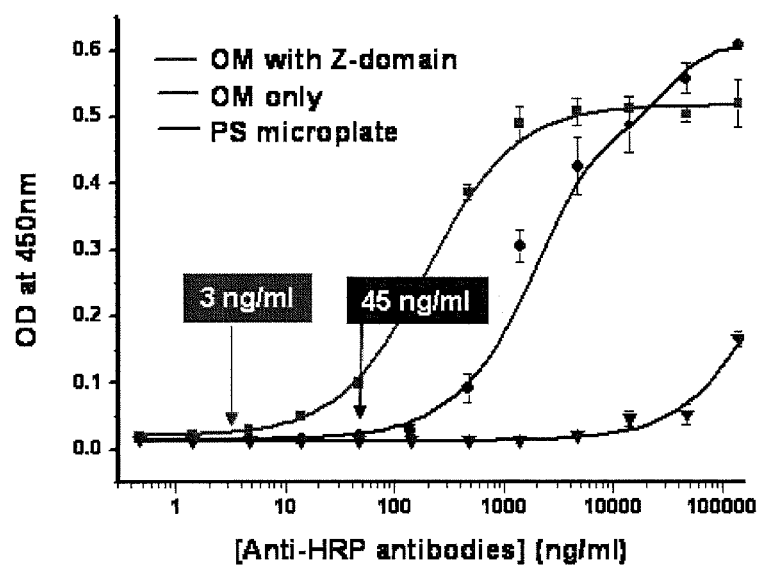
Figure 4C:
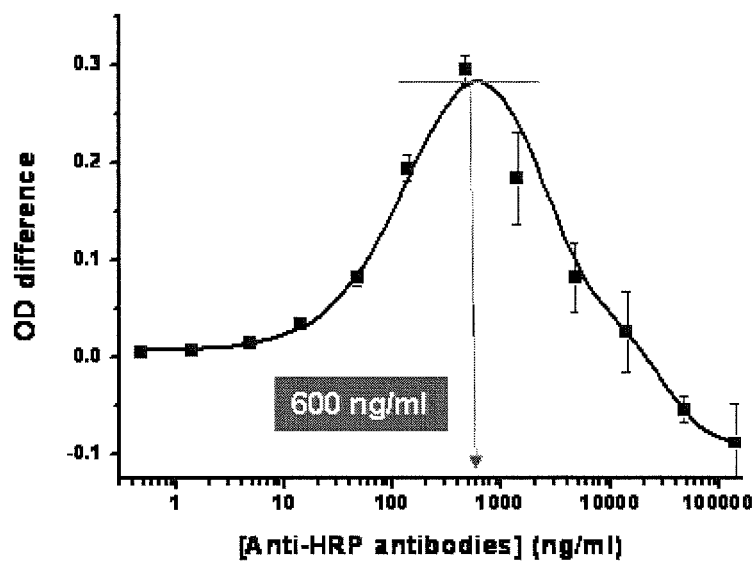
Figure 4D:
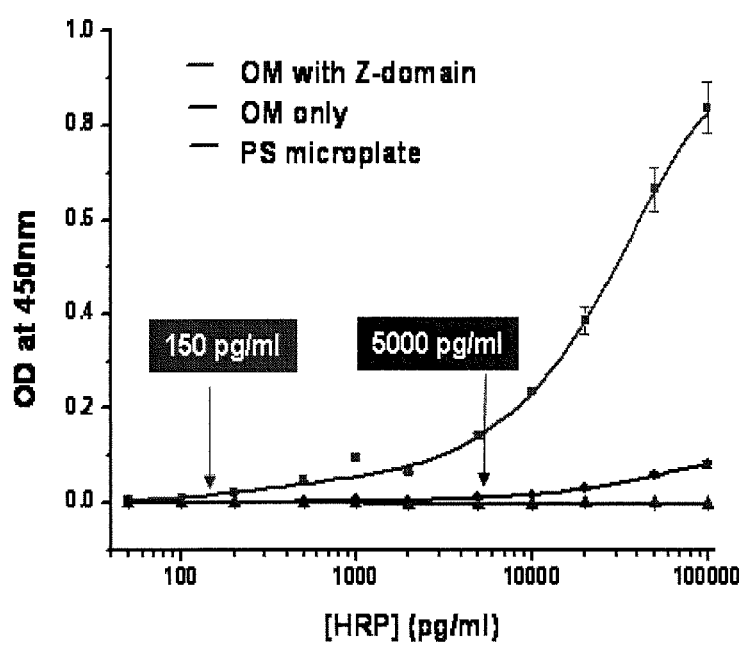
Figure 5A:
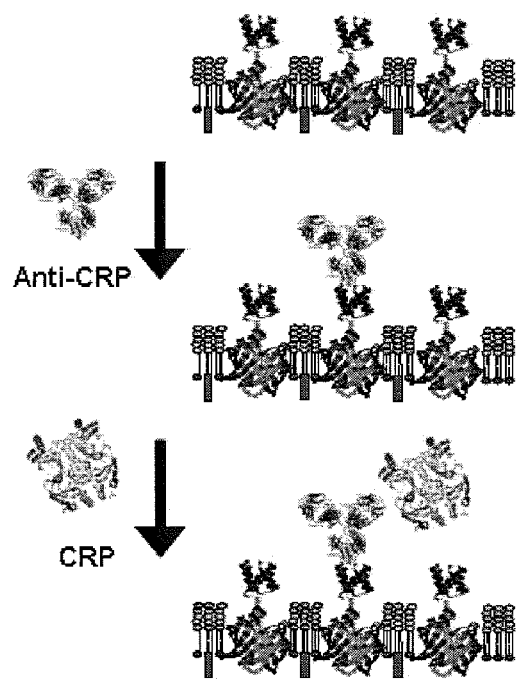
Figure 5B:
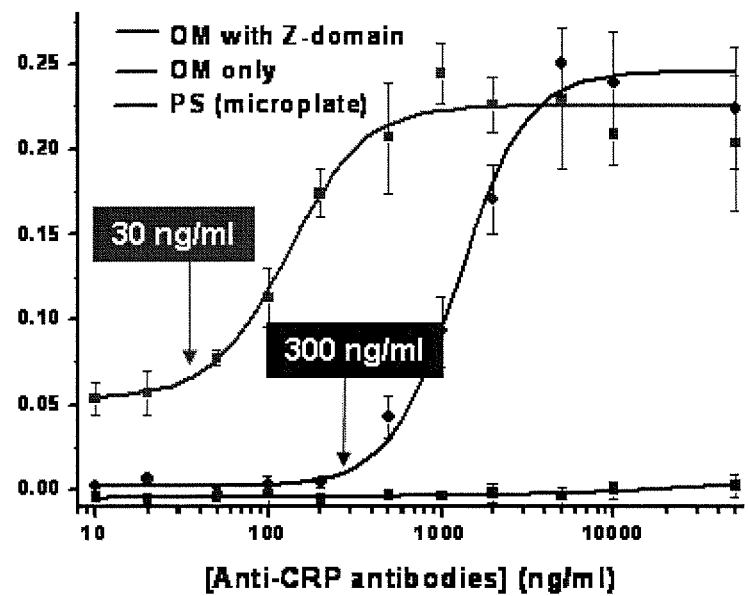
Figure 5C:
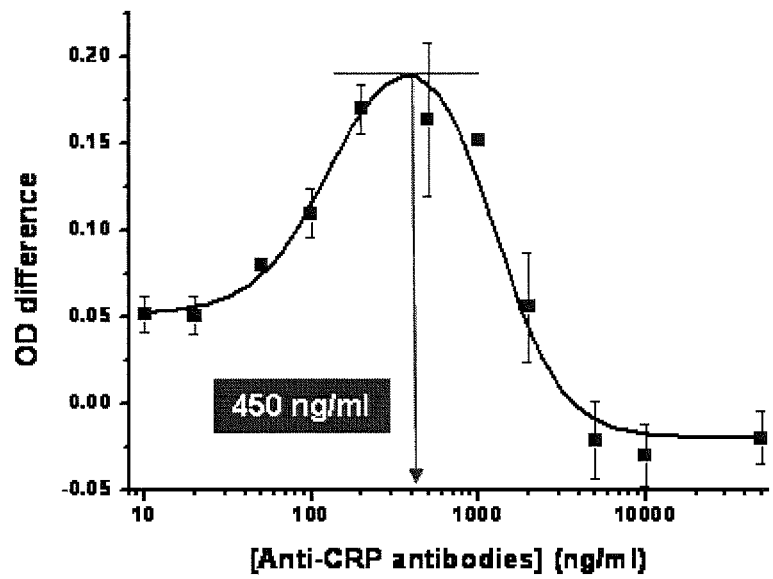
Figure 5D:
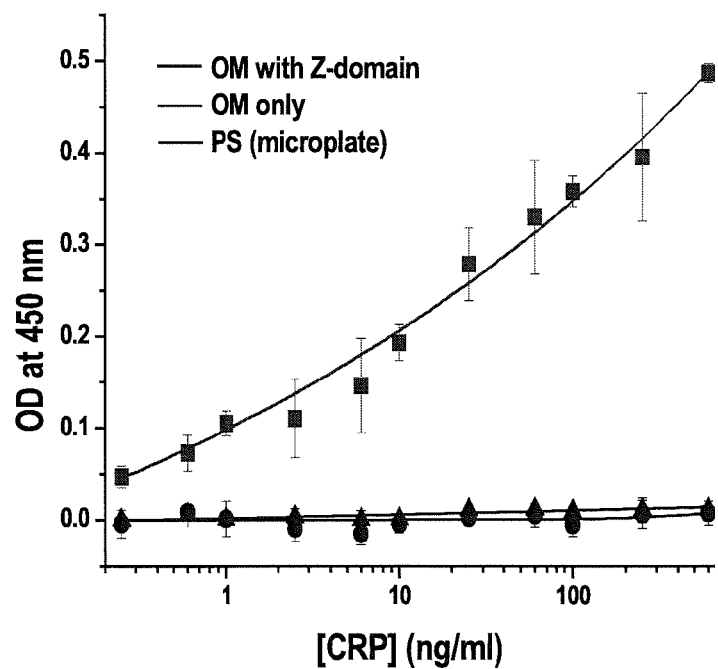

FIG. 3. Optimization of concentration for plate coating by using outer membrane from *E. coli* with autodisplayed Z-domain (■) and intact *E. coli* (●).

FIG. 4. HRP detection with an orientation controlled antibody layer (■) and a randomly oriented antibody layer as the conventional ELISA (●). (a) Schematics for assay configuration, (b) Comparison of assay response by treatment of HRP at the concentration of 1 ug/ml according to the concentration of immobilized anti-HRP antibodies, (c) Difference of the assay response between antibody layer with controlled orientation and randomly oriented antibody layer, (d) Assay response between antibody layer with controlled orientation and randomly oriented antibody layer at the antibody concentration of the maximum assay response difference (600 ng/ml).

FIG. 5. CRP detection with an orientation controlled antibody layer (■) and a randomly oriented antibody layer as the conventional ELISA (●). (a) Schematics for assay configuration, (b) Comparison of assay response by treatment of CRP at the concentration of 1 ug/ml according to the concentration of immobilized anti-HRP antibodies, (c) Difference of the assay response between antibody layer with controlled orientation and randomly oriented antibody layer, (d) Assay response between antibody layer with controlled orientation and randomly oriented antibody layer at the antibody concentration of the maximum assay response difference (450 ng/ml).

Figure 6:
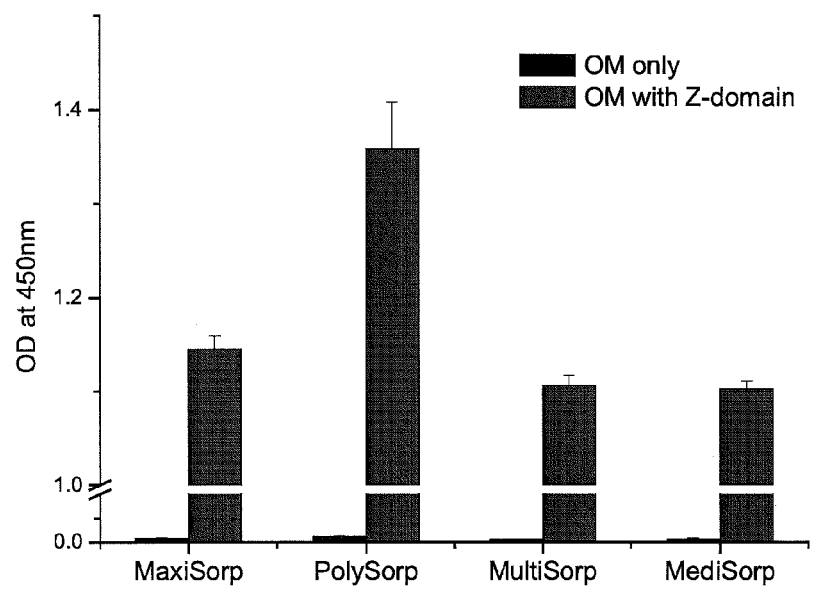

FIG. 6. OM layer on different surfaces with controlled hydrophobicity. OM layers with Z-domain and without Z-domain were separately prepared on the microplates, and then HRP-labeled antibodies were treated. The 'OD' at the Y-axis means the chromogenic signal at the wavelength of 450 nm by the treatment of TMB.

Figure 7:
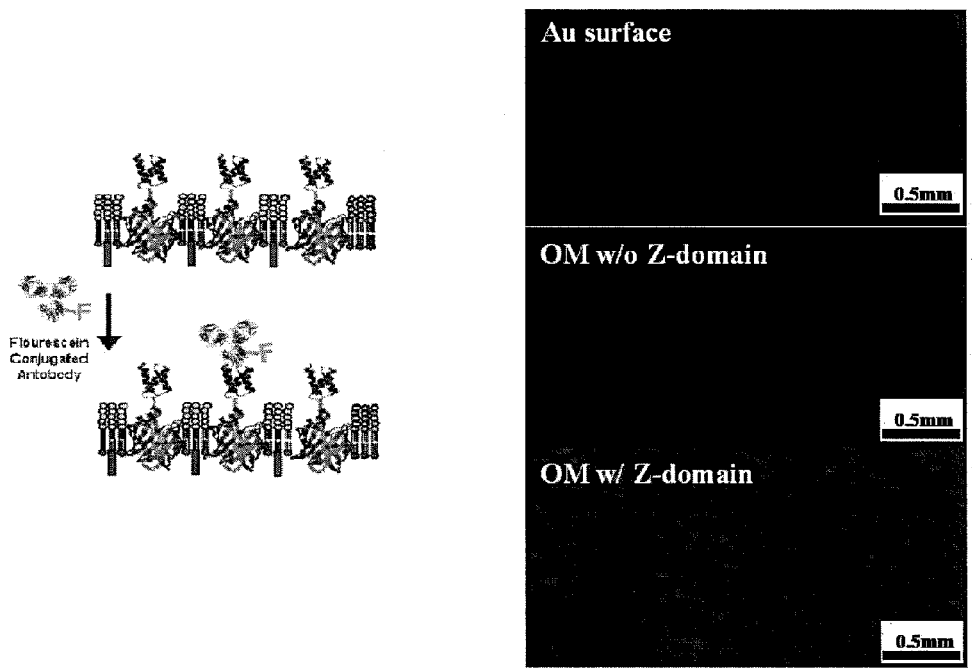

FIG. 7. IgG binding activity of OM layer prepared on Au surface. Fluorescein labeled antibodies were treated to the surface of gold with BSA layer, with OM layer from intact *E. coli* without Z-domain, with OM layer with Z-domain. The area of fluorescence image is fixed to be 50 mm×10 mm.

Figure 8:
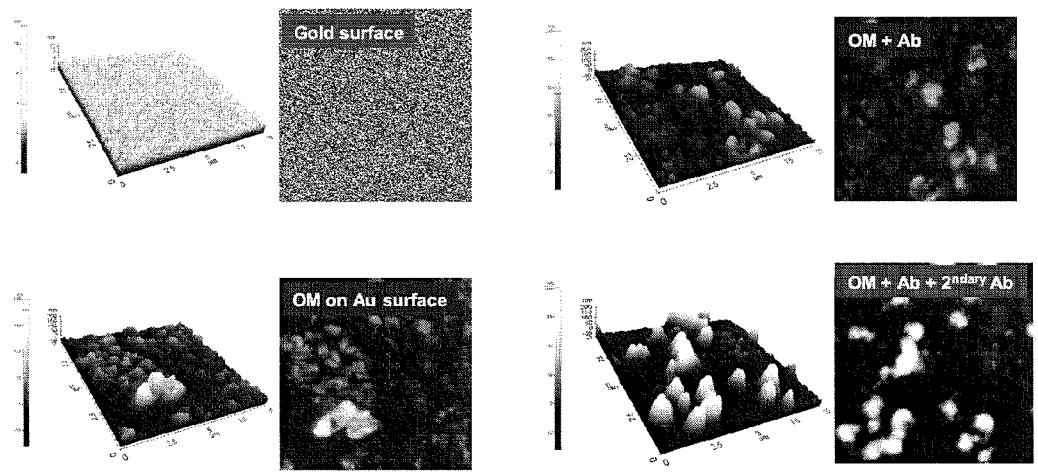

FIG. 8. AFM (atomic force microscopy) images of OM layer with antibodies (IgG's). The area of each image is adjusted to be 10 μm×10 μm and the Z-axis is fixed to be 100 nm. Bare gold surface was coated with OM particle and then antibodies were treated to the OM layered gold's surface.

Figure 9:
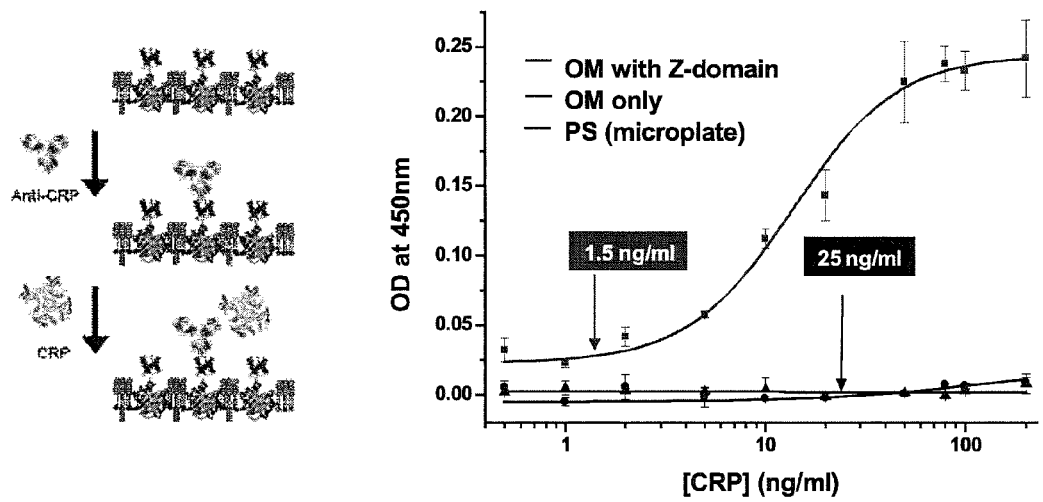

FIG. 9. Comparison of ELISA based on OM layer with conventional method.

Figure 10A:
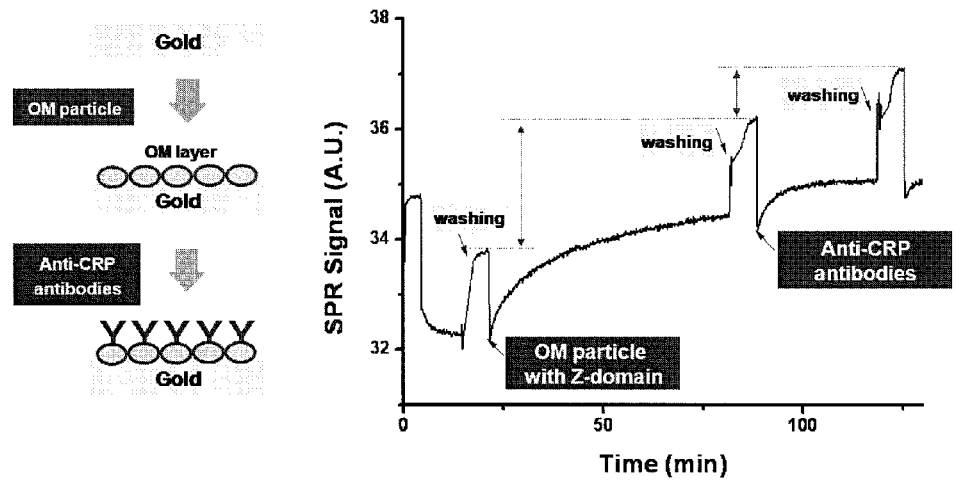
Figure 10B:
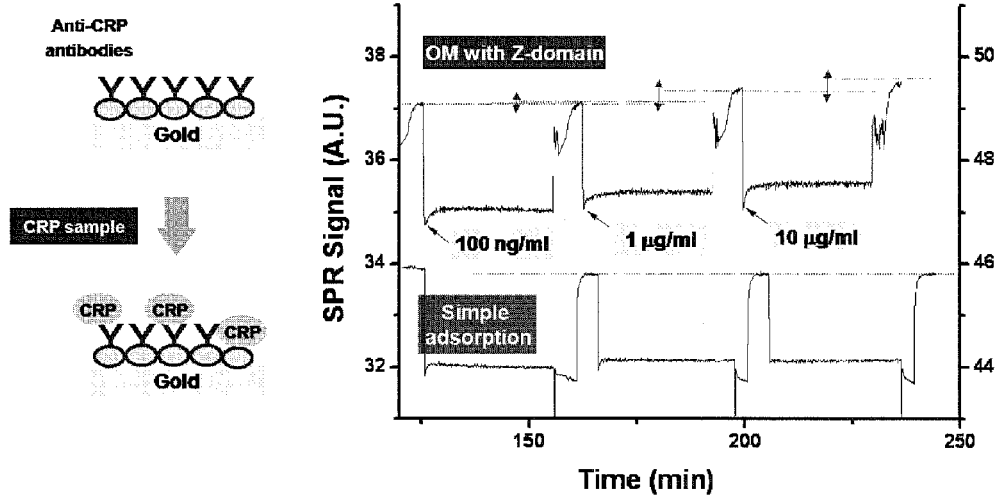

FIG. 10. SPR response by the interaction of OM layer with analytes. Y-axis at the left side is for the SPR biosensor with OM layer and Y-axis at the right side is for the SPR biosensor with antibody-layer by physical adsorption.

Figure 11:
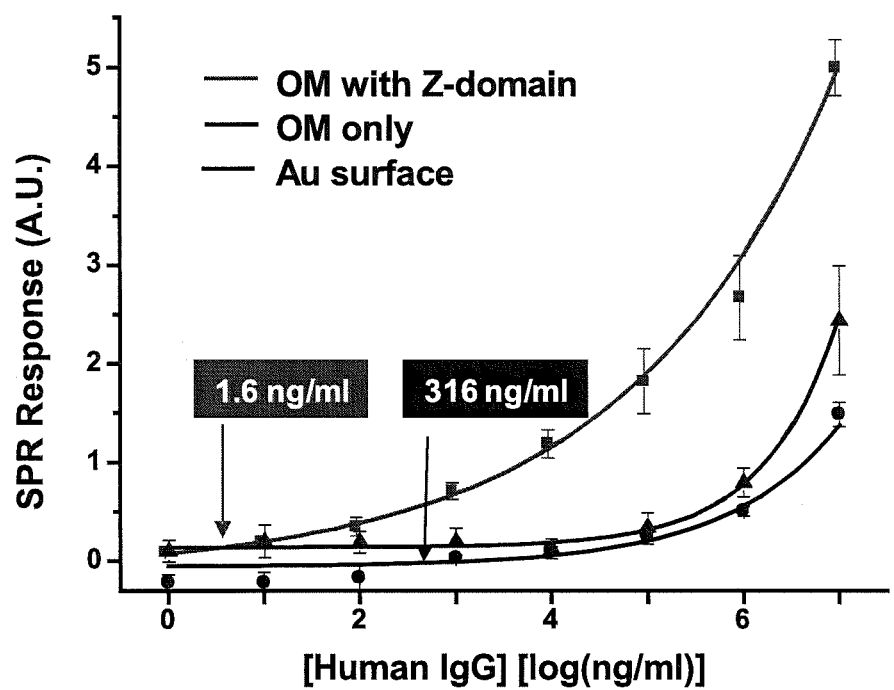

FIG. 11. Comparison of SPR responses for hIgG detection by using OM layer with anti-hIgG antibodies as a molecular recognition layer (square) and by using a physically adsorbed layer of anti-hIgG antibodies (triangle). The SPR response by OM layer without Z-domain was used as a negative control (circle).

Figure 12A:
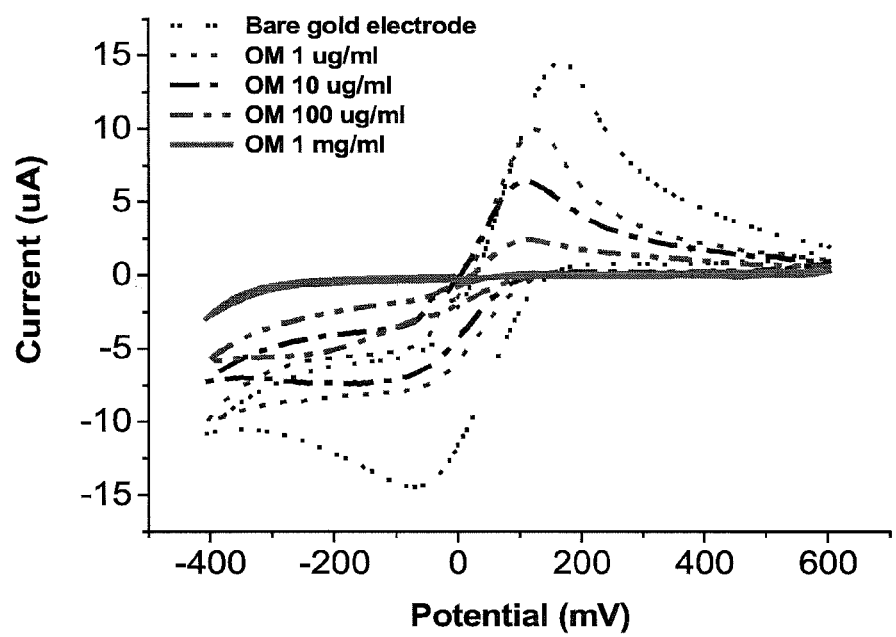
Figure 12B:
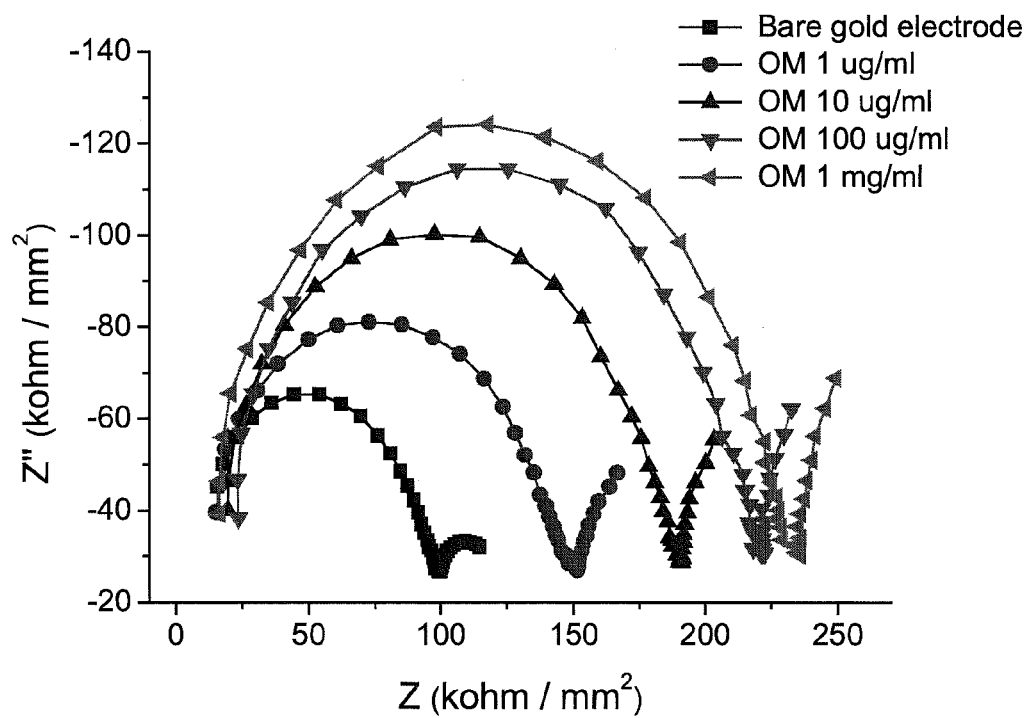
Figure 12C:
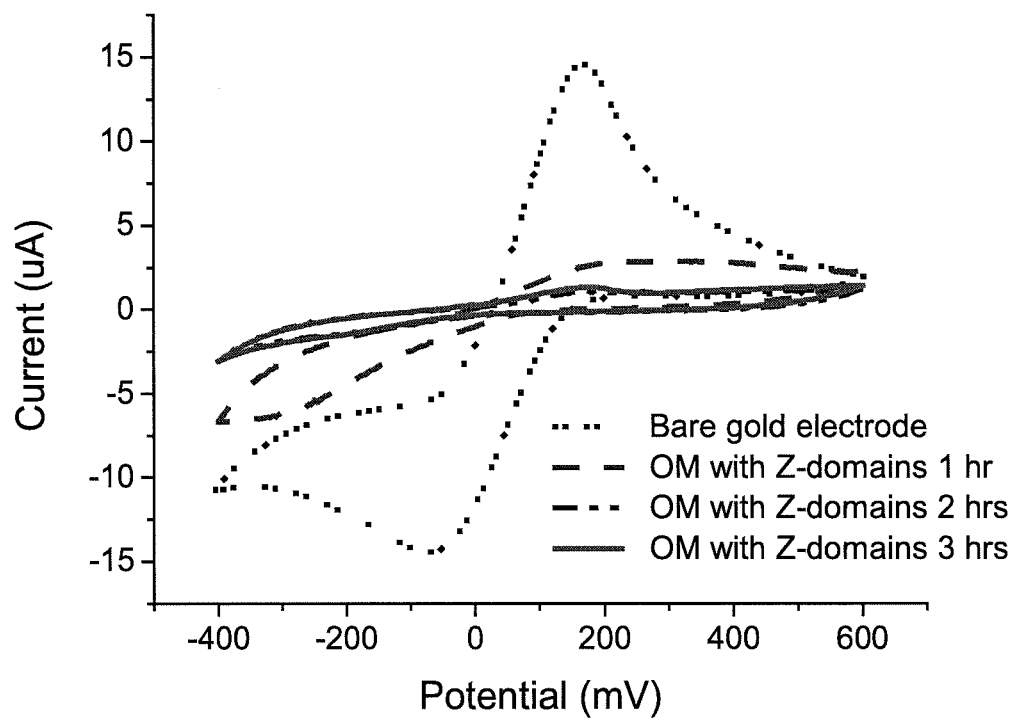

FIG. 12. Electrochemical analysis of OM layer. (a) CV diagrams of OM layer according to the incubated OM particle concentration. The scan rate was 10 mV/s and 10 mM $Fe(CN)_6^{3-/4-}$ was used as a redox couple. (b) Nyquist plot from impedance analysis of OM layers by incubating the OM solution at different concentrations. The charge transfer resistance was calculated at the x-cut of the hemispheric response curve. (c) Monitoring of OM layer formation by CV analysis according to incubation time. The area of CV diagram was observed to be changed according to the incubation time of OM solution at the fixed concentration of 1 mg/ml.

Figure 13:
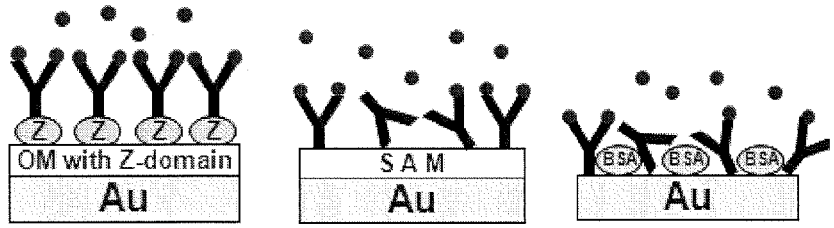
Figure 13:
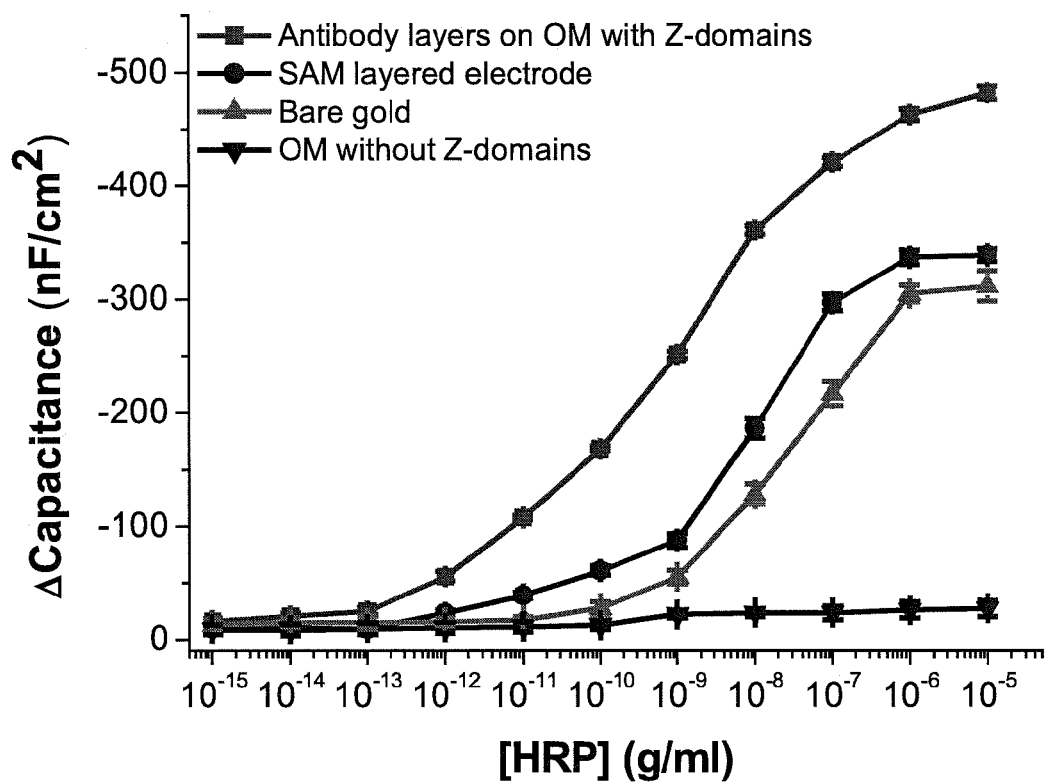

FIG. 13. Comparison of the capacitive biosensor responses to HRP (model analyte) concentration by using different immunoaffinity layers. Three different antibody layers were prepared by using the OM layer with autodisplayed Z-domains, SAM, and by physical adsorption of antibodies to gold electrode (n=3).

Figure 14:
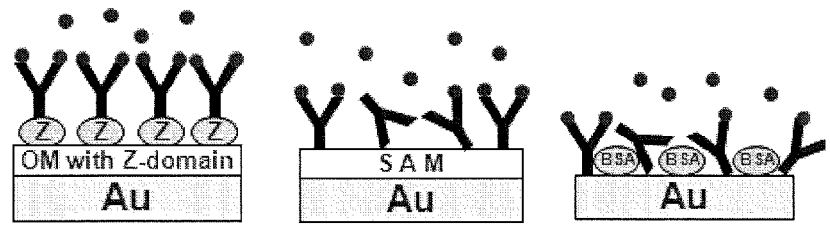
Figure 14:
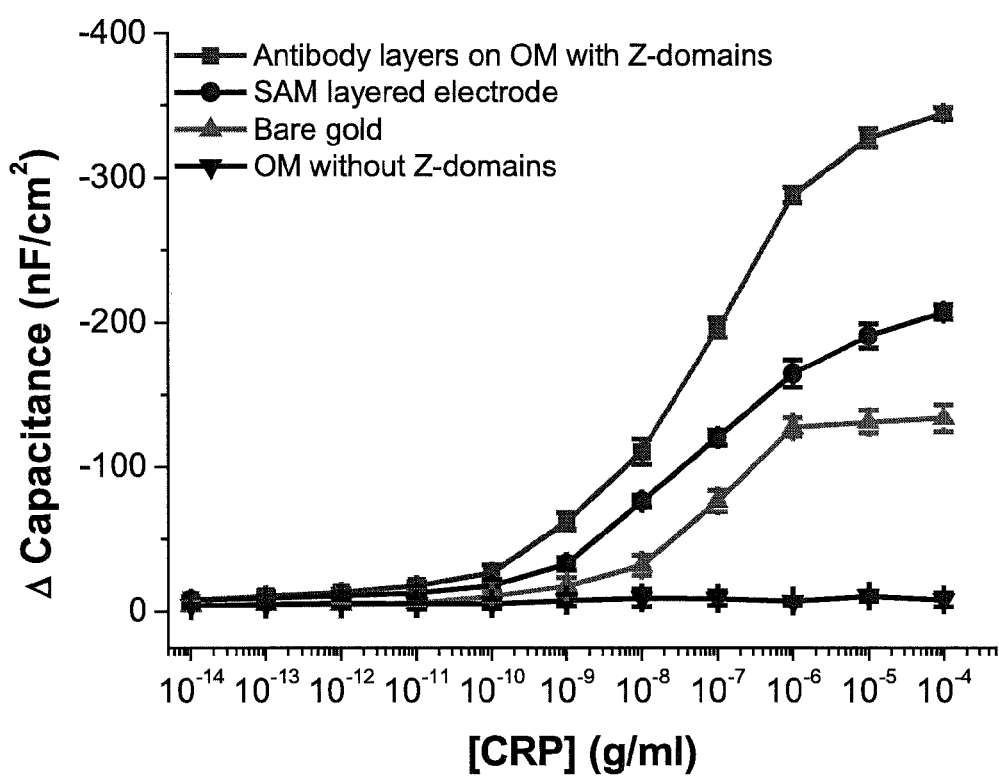

FIG. 14. Detection of adsorption of C-reactive protein (CRP). Standard curve by using an antibody layer immobilized to the OM layer with autodisplayed Z-domains was compared with an antibody layer prepared by physical adsorption (n=3).

Figure 15:
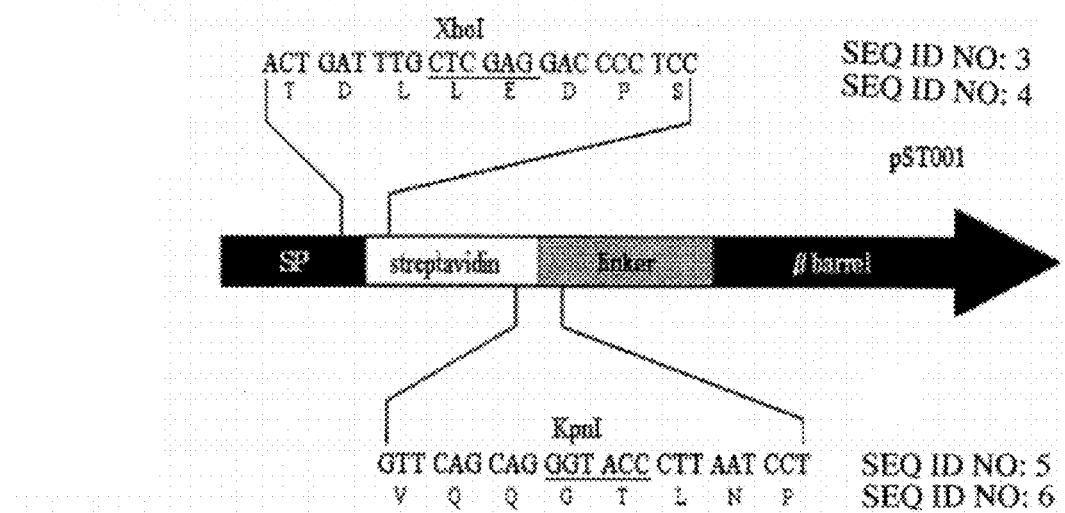

FIG. 15. The autodisplay vector of streptavidin gene named to be pST001.

Figure 16:
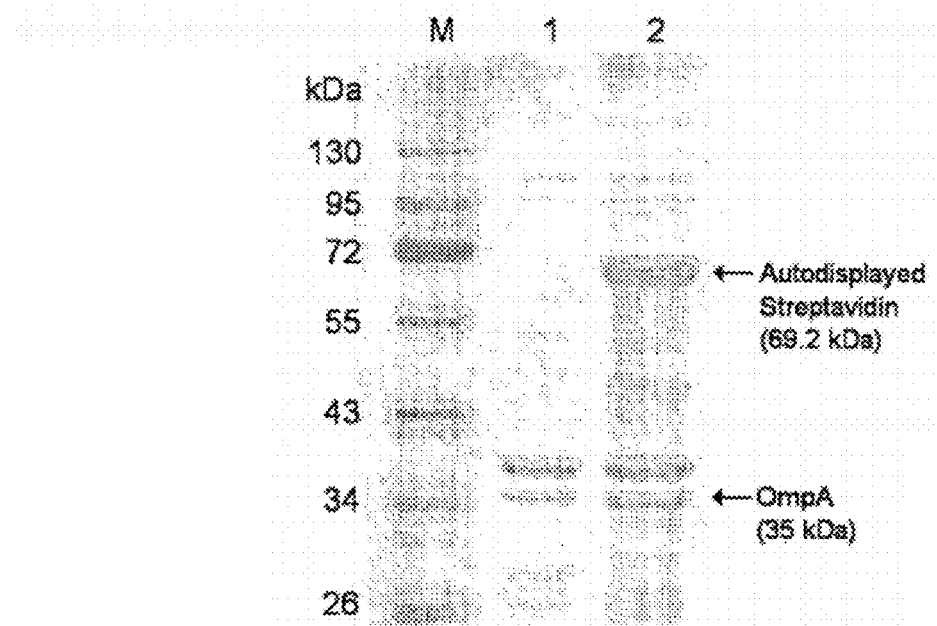

FIG. 16. Analysis of the outer membrane proteins by using SDS-PAGE. The lane M indicates the molecular weight markers. Lane 1 and lane 2 show the outer membrane proteins from UT5600(DE3) without autodisplayed streptavidins, and the outer membrane proteins from UT5600 (DE3) transformed with pST001 for the autodisplay of streptavidins, respectively.

Figure 17:
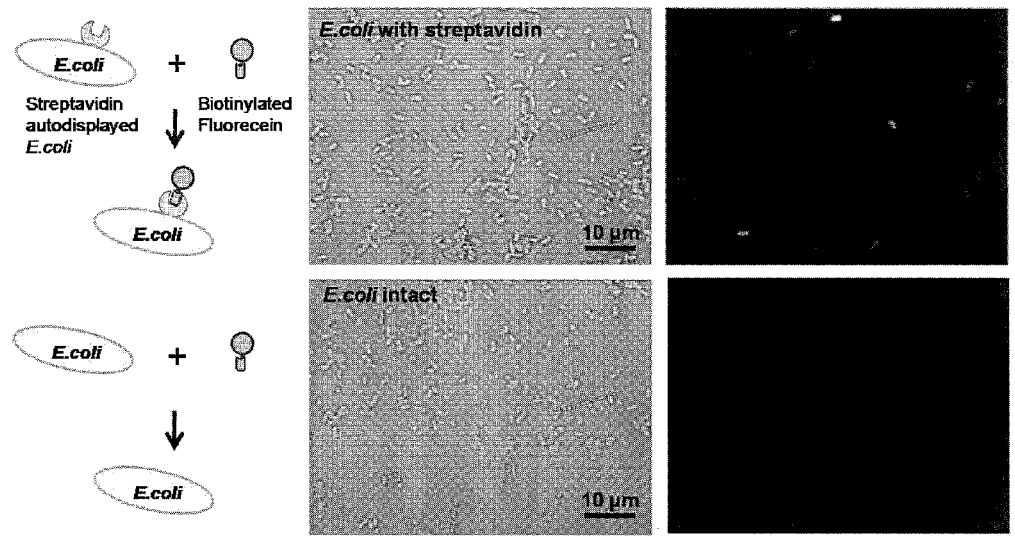

FIG. 17. Activity test of the autodisplayed streptavidin by treatment of biotinylated fluorescein. The phase-contrast and fluorescence images were taken by using UT5600(DE3) and UT5600(DE3) pST001 cells after treatment of biotinylated fluorescein.

Figure 18:
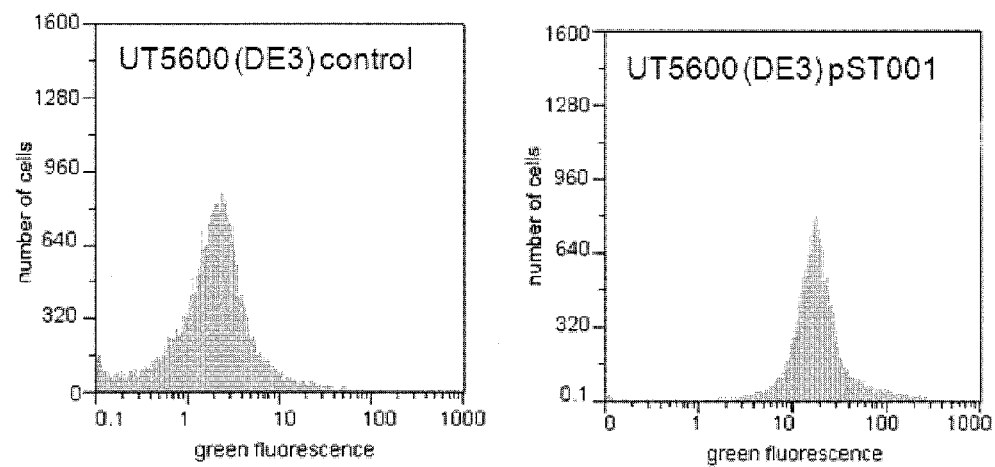

FIG. 18. Flow cytometric analysis of the biotin-binding activity. The E.coli transformed with pST 001 and the intact E.coli were analyzed after the treatment of biotinylated fluorescein.

Figure 19A:
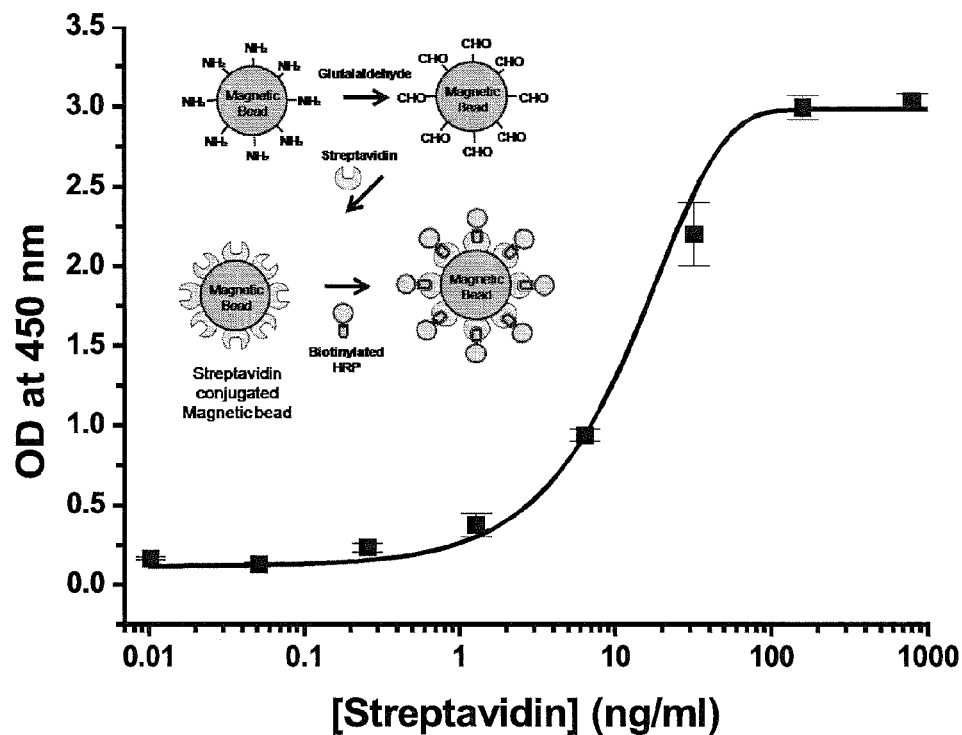
Figure 19B:
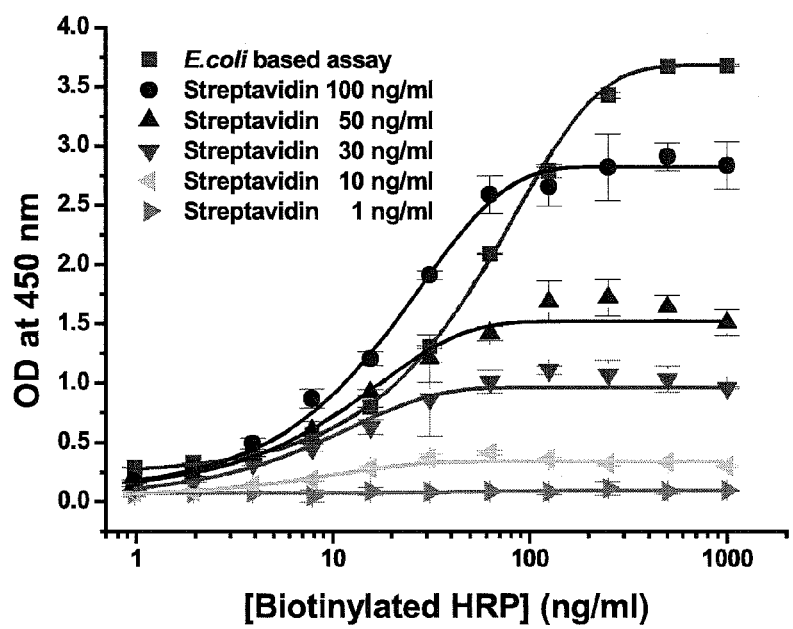

FIG. 19. Biotin-binding activity of E.coli cell with autodisplayed streptavidin in comparison with streptavidin coated magnetic beads. (a) Biotin-binding activity of magnetic bead with different amount of immobilized streptavidins (n=3). The maximum biotin binding activity was obtained by treatment of streptavidin solution at the concentration of 100 ng/ml. (b) The biotin-binding activity of E.coli with autodisplayed streptavidins in comparison with magnetic beads. The magnetic beads were reacted with the same concentration of biotinylated HRP (n=3).

Figure 20:
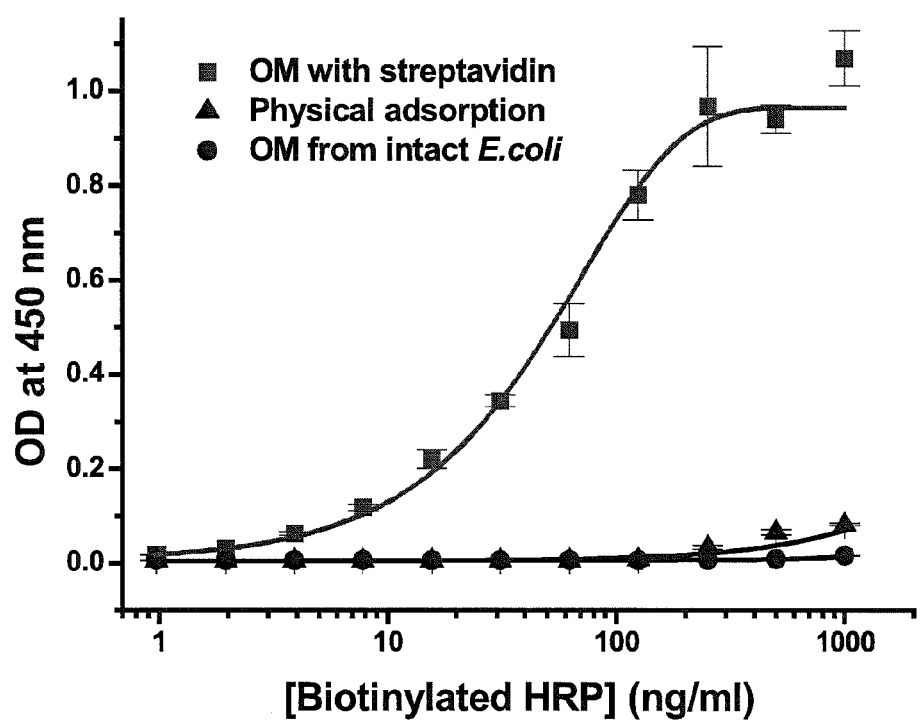

FIG. 20. Biotin-binding activity of the outer membrane layer of E.coli with autodisplayed streptavidins. The biotin-binding activity was estimated by treating biotinylated HRP and chromogenic substrate (TMB). To compare the activity of streptavidin, physically adsorbed outer membrane layer of intact E.coli and biotinylated HRP were used as negative controls.

Figure 21:
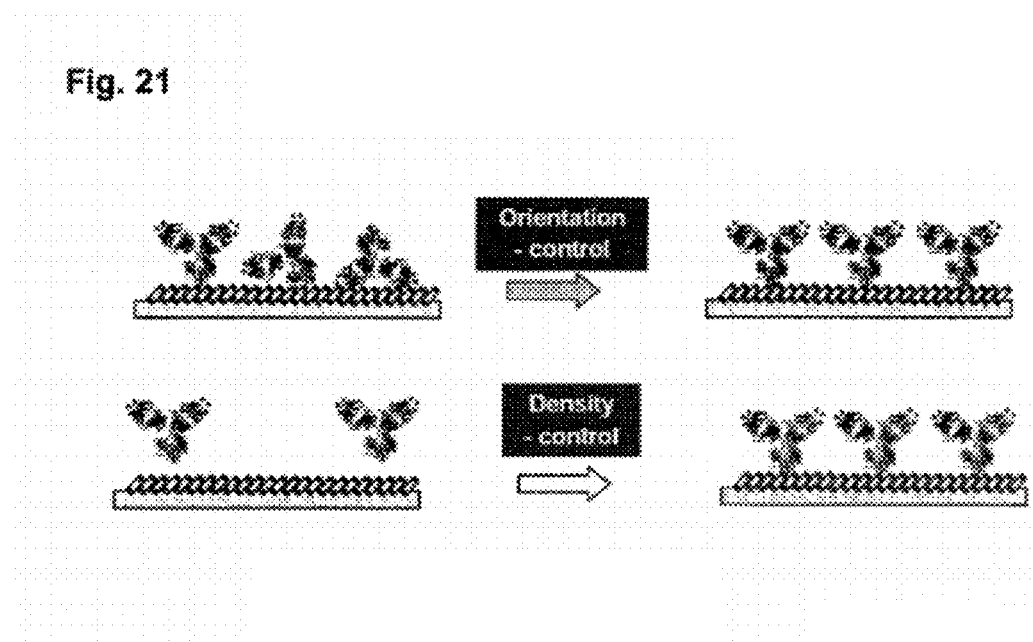

FIG. 21. Illustration of orientation control and density control.

Figure 22:
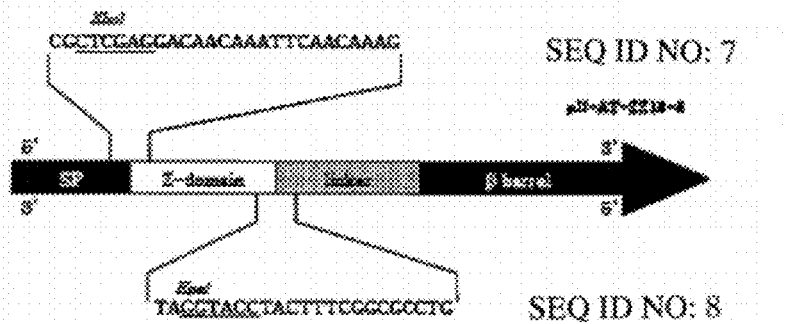

FIG. 22. The autodisplay vector of the Z domain.

Figure 23:
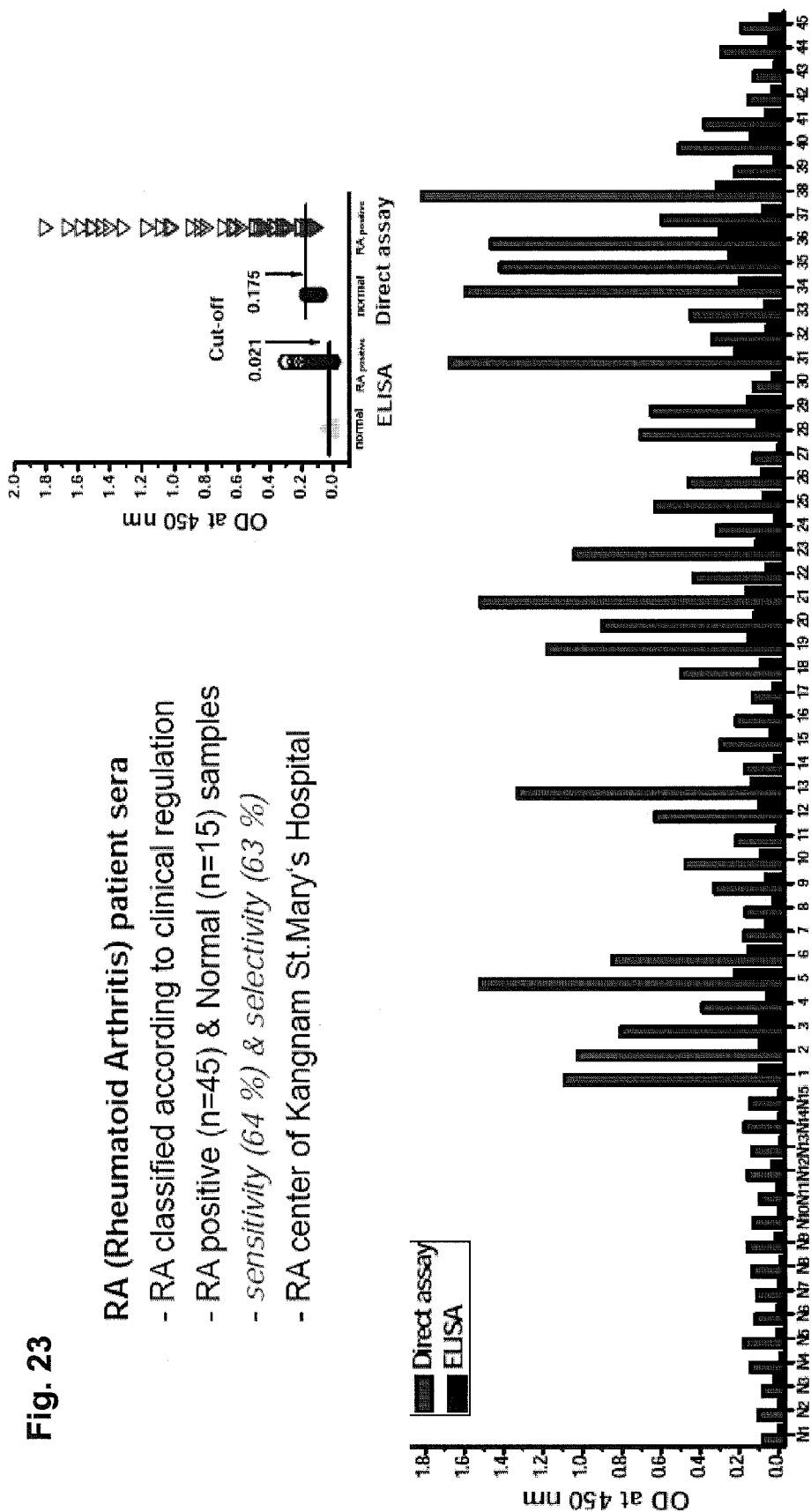

FIG. 23. Comparison of ELISA test employing anti-CRP antibodies, and a direct test according to the present invention employing carriers, in sera rheumatoid arthritis positive patients (1-45) and control patients (N1-N15) as described in Example 5.

Figure 24:
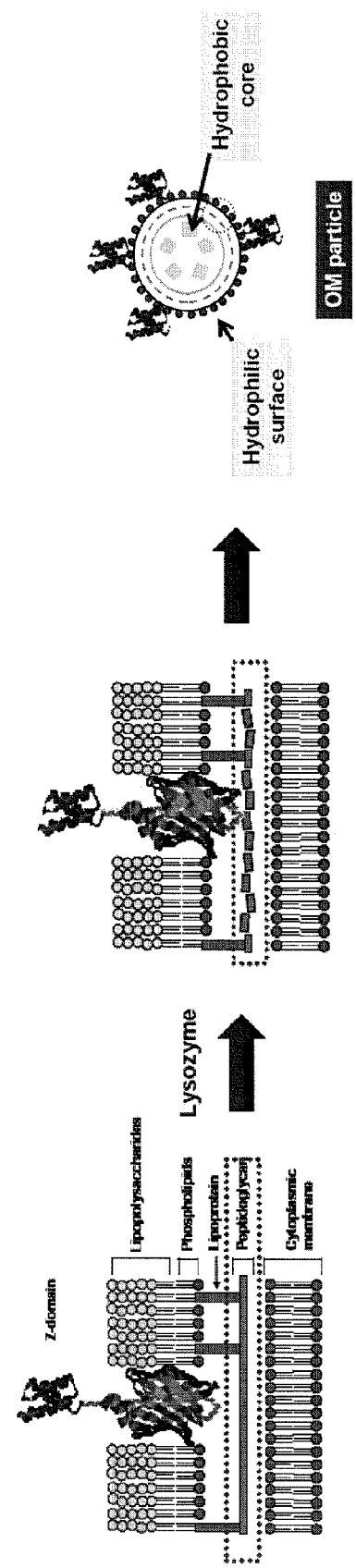

FIG. 24. Production of outer membrane particles

Figure 25:
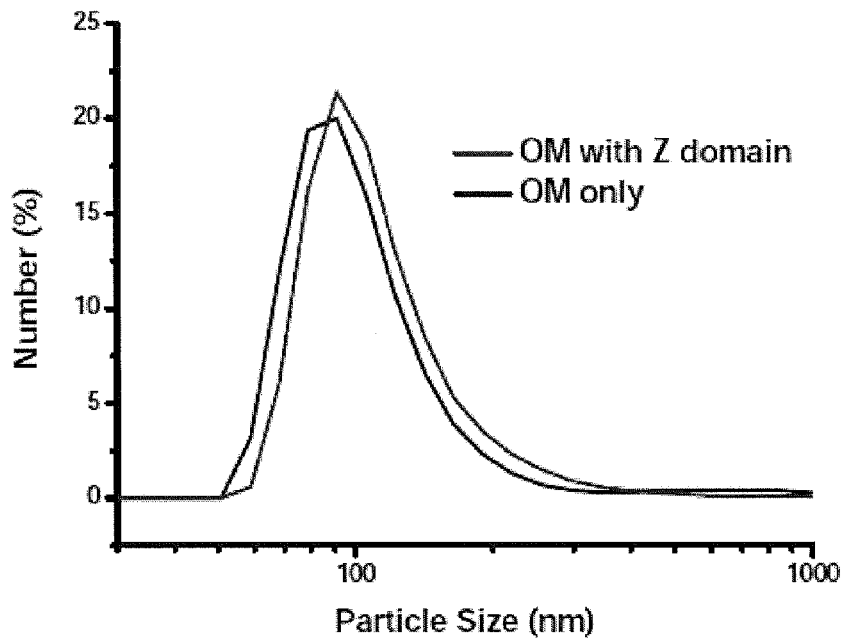

FIG. 25. Size distribution of outer membrane particles (OM) comprising Z domain and outer membrane particles only.

Figure 26:
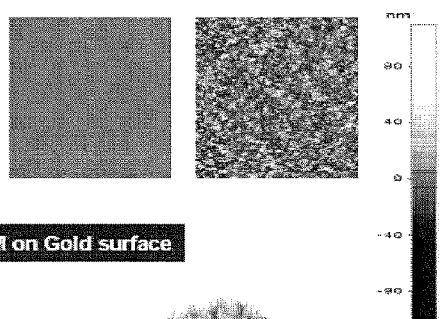
Figure 26:
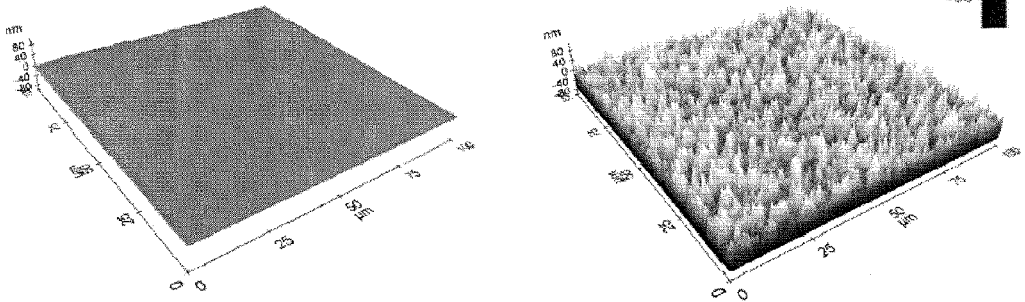

FIG. 26. AFM (atomic force microscopy) images of an OM. Bare gold surface (control, left-hand figure below; insert, left-hand figure) was coated with OM particles (right-hand figure below; insert, right-hand figure).

Figure 27:
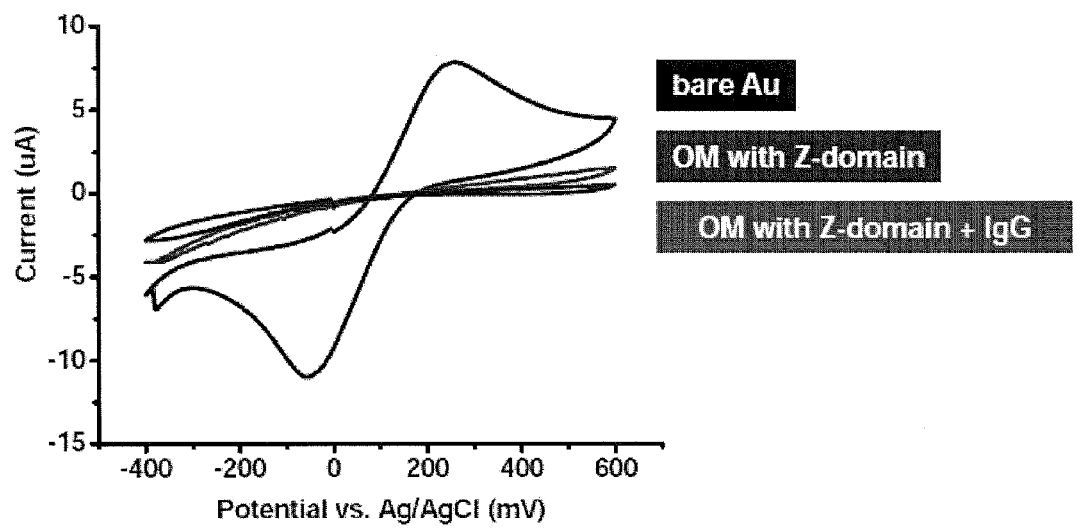

FIG. 27. Electrochemical analysis of OM layer. CV diagrams of a bare gold surface (5×5 mm), a gold surface coated with an OM layer comprising a Z domain, and an a gold surface coated with an OM layer comprising a Z domain contacted with IgG. The scan rate was 10 mV/s (average after four cycles). 1 mM $Fe(CN)_6^{3-/4-}$ was used as a redox couple.

Figure 28:
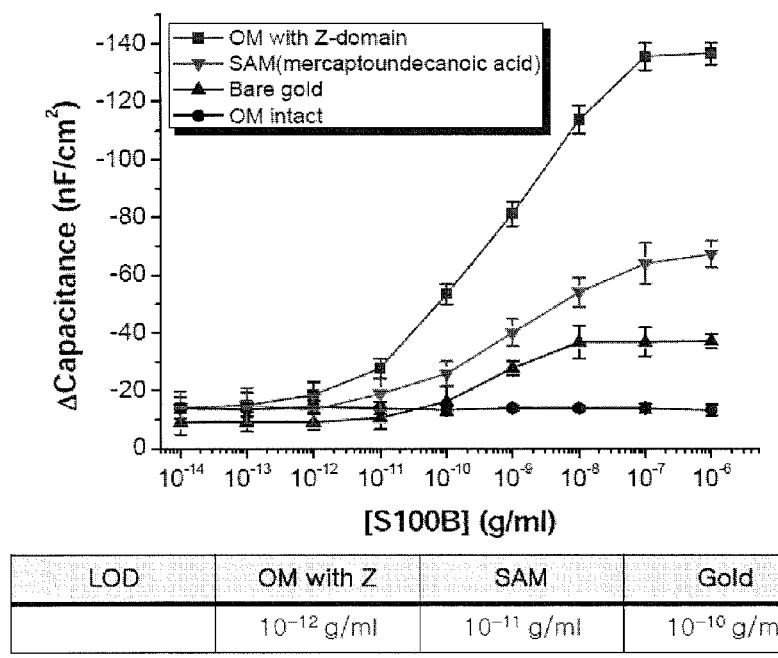

FIG. 28. Detection of S100B protein in sera. Comparison of sensors comprising IgG antibodies directed against S100B immobilized upon a bare gold surface, on SAM (mercaptoundecanoic acid), and on a surface comprising an OM layer comprising the Z domain of protein A, as described in Example 1. For control purposes a sensor comprising an OM layer without Z domains is employed.

Figure 29:
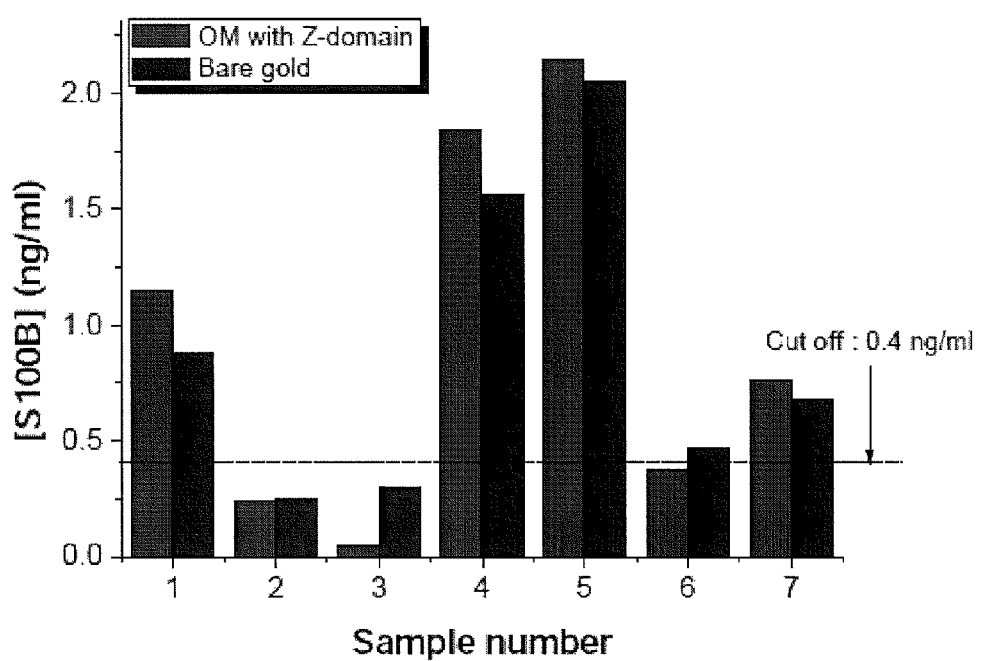

FIG. 29. Determination of S100B concentration in patients cerebrospinal fluid. Samples from 7 patients have been analysed. Comparison of sensors comprising IgG antibodies directed against S100B immobilized upon a bare gold surface, and on a surface comprising an OM layer comprising the Z domain of protein A (sensor of the present invention, as described in Example 1). S100B concentrations obtained by the sensor of the present invention are confirmed by the standard sensor comprising a bare gold surface.

EXAMPLE 1

Hyper Sensitive Immunoassay Based on Outer Membrane of E. coli with Autodisplayed Z-Domain 1.1 Introduction The Z-domain of protein-A was expressed on the surface of E. coli outer membrane by autodisplay technology as a fusion protein of AIDA-1 (FIG. 22), and the IgG-binding activity of the autodisplayed Z-domains was confirmed. Here, a new immunoassay with a hyper sensitivity was presented by coating the E. coli outer membrane with the autodisplayed Z-domains on a microplate.

The outer membrane of E. coli with autodisplayed Z-domain was isolated by using lysozyme reaction and sequential centrifugation. The E. coli outer membrane layer was formed on the microplate by using the hydrophobic interaction between the isolated outer membrane and the microplate surface. The driving force for the layer formation was proven to be the hydrophobic interaction by using microplates with controlled hydrophobicity.

The limit of detection (LOD) and the sensitivity by the new immunoassay were determined to be far improved in comparison to the conventional ELISA by using HRP as a model analyte. The applicability of the new immunoassay for medical diagnosis was demonstrated by the detection of C-reactive protein (CRP) which is known to be a biomarker protein for inflammatory diseases.

In this work, the outer membrane of the autodisplaying E. coli was isolated by using lysozyme reaction and sequential centrifugation steps. The formation of E. coli outer membrane layer on the microplate was demonstrated by using microplates with controlled hydrophobicity, and the driving force of the layer formation was proven to be the hydrophobic interaction between the outer membrane and the microplate surface. The effect of orientation control was evaluated by using HRP as a model protein and the feasibility of this immunoassay with autodisplayed Z-domain was demonstrated by the detection of C-reactive protein (CRP) which is known to be a biomarker protein of inflammatory diseases.

1.2 Materials and Methods 1.2.1 Materials

Purified C-reactive protein (CRP), Anti-CRP antibodies (polyclonal), anti-hIgG antibodies labeled with Cy3 (polyclonal), anti-HRP antibodies (polyclonal), anti-mIgG antibodies labeled with HRP (polyclonal), anti-CRP antibodies conjugated with HRP (polyclonal) were bought from AbCam (Cambridge, UK). Aprotinin was purchased from Roche Korea (Seoul, Korea). Phenylmethanesulfonyl fluoride, Bovine serum albumin (BSA), lysozyme, DNase, horseradish peroxidase (HRP) and all of the other chemicals (of analytical grade) were purchased from Sigma-Aldrich Korea (Seoul, Korea).

1.2.2 Preparation of E. coli outer membrane with autodisplayed Z-domain

The autodisplay was performed by transformation with an autodisplay vector constructed by the cloning of the antibody binding Z-domain from S. aureus. The outer membrane (OM) of E. coli with autodisplayed Z-domain was prepared by using lysozyme reaction and subsequent isolation procedures as described (Hantke, 1981; Schultheiss et al., 2002). The OM of intact E. coli was also prepared by using the same procedure (see FIG. 24). Expression of Z domain only did not influence size distribution of outer membrane particles (about 90% of particles had a size of 80-120 nm, see FIG. 25).

1.2.3 Preparation of an OM layered microplate for ELISA

The OM solution was prepared at the protein concentration of 300 μg/ml in PBS. For each well of microplate, 100 μl of the OM solution was incubated for 2 hours at room temperature. Then, the microplate was washed with 0.1% Tween 20 in PBS for three times. For the immobilization of detection antibodies, the corresponding antibody solution (100 μl) was dispensed at each well of a 96-well microplate and was incubated for 1 hour at room temperature. The HRP assay was reported by the chromogenic reaction of TMB solution (Pierce, USA). After quenching with 2 M sulfuric acid solution, the optical density was measured by using an ELISA reader (Vesamax, Molecular Devices, USA) at the wavelength of 450 nm.

1.3 Results and Discussion 1.3.1 Formation of OM Layer on Microplate

The outer membrane of $E.\ coli$ was known to have the layered structure composed of lipopolysaccharide (LPS), phospholipid, lipoprotein, peptidoglycan on the plasma membrane. For the isolation of the outer membrane of $E.\ coli$, the peptidoglycan layer of the outer membrane was hydrolysed by the reaction of lysozyme. Then, the isolated outer membrane was solubilized by using sarcosine. From the subsequent centrifugation steps, the outer membrane was isolated as outer membrane particle which was analyzed to have negatively charged surface with a diameter of 100 nm by using a particle analyzer. As the negative charge of $E.\ coli$ was generated from the LPS layer at the surface of $E.\ coli$ cell, the surface of the outer membrane particle was expected to be negatively charged. In this case, the core of the outer membrane particle was expected to comprise lipoproteins.

When the particles with a hydrophilic surface were treated to the hydrophobic substrate, the particles were known to make an ordered layer through the hydrophobic interactions. In the case of the prepared outer membrane particles, the negatively charged LPS layer is directed outside of the hydrophobic substrate and the relatively hydrophobic lipoprotein layers directed to core of the particle. As the Z-domain is expressed as a fusion protein located at the lipopolysaccharide, Z-domain is also found at the surface of the ordered outer membrane layer. Actually, the surface charge of an intact $E.\ coli$ was measured to be −25.5 mV from the zeta potential measurement. For $E.\ coli$ with autodisplayed Z-domain and the outer membrane particle, the zeta potentials were measured to be −25.1 mV and −22.5 mV, respectively. These results indicated that the layered structure of $E.\ coli$ outer membrane was maintained for $E.\ coli$ with autodisplayed Z-domain as well as the outer membrane particle.

The formation of such an ordered layer by the hydrophobic interaction was tested by measuring the IgG binding activity of the formed layer on several microplate surfaces with controlled hydrophobicity. The outer membrane layer was formed on the microplates by treatment of the outer membrane particles at the same concentration of 100 μg/ml protein by incubation. Then, the IgG labeled with HRP was treated and the bound amount to Z-doman was estimated by the chromogenic reaction between HRP and TMB. As shown in FIG. 2, the IgG binding activity was linearly correlated to the hydrophobicity of the surface and the most hydrophobic surface shows the highest IgG binding activity. These results indicate that the formation of the outer membrane layer was derived by the hydrophobic interaction between the core side of the particle and the hydrophobic microplate surface.

The outer membrane particle from intact $E.\ coli$ cells was also treated to the microplates as a negative control for determination of the non-specific binding of the HRP labeled antibodies. As shown in FIG. 2, the IgG binding activity was decreased according to the hydrophobicity of the microplate surface. These results indicated that the outer membrane layer was more densely layered as the hydrophobicity of the microplate increased. For the outer membrane layer with autodisplayed Z-domains, the number of Z-domain for on the microplate was also increased according to hydrophobicity of the microplate. As the surface charge would be also increased, the most hydrophobic surface was expected to have the most hydrophilic surface, which can generally reduce the non-specific binding of proteins. Therefore, the non-specific binding of proteins can be effectively prevented by the outer membrane layer prepared on the hydrophobic microplate surface. As shown in FIG. 2, the polystyrene microplate presented the highest Z-domain activity and the microplate was used for the immunoassays in this work.

The optimal outer membrane concentration was estimated by using the polystyrene microplate. As shown in FIG. 3, different concentrations of outer membrane particles were treated to the microplate and then the activity of the Z-domain was determined by immobilizing HRP labeled antibodies. As a negative control, the outer membrane particle from intact $E.\ coli$ was also treated to the microplate. As shown in FIG. 3, the IgG-binding activity of the outer membrane layer with Z-domains was increased as the higher concentration of outer membrane particle was treated to the microplate. When the concentration of the outer membrane particle was more than 100 μg/ml protein, the IgG binding activity showed a saturated response. These results meant that the outer membrane layer has a saturated density of Z-domains at this concentration. In the case of negative control, the outer membrane particles at the lower concentration of less than 40 ug/ml showed that the adsorption of the antibodies were maintained at the baseline level. This result shows that the outer membrane layer could be formed to prevent the non-specific adsorption of proteins when the concentration of the treated outer membrane particle was higher than 40 ug/ml. Therefore, the concentration of the outer membrane particle at 100 ug/ml was optimal for the antibody immobilization as well as enough for the prevention of the non-specific binding of proteins.

1.3.2 ELISA with OM layered microplates

The Z-domain is the IgG-binding domain of protein A. Due to its specific binding activity to $F_c$ region of the antibodies, the outer membrane layer with the autodisplayed Z-domain formed on the microplates could be effectively used to immobilize the antibodies with a controlled orientation. The effect of orientation control with the audodisplayed Z-domain was estimated by comparing the analyte-binding activity of a randomly-oriented antibody layer. When the same concentration of antibodies was immobilized on a microplate, the randomly-oriented antibody layers would have smaller number of well-oriented antibodies at the unit area than the orientation-controlled antibody layers. In other words, the antibody layer with random-orientation required higher concentration antibodies for the detection of an analyte than the orientation-controlled antibody layer because only smaller number of antibodies had the proper orientation for the analyte detection.

In this work, HRP was exploited as a model analyte as shown in FIG. 4 (a) and the concentration of antibodies required for the detection of HRP was measured by using a randomly-oriented antibody layer (●) and an orientation-controlled antibody layer (■). The randomly-oriented antibody layer was prepared by physical adsorption of antibodies as in the case of ELISA. The negative control layer was prepared by using outer membrane layer of intact E. coli for the estimation of the non-specific binding (▼). The amount of bound analyte (HRP) was evaluated by treatment of the chromogenic substrate of HRP (TMB) and the optical density at the wavelength of 450 nm was measured.

As shown in FIG. 4 (b), the minimum of antibody concentration required for the detection of the HRP at the concentration of 10 ng/ml was estimated to be 3 ng/ml and 45 ng/ml for the antibody layers with the controlled-orientation by Z-domain (■) and the random-orientation (●), respectively. This result showed that 15-fold lower concentration of antibody was required for the detection of the analyte (HRP) at the same concentration by orientation control than the conventional ELISA.

By comparison of the assay results from the orientation-controlled antibody layer (■) and randomly-oriented antibody layer (●) as shown in FIG. 4 (b), the maximum difference of the assay results was observed at the antibody concentration of 600 ng/ml as shown in FIG. 4 (c). When an orientation-controlled antibody layer and a randomly-oriented antibody layer were prepared at this concentration, the orientation-controlled antibody layer showed more than 30-fold improved limit of detection as shown in FIG. 4 (d). This result meant that the maximum effect of the orientation control was as much as 30-fold in comparison to the randomly-oriented antibody layer.

Additionally, the saturated assay response from the orientation-controlled antibody layer (■) was observed to be far higher than randomly-oriented one (●) as shown in FIG. 4 (d). Such response difference should be resulted from the difference at the number of analyte binding sites. As the same concentration of antibodies was used for the immobilization, such a difference could be determined to be resulted from the orientation control effect.

The low non-specific binding of proteins to the outer membrane of E. coli also contributed for the sensitivity improvement of E. coli based immunoassay. As non-specific binding of unrelated proteins usually results in a false positive signal in immunoassays, it should be reduced as low as possible (Ezan and Jacques, 2000). In this work, the response by the non-specific binding to the outer membrane of E. coli was evaluated by using the intact E. coli (UT5600) without autodisplayed Z-domain as a negative control. When the same concentration of anti-HRP antibodies were treated, the response by the immunoassay with intact E. coli (▼) was observed to be insignificant in comparison to the E. coli with autodisplayed Z-domain (■) at the whole analyte concentration range as shown in FIG. 4. These results showed that the non-specific binding to the outer membrane of E. coli observed to have nearly no influence on the result of E. coli based immunoassay. Usually, the hydrophilic surfaces are known to reduce the non-specific binding of proteins for immunoassay (Silin et al., 1997). As mentioned previously, the outer membrane of E. coli is known to be negatively charged (Hamadi et al., 2008), and the zeta-potential of intact E. coli (negative control) and the E. coli with autodisplayed Z-domain were measured to be −22.5 mV, −25.1 mV, respectively. Therefore, the significantly low non-specific binding of E. coli could be due to the hydrophilicity of the E. coli's outer membrane.

1.3.3 Application to the detection of C-reactive protein

The new immunoassay based on the microplate coated with the outer membrane was applied to the medical diagnosis by the detection of C-reactive protein (CRP) which is known to be a biomarker protein of the inflammatory diseases such as rheumatoid arthritis.

As shown in FIG. 5 (a), anti-CRP antibody was immobilized to the microplate coated with the outer membrane with autodisplayed Z-domains. the concentration of antibodies required for the detection of CRP at a fixed concentration of 25 ng/ml was measured by using a randomly-oriented antibody layer (●) and an orientation-controlled antibody layer (■). The randomly-oriented antibody layer was prepared by physical adsorption of antibodies as in the case of ELISA. The negative control layer was prepared by using outer membrane layer of intact E. coli for the estimation of the non-specific binding (▼). As shown in FIG. 5 (b), the minimum of antibody concentration required for the detection of the CRP at the concentration of 10 ng/ml was estimated to be 30 ng/ml and 300 ng/ml for the antibody layers with the controlled-orientation by Z-domain (■) and the random-orientation (●), respectively. This result showed that 10-fold lower concentration of antibody was required for the detection of the analyte (HRP) at the same concentration by orientation control than the conventional ELISA. As mentioned previously, it is also resulted from the orientation control by the Z-domain. The maximum difference of assay result was observed at the antibody concentration of 450 nm as FIG. 5 (c). When the microplate was coated with anti-CRP antibodies at this concentration, the limit of detection was estimated to be 1.5 ng/ml and 25 ng/ml for the orientation controlled antibody layer and the randomly oriented antibody layer, respectively. As shown in FIG. 5 (d), the limit of detection as well as response at saturation of the microplate with controlled orientation were far highly estimated in comparison to the microplate with randomly oriented antibody layer. Such an improvement of sensitivities represented the increase of the binding sites by the orientation control effect of the autodisplayed Z-domain. From the negative control experiment by using outer membrane layer from intact E. coli, the non-specific binding of proteins was estimated to be nearly baseline level until the response from positive control experiment reached the saturated level.

These results shows that the new immunoassay based on the outer membrane layer with autodisplayed Z-domain could be applied for immunoassays requiring very lower limit of detection and higher sensitivity than the conventional ELISA without orientation control of antibodies.

1.3.4 Conclusions

A new immunoassay with orientation controlled antibody is presented for highly sensitive detection of analyte by using a microplate coated with E. coli outer membrane. The Z-domain with IgG binding activity was expressed on the outer membrane of E. coli as a fusion protein, and then the outer membrane of E. coli was isolated by using lysozyme reaction and sequential centrifugation steps. The IgG binding activity of the outer membrane layer on the microplate was linearly correlated to the hydrophobicity of the microplate surface, and the formation of E. coli outer membrane layer through hydrophobic interaction could be demonstrated by using microplates with controlled hydrophobicity. By using the outer membrane coated microplate, a new immunoassay was presented by using HRP as a model analyte. In comparison to the conventional immunoassay with randomly oriented antibody layer, the new immunoassay could achieve far improved the limit of detection as well as sensitivity through the improved orientation control of antibody layer The applicability of the new immunoassay for medical diagnosis was demonstrated by the detection of C-reactive protein (CRP) which is known to be a biomarker protein for inflammatory diseases. From these results, the feasibility of the new immunoassay with orientation controlled antibody layer by using autodisplayed Z-domain was demonstrated for the detection requiring far higher sensitivity and lower limit of detection than the conventional immunoassay based on microplates.

Example 2

E. coli Outer Membrane with Autodisplayed Z-Domain as a Molecular Recognition Layer of SPR Biosensor The immunoaffinity (IA) biosensors utilize the highly selective binding affinity of antibodies for the molecular recognition of a target analyte in a complex mixture such as serum. For the sensitive detection of a target analyte at a very low concentration, the antigen binding sites ($F_{ab}$ region) of antibodies should be directed to the analyte solution ('orientation control') and the antibodies should be immobilized with an high density ('density control'). In this work, the Z-domain of protein A was expressed as a recombinant-fusion protein on the outer membrane of E. coli by using "Autodisplay" technology. The outer membrane of E. coli with autodisplayed Z-domain was isolated and then layered on various hydrophobic surfaces including the surface of gold. The effect of orientation control of antibodies was demonstrated by binding capacity of the labeled antibodies. These results indicated that the antibody-layer based on the outer membrane layer has a significantly larger number of analyte binding sites at the same unit area in comparison to the antibody-layer by physical adsorption. To test the feasibility of IA biosensors, the OM layer was formed on the SPR biosensor surface, and the detection of C-reactive protein (CRP) and hIgG was demonstrated. From these experiments, the LOD of SPR biosensor was estimated to have improved more than 100-fold compared to the SPR biosensor with the antibody-layer by physical adsorption.

2.1 Introduction

We expressed Z-domain of protein A on the surface of the outer membrane of E. coli by using "Autodisplay" technology. The autodisplayed Z-domain was analyzed to have the IgG-binding activity by using fluorescence labeled antibodies (IgG's). The ratio of E. coli with active Z-domain was estimated to be over 95% by using FACS analysis. Such E. coli with autodisplayed Z-domain could be applied to the sandwich-type immunoassay as a signal amplifier of SPR biosensor for the improvement of the sensitivity.

In principle, the autodisplayed proteins on the outer membrane of E. coli always have the same structures as well as orientation, if only it is expressed by the autodisplay system. Furthermore, the number of autodisplayed Z-domain on the outer membrane was estimated to be quite high from the SDS-PAGE analysis in comparison to the other proteins on the outer membrane of E. coli. Therefore, if the outer membrane could be layered on the surface of transducers, the orientation control as well as the density control of antibodies, which is necessary insignificantly improving the sensitivity of biosensors, can be achieved.

For the real application of outer membrane as biosensors, the thickness of molecular recognition layer on the transducer surface should be restricted for sensitive detection of a target analyte. Especially the biosensors based on the evanescence field, such as surface plasmon resonance (SPR) biosensor, the thickness of sensitive layer is usually less than a few hundred nanometers and the molecular recognition layer should be far thinner than the thickness of the sensitive layer for the detection of analytes (Homala, 2006). Therefore, the applicability of outer membrane layer to biosensors should be estimated by monitoring the whole sensing process from the outer membrane layer formation step to the analyte binding step.

In this work, the layer formation of the E. coli outer membrane is presented on the transducer surface by using different surfaces with controlled hydrophobicity. The effect of orientation control and density control of antibodies by the outer membrane with Z-domain on the transducer was estimated in comparison to antibody-layers prepared by the conventional adsorption method. For the feasibility test for SPR biosensors, C-reactive protein (CRP) and hIgG detection was demonstrated.

2.2 Materials and Methods 2.2.1 Materials

Anti-CRP antibodies (polyclonal), anti-mIgG antibodies labeled with fluorescein (polyclonal), anti-mIgG antibodies labeled with FITC (polyclonal), anti-mIgG antibodies antibodies, hIgG, anti-mIgG antibodies labeled with HRP (polyclonal), anti-hCG antibodies conjugated with 40 nm gold nano particles (monoclonal) and purified CRP were bought from AbCam (Cambridge, UK). Phenylmethanesulfonyl fluoride and Aprotinin were purchased from Roche Korea (Seoul, Korea). Bovine serum albumin (BSA), lysozyme, DNase, HRP and all of the other chemicals (of analytical grade) were purchased from Sigma-Aldrich Korea (Seoul, Korea).

2.2.2 Culture of E. coli with autodisplayed Z-domain

The vector for autodisplay was constructed by the cloning of the antibody binding Z-domain from S. aureus with PCR amplification as described in the previous work. E. coli cells were routinely cultured at 37° C. in Luria-Bertani (LB) broth of 10 μM EDTA, 10 mM 2-mercaptoethanol and ampicillin at the concentration of 100 mg/l. For the activity assay, E. coli cells transformed with the plasmid pET-Z-18-3 were grown overnight and diluted 100-fold in a freshly prepared medium. The E. coli cells were grown at 37° C. with vigorous shaking until the optical density (OD) reached 3.0 at the wavelength of 578 nm. After the E. coli cells were harvested, they were washed three times with PBS and then resuspended in PBS to a final optical density of 1.0 at the wavelength of 578 nm.

2.2.3 Preparation of OM particle

After the cultured E. coli cells were resuspended in 0.2 M Tris/HCl buffer, the following reagents were added for the lysozyme reaction: 1 M Sucrose, 10 mM EDTA, lysozyme solution at the concentration of 10 mg/ml. The cells treated with lysozyme were incubated at room temperature for 10 min. To quench the lysozyme reaction, 100 mM PMSF (Phenylmethanesulfonyl fluoride in Isopropanol) and aprotinin at the concentration of 10 mg/ml in 10 nM HEPES (pH 8.0) were added. Then, for the OM particle preparation, extraction buffer (2% Triton X-100, 50 mM Tris/Hcl, 10 mM $MgCl_2$) and DNAse at the concentration of 1 mg/ml were added to the E. coli cells and then placed on ice for 25 minutes. The E. coli cells were centrifuged with 6000 rpm for 5 min afterwards. After centrifugation, the supernatant were transferred to a new centrifugation tube and centrifuged again with 20000 rpm for 10 min. After washing step, the OM particle was resuspended in PBS (Hantke, 1981; Schultheiss et al., 2002).

2.2.4 SPR Measurement

A Spreeta™ chip from Texas Instruments Co. (Dallas, Tex.) was used for the SPR measurements. This SPR chip is equipped with a flow cell with a capacity of 5 µl and the measurements were performed using a home-made control circuit board, which is designed according to the technical specification of Spreeta™ chip from Texas Instruments Co. In each case, the sample and the washing solution were injected into the flow cell using an integrated injection valve and a peristaltic pump. The pumping rate was set at 1.0 ml/min and the flow of the solution was programmed to stop during the incubation step. The whole instruments were kept in an incubator where the temperature was set at 37° C. Each measurement step consists of sample injection (100 µl), incubation (30 min), and three repeated washing steps with 0.5% (v/v) Tween 20 (3 ml). In order to avoid any effect due to the change of buffer, the signal was calculated as the difference between SPR response prior to sample injection and that after the washing step. The flow of buffer was stopped during the measurement and the incubation steps (Jeon and Pyun, 2008).

2.3 Results and Discussion
2.3.1 Formation of OM Layer

The OM particle was prepared by the hydrolysis of the peptidoglycan layer using lysozyme. OM particles have hydrophilic surface composed of lipopolysaccharide (LPS) in order to interact with the aqueous environment, and the core part of OM particles may contain hydrophobic lipoproteins and peptidoglycans. The structure of the outer membrane is for instance described by Hiroshi (1996).

In the case of the outer membrane particle, the core part makes interaction with the hydrophobic surface, and the outer side of OM particle, which is hydrophilic, is directed to the aqueous environment in the OM layer.

In the case of E. coli with autodisplayed Z-domain, the beta-barrel protein is buried in the outer membrane and the Z-domain is translocated to the cell surface by passing through the beta-barrel during autodisplay process (Jose, 2006, 2007). Therefore, the Z-domain is located at the surface of the OM particle and is directed to the aqueous side when the outer membrane layer is formed on the hydrophobic transducer surface.

To observe the OM layer formation on the hydrophobic surface, the OM particle was treated to differently modified surfaces with controlled hydrophobicity. The contact angles of the commercially available microplates called Maxisorp, Polysorp, Multisorp, Medisorp from Nunc Co (USA) was estimated to be 64.8°, 77.6°, 44.7°, 66.7°, respectively. The contact angle was determined by the sessile drop method by a contact angle goniometer DSA100B (Krüss GmbH, Hamburg, Germany). Briefly, the contact angle was measured by dropping 5 µl of distilled water and analyzing the side image was by using angle-measurement software Image J. For the OM layer formation these microplates were treated to the OM particle with Z-domain along with another OM particle from intact E. coli (negative control). In order to compare the OM formation on the surfaces with different hydrophobicity, antibodies labeled with HRP were treated, and then the chromogenic reaction of HRP was performed with TMB.

As shown in FIG. 6, the most hydrophobic surface of Polysorp showed the highest chromogenic signal which means that the OM layer on the Polysorp surface had the most dense distribution of Z-domains for the binding of HRP-labeled antibodies (Josephy et al., 1982). The OM layer formed by the particles from the intact E. coli (negative control) showed no comparable the chromogenic reaction signal, which means that the level of non-specific binding of the HRP-labeled antibodies was negligible. If the OM layer was not formed on the surface of microplates, the non-specific binding should have occurred at the exposed surface of the microplate, and a comparable chromogenic signal should have been observed. From these results, the hydrophobic surface is determined to be effective for the formation of OM layer by using OM particles.

Usually, biosensors have used the surface of gold for the preparation of molecular recognition layer, that is, for the immobilization of biomolecules such as enzymes, antibodies, etc. Especially, the IA biosensors based on SPR transducers, capacitive transducers, mass sensitive transducers such as QCM, SAW, FPW have been most frequently used the gold's surface for the immobilization of antibodies (Park et al., 2000; Kurosawa et al., 2004; Stubbs et al., 2002; Wessa et al., 1999; Chang et al., 2008; Huang and Lee, 2008). Such a preference for the gold's surface was originates from the easy preparation of self-assembled monolayer (SAM) on the surface by using thiolated hydrocarbons (Chung et al., 2006b). SAM has supplied a large amount of homogeneous monolayer of hydrocarbons with functional groups such as carboxylic acid and hydroxyl groups, which can be used for the covalent immobilization of biomolecules. For the transducers based on evanescence field, as SPR and mass sensitive biosensors, the thickness of molecular recognition layer is very critical for their sensitivity because the height of the sensitive layer was reported to be less than 200 nm (Homola, 2006).

The OM layer formation was tested on the surface of gold for the application to biosensors. As the surface is also quite hydrophobic with a contact angle of approximately 70°, the OM layer was expected to be formed by the same procedure with OM particle treatment. As shown in FIG. 7, the OM particles with Z-domain and the OM particles from intact E. coli (negative control) were treated on the gold's surface. Then, fluorescein-labeled antibodies were treated to each surface. The gold's surface coated with BSA was also tested with fluorescein-labeled antibodies.

As shown in FIG. 7, the OM layer prepared with the OM particle with Z-domain shows a strong green fluorescence signal after the treatment with the fluorescein-labeled antibodies. However, the OM layer prepared from the intact E. coli (negative control) shows no significant fluorescence signal, and the BSA coated gold's surface also shows no significant fluorescence signal.

These results imply that OM layer can be formed on the surface of gold and the autodisplayed Z-domain has IgG-binding activities. Same as in the case of microplate experiments, the non-specific binding of antibodies could be prevented by using OM layer from intact E. coli without Z-domain.

For the observation of surface morphology, AFM analysis of the OM layer on the gold's surface was performed before and after the treatment of antibodies. As shown in FIG. 8, the surface of bare gold was analyzed at an area of 10 µm×10 µm. Then, the OM layer with Z-domain on the gold surface was analyzed, and then antibodies (IgG) were treated to the OM layer. Compared with the pure gold's surface, the OM layers before and after the antibody treatment have significantly different surface morphologies (see also FIG. 26). When secondary antibody was additively treated to the OM layer, which is already bound with the pre-treated antibodies, showed far larger structures in the shape of an iceberg were observed at the surface.

Although these AFM images can not give a precise explanation on the events between OM and antibodies, the morphological change after the OM layer formation is obviously observed. The AFM images show the interaction between antibodies and the OM layer. In addition, the thickness of OM layer is estimated to be less than 100 nm and the OM layer was expected to be applicable to the previously mentioned biosensors based on evanescence field for the detection of a target analyte.

2.3.2 Effect of Orientation Control By OM Layer

The OM layer with Z-domain aims to improve the sensitivity of the immunoassay with biosensors, which is realized by the orientation and the density controls of the antibodies for the detection of a target analyte. To evaluate these effects, the immunoassay was carried out by using two kinds of IA layers: the antibody-layer of OM layer with Z-domain and the antibody-layer by physical adsorption. The C-reactive protein (CRP) was used as a target analyte and anti-CRP antibodies at the same concentration of 0.5 µg/ml were treated for both IA layers. Then, the immunoassays were carried out according to the conventional ELISA procedure: After the CRP samples with known concentrations were treated to both IA layers, the amount of bonded CRP was evaluated by using HRP-conjugated secondary antibodies and TMB solution. After quenching with 2 M sulfuric acid, the OD value of the TMB solution was measured by ELISA reader at the wavelength of 450 nm.

The immunoassays by using the antibody-layer of OM layer with Z-domain (■) and the antibody-layer by physical adsorption (●) were performed by using CRP samples at the concentration range of 0.1 ng/ml-200 ng/ml as shown in FIG. 9. FIG. 28 presents an example of SPR recordings. The limit of detection (LOD) was evaluated as the concentration where the response is three times higher than that of the standard deviation from the baseline response by a blank sample (Ezan and Jacques, 2000). In the use of the antibody-layer of OM layer with Z-domain (■) and the antibody-layer by physical adsorption (●), the LOD was calculated to be approximately 1.5 ng/ml and 25 ng/ml, respectively. This result shows that the LOD of the antibody-layer of OM layer with Z-domain (■) was 15-fold more sensitive than the antibody-layer by physical adsorption (●), which indicates that the antibody-layer of OM layer with Z-domain (■) has a significantly larger number of analyte binding sites at the same unit area than the antibody-layer by physical adsorption (●). The analyte binding site represents the well-oriented antibodies suitable for the analyte binding, which were made by the orientation and density control of the anti-CRP antibodies by the Z-domains.

Usually, a saturated response at a certain analyte concentration is found at the response curve of immunoassays (Ezan and Jacques, 2000). The antibody-layer of OM layer with Z-domain (■, OD unit: 0.25) shows far higher saturation response than the antibody-layer by physical adsorption (●, OD unit: 0.02) as shown in FIG. 9. This result shows that the OM layer with Z-domain has far higher binding capacity at the unit area in comparison to the antibody-layer by physical adsorption.

The OM layer without Z-domain (negative control) shows no significant non-specific binding after the treatment of antibodies as well as CRP samples. Since non-specific binding of unrelated proteins may result in a false positive signal in immunoassays, it should be reduced as low as possible (Ezan and Jacques, 2000). Usually, the hydrophilic surfaces are known to reduce the non-specific binding of proteins for immunoassay (Silin et al., 1997). In the case of E. coli, the outer membrane is known to be negatively charged (Hamadi et al., 2008). Actually, the zeta-potential of intact E. coli (negative control) and the E. coli with autodisplayed Z-domain were measured to be −22.0 mV, −21.5 mV, respectively. Therefore, the significantly low non-specific binding of the OM layer without Z-domain (negative control) can be explained as a consequence resulted from the hydrophilicity of the E. coli's outer membrane.

2.3.3 SPR measurement with OM layer as molecular recognition layer

As previously mentioned, the biosensors based on evanescence field have a sensitive layer with a thickness of less than 200 nm. Therefore, the biosensor will not be sensitive as it had been any more when the molecular recognition layer is as thick as the sensitive layer. For the feasibility test for SPR biosensor, the OM layer with Z-domain was prepared on the gold's surface of SPR biosensor, and then the antibodies against CRP were sequentially treated. As shown in FIG. 10, the SPR signal was monitored during the whole sensing process from the outer membrane layer formation step to the analyte binding steps.

When the OM particle was injected, the SPR signal was observed to have increased significantly increased during the incubation step as shown in FIG. 10 (a). After the washing step, the SPR signal by the OM layer preparation was calculated to be 2.3 (A.U). Then, the anti-CRP antibodies were treated and the SPR signal was calculated to be 1.1 (A.U). These results illustrates that the SPR signal could be monitored during the OM layer formation and during the followed immobilization step of antibodies, which indicates that the sensitive layer of SPR biosensor was not saturated by the OM layer with Z-domain. This result is coincident to the thickness estimation of the OM layer by AFM analysis.

For the demonstration of orientation control, another SPR biosensor with the antibody-layer by physical adsorption of the anti-CRP antibodies was prepared. Standard CRP samples were prepared in bovine serum and injected to both biosensors. As shown in FIG. 10 (b), the SPR biosensor with OM layer shows sensor response by the injection of CRP sample at the concentration of 100 ng/ml, 1 µg/ml and 10 µg/ml. These results mean that the LOD of OM layered SPR biosensor was estimated to be less than 100 ng/ml.

In the case of SPR biosensor with the antibody-layer by physical adsorption of anti-CRP antibodies, no measurable SPR signal was detected by the injection of the above three standard CRP sample. This means that the LOD of the SPR biosensor with the antibody-layer by physical adsorption is estimated to be more than 10 µg/ml. From the simple comparison, the LOD of SPR biosensor with OM layer with Z-domain is more than 100-fold sensitive than with the antibody-layer by physical adsorption. Such difference in LOD's can be explained by the orientation and density control effects of the Z-domain on OM layer. As in the case of microplate assay, the OM layer with Z-domain supplied more binding sites than the antibody-layer by physical adsorption and the significant improvement of the sensitivity of SPR biosensor was achieved.

As another demonstration of the orientation and density control effects of the OM with Z-domain, SPR biosensor with anti-hIgG antibodies were prepared by using the OM layer with Z-domain. The sensitivity was compared with another SPR biosensor with the antibody-layer by physical adsorption of the same antibody. As shown in FIG. 11, the LOD of SPR biosensor with OM layer was estimated to have been improved more as much as 200-fold compared to the SPR biosensor with the antibody-layer by physical adsorption. These results can be also explained by the exceeding number of binding sites for the analyte, which was supplied from the orientation and the density control effects of the OM layer with Z-domain.

2.4 Conclusions

The immunoaffinity (IA) biosensors utilize the highly selective binding affinity of antibodies for the molecular recognition of a target analyte in a complex mixture such as serum. For the sensitive detection of a target analyte at a very low concentration, the antigen binding sites ($F_{ab}$ region) of antibodies should be exposed to the analyte solution ('orientation control') and the antibodies should be immobilized with an high density ('density control'). In this work, the Z-domain of protein A was expressed as a recombinant-fusion protein on the outer membrane of E. coli by using "Autodisplay" technology.

Such outer membrane of E. coli with autodisplayed Z-domain was isolated and then layered on various hydrophobic surfaces including gold's surface. The effect of orientation control of antibodies was demonstrated by binding capacity of labeled antibodies. The OM layer prepared with the OM particle with Z-domain shows a strong green fluorescence signal after treated with the fluorescein-labeled antibodies, whereas the OM layer prepared from intact E. coli (negative control) shows no significant fluorescence signal. From these results the OM layer with Z-domain was determined to have been effectively layered on the gold's surface. AFM analysis showed the interaction between antibodies and the OM layer, and the thickness of OM layer was estimated to be less than 100 nm. For the evaluation of these effects, the immunoassay was carried out by using the antibody-layer of OM layer with Z-domain and the antibody-layer by physical adsorption, and the LOD was calculated to be approximately 1.5 ng/ml and 25 ng/ml, respectively. These results indicate that the LOD of OM layer can improve the sensitivity up to 15-fold than the antibody-layer by physical adsorption and that the OM layer with Z-domain has a significantly larger number of analyte binding sites at the same unit area by the orientation control effect of Z-domain. For the feasibility test for IA biosensors, the OM layer was formed on the SPR biosensor surface, and the detection of C-reactive protein (CRP) and hIgG was demonstrated. From these experiments, the LOD of SPR biosensor was estimated to have improved as much as 100-fold in comparison to the SPR biosensor with the antibody-layer by physical adsorption.

Example 3

Hyper Sensitive Capacitive Biosensor by Using E.coli Outer Membrane Layer with Autodisplayed Z-Domains A highly sensitive capacitive biosensor was developed by using E.coli's outer membrane (OM) layer with autodisplayed Z-domains which improves the sensitivity of the conventional immunoassays through the orientation control of antibodies. The electric isolation of the OM layer was tested using cyclic voltammetry and impedance spectroscopy, which are required for capacitive measurement from non-faradaic current. The applicability of OM layer for the capacitive biosensor was demonstrated by detecting horseradish peroxidase and C-reactive protein. The limit of detection (LOD) of the capacitive biosensors based on the OM layer was estimated to be 10-fold higher than the conventional capacitive biosensors based on self-assembled monolayer (SAM).

1. Introduction

The capacitive biosensors based on the interaction of highly specific antigen-antibody have been the field of interest because of the high sensitivity and relatively simple instrumentation [Mirsky et al., 1997; Berggren et al., 1998; Berggren et al., 1999; Berggren et al., 2001; Dijksma et al., 2001; Bard et al., 2001; Bart et al., 2005. Since the capacitive signal is usually measured from the non-faradaic current after appling electric pulses, the faradaic current through a redox reaction at the electrodes should be avoided by using an electric isolation layer [Berggren et al., 1998; Berggren et al., 1999; Berggren et al]. Additionally, the electric isolation layer should be as thin as possible for a sensitive capacitive measurement. [Hu et al., 2005; Li et al., 2005; Wu et al., 2005; Fu et al., 2007]. Therefore, the antibody (or antigen) layer of a capacitive biosensor should be prepared as thin as possible with the ability to maintain the electric isolation with the sample solution. From these requirements, the self-assembled monolayer (SAM) [Berggren et al.,1998; Berggren et al.,1999; Berggren et all as well as various other chemical layers were applied to the capacitive biosensors, such as o-aminobenzenthiol oligomer layer [Hu et al., 2005; Hu et al., 2002], electropolymerized layers [Li et al., 2005; Wu et al., 2005; Fu et al., 2007], plasma-polymerized ethylenediamine [Li et al., 2004], electrodeposited hydroxyapatite [Yang et al., 2005], and molecularly imprinted sol-gel films [Yang et al., 2005, Zheng et al., 2006].

Examples 1 and 2 demonstrate that the outer membrane (OM) layer with autodisplayed Z-domains could improve the sensitivity of conventional immunoassays through the orientation control of the immobilized antibodies.

In this example, a hyper sensitive capacitive biosensor is presented by using the OM layer with autodisplayed Z-domains to immobilize antibodies. As the first step, the feasibility was tested for the capative measurement by analyzing the electrochemical properties of the OM layer with cyclic volatammetry and impedance spectroscopy. Then, the detection of horseradish peroxidase (HRP) and C-reactive protein (CRP) [Nader et al., 2002] was demonstrated by using the capacitive biosensor based on the OM layer.

2. Materials and Methods

2.1 Materials

C-reactive protein (CRP) and anti-CRP antibodies (polyclonal) were purchased from AbCam (Cambridge, UK). Bovine serum albumin (BSA), horseradish peroxidase (HRP), anti-HRP antibodies (polyclonal), mercaptoundecanoic acid, N-(3-dimethylaminopropyl)-N'-ethylcarbodiimide (EDC), N-hydroxysuccinimide (NHS) and all of the other chemicals in analytical grade were bought from Sigma-Aldrich Korea (Seoul, Korea).

2.2 Electrode Preparation and Instrumentation

The working and the counter electrode with a gold layer (100 nm thick) was made on a highly P-doped silicon wafer (<10 mΩ·cm) by RF-sputtering. Then, the wafer was cut into electrodes with an area of 5×10 mm² by using a wafer sawing system from Disco Co (Japan). The exposed surface area of the working electrode was adjusted to be approximately 10 mm² by using a passivation layer. A flow-cell type electrode-holder with an internal volume-capacity of 20 μl was made with flexi-glass. A sintered Ag/AgCl electrode with the diameter of 1 mm and the length of 5 mm from Warner instruments (CT, USA) was integrated to the electrode-holder as a pseudo reference electrode. The working electrode and the counter electrode were combined into the electrode-holder. The liquid reagents were treated to the electrode by using a peristaltic pump and the sample was injected to the electrode by using a manual injection value from Rheodyne Co (CA, USA).

2.3 Capacitance Measurement

The chronoamperometric method was utilized to measure the capacity change resulting from the specific binding of an analyte to the electrode surface by using a commercial potentiostat from IVIUM Co (Netherlands). In this work, a potential step of 50 mV was applied to 0 V for 10 ms, and then the potential was returned to 0 V. Then, the current decay was measured for every 0.05 ms for 2 s [Bard et al., 2001;Hu et al., 2002], and the capacitance was analyzed by fitting the decaying current curve: $i(t)=u/R_s \cdot \exp(-t/R_s C_d)$, where i(t) represents the current at time t, u the amplitude of the potential pulse applied, $R_s$ the resistance of solution, $C_d$ the total capacitance measured at the electrode/solution interface, and t the time elapsed after the potential pulse was applied. To estimate the parameters, the formula was converted to have a linear relationship between ln i(t) and t as follows: $\ln i \, (t = \ln(u/R_s) + (-t/R_s C)$. From this linear correlation, the capacitance value was evaluated by extrapolating the slope and y-intercepts [Hu et al., 2005; Hu et al., 2002]. Since the immunoaffinity biosensors measure the amount of the analyte adsorbed to the immunoaffinity layer, several washing steps usually followed by incubation of the sample solution takes place in order to remove the non-specifically bound proteins. The signal was calculated as the difference with the previous measurement.

2.4 Preparation of Immunoaffinity Layer

The Z-domain was autodisplayed by using an autodisplay vector constructed as described in Example 1. The OM particle with autodisplayed Z-domains was isolated and the OM layer was prepared on the gold electrode as described in Example 1. The antibodies (10 μg/ml) were immobilized to the OM layered electrode through incubation for 1 hr at room temperature. The SAM was prepared on a gold surface by incubating 10 mM mercaptoundecanoic acid solution in ethyl alcohol overnight. Then, the anti-HRP antibodies were immobilized by reacting EDC and NHS. The unreacted functional groups were blocked by treating 10 mM ethylenediamine for 30 min.

3. Results and Discussion 3.1 Electrochemical Properties of OM Layer

In order to be applied to the measurement of non-faradaic current, the OM layer is required to have an electric isolation. In this work, the feasibility the OM layer with Z-domains was analyzed by using cyclic voltammetry (CV) and impedance spectroscopy analysis [Hu et al., 2005; Li et al.,2005; Wu et al., 2005; Fu et al., 2007; Hu et al., 2002; Li et al., 2004].

As shown in FIG. 27, the outer membrane layer coating a surface achieves electric isolation. As shown in FIG. 12(a), CV diagrams with the redox peaks were obtained by using 10 mM $Fe(CN)_6^{3-/4-}$ as a redox couple. As the concentration of the OM particles increased, the area of the CV diagram was observed to decrease, and the redox peaks disappeared at the concentration higher than 1 mg/ml. The total charge transfer was calculated by integrating the CV diagram to be 20.9 mC, 11.4 mC, 5.0 mC, 1.1 mC for the treatment of OM particles at the concentration of 1 μg/ml, 10 μg/ml, 100 μg/ml, 1 mg/ml, respectively [Hamann et al., 1998]. In the case of SAM (mercaptoundecanoic acid) and physically adsorbed HRP layer, the total charge transfer was calculated to be 2.5 mC and 5.8 mC, respectively. These results show that the OM layer formed by incubating the OM particles at the concentration of 1 mg/ml could achieve far higher electric isolation compared to the conventional SAM (mercaptoundecanoic acid).

From the impedance spectroscopy at the frequency range of 0.1 Hz-1 MHz with an applied potential of 50 mV, Nyquist plot was obtained to calculate the charge transfer resistance from the x-cut of the hemispheric response curve as shown in FIG. 12(b). The charge transfer resistance indicated the resistance for the electrode to transfer a charge from the electrolyte through the OM layer, which was calculated to be 152.1 kOhm/mm², 190.0 kOhm/mm², 221.6 kOhm/mm², 236.5 kOhm/mm² respectively, when the OM solutions with the concentration of 1 μg/ml, 10 μg/ml, 100 μg/ml, 1 mg/ml were treated. In the case of SAM of mercaptoundecanoic acid, the charge transfer resistance was measured to be 214.3 kOhm/mm², which is a value high enough to measure the non-faradaic current bychronoamperometry [Hu et al., 2005; Li et al., 2005; Wu et al., 2005]. These results also show that the OM layer could achieve higher electric isolation than the conventional SAM (mercaptoundecanoic acid).

The optimum incubation time of the OM particle solution for the OM layer formation was also determined by CV analysis. As shown in FIG. 12 (c), the integrated area of CV diagram was observed to change according to the incubation time of the OM particle solution at the concentration of 1 mg/ml. The total charge transfer for the OM layers was calculated to be 14.2 mC, 1.3 mC and 0.6 mC when the OM particles was treated for 1 hr, 2 hrs, 3 hrs, respectively. From this CV analysis, the optimum treatment time was calculated to be 2 hrs at which the redox peaks were not observed.

3.2 Capacitive Measurement of Affinity Binding to OM Layer

In this Example, the antibody layer was prepared to the autodisplayed Z-domains at the OM layer for the capacitive measurement of the analyte concentration (see Example 1). As demonstrated in Examples 1 and 2, such OM layers with autodisplayed Z-domains could significantly increase the sensitivity of immunoassay through the orientation control of antibodies.

To compare the orientation control effect of autodisplayed Z-domains, randomly-oriented antibody layers were also prepared by physical adsorption and SAM of mercaptoundecanoic acid as shown in FIG. 13. The physically adsorbed antibody layer was produced by incubating antibody solution on the gold electrode. In the case of SAM, the antibodies were immobilized through covalent bonding by using the coupling reagents EDC/NHS [Mirsky et al., 1997; Berggren et al.,1998; Dijksma et al., 2001]. The immobilization of antibodies to the autodisplayed Z-domains were carried out at the optimum conditions determined in Examples 1 and 2. The OM layer from intact *E.coli* was used as a negative control to measure the non-specific binding of proteins. As the first step, the electric isolation of each antibody layers was evaluated from the charge transfer resistance to be 263.51 kohm/mm², 314.30 kohm/mm² and 410.34 kohm/mm² for the antibody layers of physical adsorption, SAM and OM layer with Z-domains, respectively. These results show that the electric isolation by the OM layer with immobilized antibodies has higher electric isolation than the conventional antibody layers.

The capacitive measurement was performed by using HRP as a model analyte, and anti-HRP antibodies were immobilized on the gold electrode by bonding to the autodisplayed Z-domains on OM layer. As shown in FIG. 13, the LOD was estimated to be 10 pg/ml, 1 pg/ml and 100 fg/ml for the antibody layers by physical adsorption, SAM, and OM layer with Z-domains, respectively. These results indicate that the LOD has been improved 10-fold by using the OM layer with autodisplayed Z-domains compared to the capacitive biosensor based on SAM. The sensitivity of this capacitive biosensor was also observed to have improved at each analyte (HRP) concentration in comparison to the capacitive biosensor based on SAM.

The capacitive biosensors were applied to detect C-reactive protein (CRP) which was reported to be an early biomarker for various inflammatory diseases [Nader et al., 2002]. The capacitive biosensors were prepared by immobilizing anti-CRP antibodies. As shown in FIG. 14, the sensitivity of the capacitive biosensor based on the OM layer with Z-domains was observed to have improved at each CRP concentration in comparison to the capacitive biosensor based on the SAM electrode. The LOD was estimated to be 100 pg/ml, 10 pg/ml and 1 pg/ml for the capacitive biosensors based on physically adsorbed antibody layer, SAM and OM layer with Z-domains, respectively. These results show that the OM layer with Z-domains can significantly improve the sensitivity of the capacitive biosensor through the orientation control of antibodies.

Conclusions

A highly sensitive capacitive biosensor was developed by using E.coli outer membrane (OM) layer with autodisplayed Z-domains. As illustrated in the Examples 1 and 2, OM layer with autodisplayed Z-domains could improve sensitivity of immunoassays through the orientation control of the immobilized antibodies. In this Example, the electric properties of the OM layer were tested to be feasible for the capacitive measurement by cyclic voltammetry and impedance spectroscopy. By using horseradish peroxidase (HRP) as a model analyte, the limit of detection (LOD) was estimated to be 100 fg/ml which shows a 10-fold improved LOD in comparison to the capacitive biosensor with antibody layers immobilized to SAM. The LOD of the detection of C-reactive protein (CRP) was also 10-fold improved compared to the capacitive biosensor using SAM. These results demonstrate that the OM layer with Z-domains could significantly improve the sensitivity of the capacitive biosensor through the orientation control of antibodies.

Example 4

Autodisplay of Streptavidin

Streptavidin was expressed on the outer membrane of E.coli as a recombinant fusion protein with an autotransporter domain called AIDA-I (adhesin involved in diffuse adherence) by using autodisplay technology. The autodisplay of streptavidin was confirmed by SDS-PAGE of the outer membrane proteins, and the number of autodisplayed streptavidin molecules on a single E.coli cell was evaluated by using densitometric analysis. The biotin-binding activity of the autodisplayed streptavidin was estimated after treatment of fluorescence labeled biotins by using fluorescence microscope and flow cytometric analysis. The biotin-binding activity of the E.coli with autodisplayed streptavidins was estimated by comparing with the streptavidin immobilized magnetic beads. Finally, the outer membrane with autodisplayed streptavidins was isolated and layered on a 96-well microplate for the application to immunoassays.

1. Introduction

The autodisplay technology is a kind of surface display method of proteins or peptides to the outer membrane of E.coli. In the autodisplay technology, proteins or peptides are expressed as a fusion protein with an autotransporter domain called AIDA-I (adhesin involved in diffuse adherence) from E.coli [Benz et al., 1992]. As shown in FIG. 15, the recombinant fusion protein was made by introducing the coding sequence of passenger protein in-frame between the signal peptide and the translocating domain of the transformation vector [Maurer et al.,1997; Maurer et al., 1999]. The C-terminal part of the autotransporter protein forms a porin-like structure (β-barrel) within the outer membrane of Gram-negative bacteria, and the recombinant passenger domain was translocated to the surface through this pore [Jose et al., 1995; Jose et al., 2005; Jose et al., 2006; Jose et al., 2007]. Such autodisplay system was reported to express more than $10^5$ recombinant molecules on the outer membrane of a single E.coli cell [Jose et al., 2001].

In this Example, the autodisplay of streptavidin is presented, which is a protein with a well-known biotin-binding activity. Streptavidin is known to be a tetrameric biotin binding protein with a biotin binding sites at each subunit. The streptavidin shows unusually high affinities to biotin ($Kd=10^{13}-10^{15}$ M) and this non-covalent interaction is considered to be almost irreversible [Green et al.,1975; Green et al.,1990], and such a tight binding has been used for many in vitro and in vivo applications [Wilchek et al., 1988; Bayer et al., 1990; Chen et al., 2000; Qureshi et al., 2002; Howarth et al., 2006]. In this work, the autodisplay of streptavidin was confirmed by the analysis of outer membrane proteins with SDS-PAGE, and the number of autodisplayed streptavidin molecules on a single E.coli cell was evaluated by using densitometric analysis by comparison with a reference protein of the E.coli outer membrane called OmpA. The biotin-binding activity of the autodisplayed streptavidin was estimated after treatment of fluorescence labeled biotins by using a fluorescence microscope and flow cytometric analysis. The biotin-binding activity of the E.coli with autodisplayed streptavidins was compared with similar sized magnetic beads with covalently immobilized streptavidins. The outer membrane with autodisplayed streptavidin was isolated and layered on 96-well microplate and the biotin-binding activity was estimated to determine the applicability to immunoassays.

2. Materials and Methods

Construction of a Plasmid for the Surface Display of Streptavidin

The streptavidin gene was amplified by PCR from the plasmid pET-28a, and primers with adhesive restriction sites for XhoI and KpnI were used to make the following sequences: (forward) 5'-CTC GAG GAC CCC TCC AAG GAC TCG AAG-3' (SEQ ID NO.: 1) and (reverse) 5'-GGT ACC CTG CTG AAC GGC GTC GAG CG-3' (SEQ ID NO.: 2) (Sigma Aldrich, Munich, Germany). The PCR product (487base pairs) was first inserted into the TOPO 4.0vector (Invitrogen, Karlsruhe, Germany) according to the manufacturer's guide. Then, the insert was excised by KpnI and XhoI (New England Biolabs, Frankfurt, Germany) and it was confirmed by agarose gel electrophoresis. The fragments encoding streptavidin were extracted from the gel (Qiaquick Gel Extraction Kit, Qiagen, Hilden, Germany), and then ligated into the plasmid pET-ADX-04which was restricted by XhoI/KpnI [Jose et al., 2002]. To avoid religation of pET-ADX-04,Bgl II was added to the ligation mixture in order to cut the gene fragment encoding Adx. The plasmid was finally verified by DNA sequence analysis and was named to be pST001.

Surface Display of Streptavidin

The plasmid pST001 was transformed to E.coli UT5600 (DE3) (F−, ara-14, leuB6, secA6, lacY1, proC14, tsx-67, Δ (ompT-fepC) 266, entA403, trpE38, rfbD1, rpsL109 (Str$^r$), xyl-5, mtl-1, thi-1) (Jose et al., 1996) by electroporation. E.coli UT5600 (DE3) pST001 cells were routinely grown overnight at 37° C. and continuously shaken (200 rpm) in Lysogeny-Broth-medium (LB-Medium) containing carbenicillin having the concentration of 50 mg/l. Cells were grown until the optical density of 0.5 at the wavelength of 578 nm ($OD_{578\,nm}$ 0.5) was reached. Protein expression was induced by treatment of 1 mM IPTG and subsequent incubation for 1 h at 30° C. with vigorous shaking (200 rpm) [Maurer et al., 1997].

Flow Cytometric Analysis

E.coli UT5600 (DE3) pST001 and E.coli UT5600 (DE3) were routinely grown as described above. For the flow cytometric analysis, protein expression started at the E.coli concentration of $OD_{578nm}$ 0.3-0.4, and 1 ml of the culture was harvested. After the following washing steps, 1) 5% bovine serum albumin (BSA) in PBS, and then 2) two times washing with PBS and resuspended in 100 µl PBS, 15 mM biotinylated fluorescein solution (2 µl) was treated (Sigma Aldrich, Munich, Germany). After repeating the washing steps twice with PBS, the solutions were filtered. For each FACS analysis, 50,000 cells were analysed with a flow cytometer at the excitation wavelength of 496 nm (Cyflow, Partec, Münster, Germany).

Outer Membrane Preparation

The outer membrane of E.coli cells were prepared as described in Example 1. The E.coli cells were grown overnight and this culture (1 ml) was used to inoculate fresh LB medium (20 ml). The E.coli cells were incubated at 37° C. with vigorous shaking (200 rpm) for about 5 hr until $OD_{578\ nm}$ 0.5 was reached. Then, the E.coli cells were harvested and the outer membranes were prepared according to the rapid isolation method of Hantke [Hantke et al., 1981], using modifications by Schultheiss et al., 2002.

SDS-PAGE and Densitometric Analysis

The outer membrane protein was analyzed by using 12.5% SDS-PAGE. After electrophoresis, proteins were visualized by staining with Coomassie brilliant blue, and the density of each band was estimated using a documentation system (ChemiDoc XRS™) and an analysis program (Quantity-One™) from BioRad Laboratories.

3. Results and Discussion 3.1 Autodisplay of Streptavidin

The number of autodisplayed streptavidin molecules per E.coli cell was calculated from SDS-PAGE of outer membrane proteins as shown in FIG. 16. As expected from the specification of the E.coli strain of UT5600 (F− ara14 leuB6 azi-6 lacY1 proC14 tsx-67 entA403 trpE38 rfbD1 rpsL109 xyl-5 mtl-1 thi1, ΔompT-fepC266), the protein bands of autodisplayed streptavidin did not appear as shown in lane 1. In the case of the UT5600(DE3) transformed with the autodisplay vector pST001, the protein band of autodisplayed streptavidin with a molecular weight (69.2 kDa) was observed as shown in Lane 2. As the expression level of the outer membrane protein called OmpA of the E.coli strain of UT5600 is known to be approximately $10^5$ copies per an E.coli cell [Koebnik et al., 2000], the number of the autodisplayed streptavidin molecules were evaluated by normalizing the intensity of protein bands in the SDS-PAGE gel. From such densitometric calculation, the number of streptavidin per E.coli cell was estimated to be $1.6 \times 10^5$ molecules/cell.

The biotin-binding activity of autodisplayed streptavidins was tested by treatment of biotinylated fluorescein. The E.coli cells at the concentration of $OD_{578}$ 1.0 (200 µl) was treated with biotinylated fluorescein at the concentration of 100 µg/ml (100 µl), and then 10 µl of the biotinylated E.coli solution was used after diluted 10-fold with PBS. As shown in FIG. 17, the E.coli with autodisplayed streptavidin showed intensive fluorescence signals, which indicated the binding of biotinylated fluorescein. In the case of intact E.coli cells, no significant fluorescence signal was observed under the fluorescence microscope. This result indicated that µthe autodisplayed streptavidins on the outer membrane of E.coli had the biotin-binding activity.

The biotin-binding activity of the autodisplayed streptavidins was also tested by flow cytometric analysis. The E.coli with autodisplayed streptavidin and the intact E.coli of UT5600 were also stained with the biotinylated fluorescein. As shown in FIG. 17, the intact E.coli cells were observed at the low fluorescence signal range. On the other hand, most of the E.coli cells with the autodisplayed streptavidin were observed at the higher fluorescence signal range than the intact E.coli cells. The ratio of the intact E.coli and the E.coli with the autodisplayed streptavidin over the level of 10 (arbitrary unit) was estimated to be less than 5% and more than 95% among total number of E.coli cells, respectively. These results meant that the yield of E.coli with the autodisplayed streptavidin was more than 95%.

3.2. Activity of E.coli Outer Membrane Layer with Autodisplayed Streptavidins

The applicability of E.coli cells with the autodisplayed streptavidins was tested as a solid support of immunoassays. The biotin-binding activity of autodisplayed strepatavidin on the outer membrane of E.coli was compared with the streptavidin coated magnetic particles with a diameter of 1 µm. A magnetic bead with amino groups on the surface (Micromod GmbH, Germany) was used for the covalent immobilization of streptavidins by reacting glutaraldehyde. Different amount of streptavidin was immobilized to the magnetic beads by treatment of the magnetic beads with different concentration of streptavidin solution. After blocking with BSA (10 mg/ml), the magnetic beads were treated with biotinylated HRP at the concentration of 1 µg/ml. For the quantification of the bound biotinylated HRP, the chromogenic substrate (TMB) was treated, and then 2 M sulfuric acid was used to quench the HRP reaction. As shown in FIG. 19 (a), the maximum activity of the magnetic beads was obtained by treatment of the magnetic beads with the streptavidin solution at the concentration of 80-90 ng/ml.

The E.coli cells with autodisplayed streptavidins were compared with the streptavidin coated magnetic beads. The amount of E.coli was adjusted to have the same total surface area as the compared magnetic beads. The E.coli cell was assumed to have a cylinderic structure with the length of 2 µm and the diameter of 1 µm [Kubitschek et al., 1990]. In this case the surface area of a single E.coli cell was calculated to be 7.85 µm². For each measurement, approximately 120 µl of E.coli solution at the concentration of $OD_{578}$ 1.0 was used, which corresponded to the surface area of a single well of a 96-well microplate (flat bottom) with 100 µl of an aqueous solution. As shown in FIG. 19 (b), the assay curve of E.coli with the autodisplayed streptavidins reached saturation at the biotinylated HRP concentration of 300 ng/ml. In the case of magnetic beads with the maximum biotin-binding activity (●) showed the saturation at the biotinylated HRP concentration of 100 ng/ml. This result implied that the E.coli with autodisplayed streptavidins had at least three-times higher surface concentration of streptavidins than the magnetic bead of the maximum surface concentration of streptavidin as shown in FIG. 19(a). The relatively lower biotin-binding activity of the E.coli cells at low concentration of biotin in comparison with magnetic beads could be explained by the lower mobility of E.coli in the reaction step (by slow mixing) than the magnetic beads from (1) the relatively lower density than magnetic beads and (2) the unsymetric structure of E.coli cells. Therefore, the possibility for the surface bound streptavidins to meet biotin in the solution was expected to be relatively lower for E.coli cells than the magnetic beads.

In Examples 1 and 2, it is demonstrated that the outer membrane of *E.coli* can be separated and layered on a microplate with the conserved orientation of outer membrane by using hydrophobic interactions. In this Example, the outer membrane with autodisplayed streptavidins was also prepared as described in Example 1, and the outer membrane layer was prepared on a 96-well microplate by incubating the separated outer membrane solution at the concentration of $OD_{578}$ 1.0 for 3 hrs at room temperature. The biotin-binding activity of the outer membrane layer with autodisplayed streptavidins was estimated by treatment of biotinylated HRP, followed by the chromogenic reaction of TMB. As shown in FIG. 20, the outer membrane layer with autodisplayed streptavidins showed a dynamic range of biotin-binding activity from 1 ng/ml to 300 ng/ml. This range was very similar value to that of the *E.coli* cell based assay in FIG. 19 (*b*). The outer membrane layer of intact *E.coli* showed nearly baseline signal for the whole range of the biotinylated HRP which indicated very low, non-specific binding of proteins to the *E.coli* outer membrane.

These results show that the outer membrane layer with autodisplayed streptavidin has the biotin-binding activity as high as the streptavidin on the autodisplayed *E.coli* cells and that the outer membrane layer prepared on the microplate can be directly applied for immunoassays.

Conclusions

In this Example, the autodisplay of streptavidin was presented. For the confirmation of the autodisplayed streptavidin, the outer membrane protein was analyzed by SDS-PAGE, and the number of streptavidin molecules on a single *E.coli* cell was estimated to be $1.6 \times 10^5$ molecules/cell by using densitometric analysis. The biotin-binding activity of the autodisplayed streptavidin was estimated after treating fluorescence labeled biotins by using a fluorescence microscopy. From the FACS analysis, the efficiency of autodisplay process was evaluated to be more than 95%. The biotin-binding activity of the *E.coli* with autodisplayed streptavidins was compared with similar sized magnetic beads with covalently immobilized streptavidins. The outer membrane with autodisplayed streptavidin was isolated and layered on 96-well microplate and the biotin-binding activity was estimated to determine whether it is applicapable to immunoassays.

Example 5

Analysis of Rheumatoid Arthritis Patient Sera

Comparison of ELISA test employing anti-CRP antibodies, and a direct test according to the present invention employing carriers, as described in Example 1. Briefly, anti-CRP antibodies have been immobilized in the wells of a microplate coated with the outer membrane with autodisplayed Z domains under conditions providing orientation control, as described in Example 1.

Test sera have been obtained from 45 rheumatoid arthritis positive patients (termed 1 to 45) and 15 control patients (termed N1 to N15). In the direct test, C-reactive protein (CRP) could be detected with an improved sensitivity, compared with a standard ELISA test, as indicated by increased optical density (FIG. 23).

Example 6

Detection of S100B Protein in Cerebrospinal Fluid

S100B in cerebrospinal fluid (CSF) correlates with brain atrophy in Alzheimer disease (Petzold et al, 2003). Furthermore, patients with schizophrenia had significantly higher levels of S100B in CSF (Steiner et al., 2006). S100B is thus of value in the diagnosis of Alzheimer disease and schizophrenia.

In the present example, sensors are compared comprising IgG antibodies directed against S100B immobilized upon a bare gold surface, on SAM (mercaptoundecanoic acid), and on a surface comprising an OM layer comprising the Z domain of protein A, as described in Example 1. For control purposes a sensor comprising an OM layer without Z domains is employed.

FIG. 28 demonstrates that a sensor of the present invention provides an improved sensitivity compared with bare gold surface sensors and SAM sensors in a capacitance recording. Capacitance recording is performed as described in Example 3. The limit of detection (LOD) is improved by a factor of 10 compared with the SAM surface and a factor of 100 compared with the gold surface.

By comparison with standard sensors based upon a bare gold surface, FIG. 29 demonstrates that sensors of the present invention can successfully employed for diagnostic purposes, such as S100B determination in patient CSF. S100B concentrations obtained by the sensor of the present invention are confirmed by the standard sensor.

REFERENCES

Amit, A. G., Mariuzza, R A, Phillips, S. E., Poljak, R. J., 1986. Three-dimensional structure of an antigen-antibody complex at 2.8 Å resolution. Science 233, 747-753.

Anderson, G. P., Jacoby, M. A., Ligler, F. S., King, K. D., 1997. Effectiveness of protein A for antibody immobilization for a fiber optic biosensor. Biosens. Bioelectron. 12, 329-336.

Bae, Y. M., Oh, B. K., Lee, W., Lee, W. H., Choi, J. W., 2005. Study on orientation of immunoglobulin G on protein G layer. Biosens. Bioelectron. 21, 103-110.

Chang, W. Y., Sung, P. H., Chu, C. H., Shih, C. J., Lin, Y. C., 2008. Phase detection of the two-port FPW sensor for biosensing. IEEE Sens. J. 8, 501-507.

Chung, J. W., Park, J. M., Bernhardt, R., Pyun, J. C., 2006a. Immunosensor with a controlled orientation of antibodies by using NeutrAvidin-protein A complex at immunoaffinity layer. J. Biotechnol. 126, 325-333

Chung, J. W., Bernhardt, R. and Pyun, J. C., 2006b. Additive assay of cancer marker CA 19-9 by SPR biosensor. Sen. Actuators B Chem. 118, 28-32.

Deisenhofer, J., 1981. Crystallographic refinement and atomic models of a human Fc fragment ant its complex with fragment B of protein A from *staphylococcus aureus* at 2.9- and 2.8-Å resolution. Biochemistry 20, 2361-2370.

Deisenhofer, J., Jones, T. A., Huber, R., 1978. Crystallization, crystal structure analysis and atomic model of the complex formed by a human Fc fragment and fragment B of protein A from *staphylococcus aureus*. Hoppe-Seyler's Z. Physiol. Chem. 359, 975-985.

Ezan, E., Jacques, G., 2000. Optimization. in: Gosling, J. P. (Ed.), Immunoassays. Oxford University Press, Oxford, pp. 187-189.

Hamadi, F., Latrache, H., Zahir, H., Elghmari, A., Timinouni, M., Ellouali, M., 2008. The relation between *escherichia coli* surface functional groups composition and their physicochemical properties. Braz. J. Microbiol. 39, 10-15.

Hantke, K., 1981. Regulation of ferric iron transport in *Escherichia coli* K12: isolation of a constitutive mutant. Mol. Gen. Genet. 182, 288-292.

Henderson I et al., 2004. Type V protein secretion pathway: the autotransporter story. Microbiology and Molecular Biology Reviews, 68(4), 692-744

Hiroshi, N., 1996. Outer membrane. in: Neidhardt, F. C., Umbarger, H. E. (Eds.), *Escherichia Coli* and *Salmonella Typhimurium*: Cellular and Molecular Biology. ASM Press, Washington, pp. 29-47.

Homola, J., 2006. Surface Plasmon resonance based sensors. Springer, Berlin.

Huang, I. Y., Lee, M. C., 2008. Development of a FPW allergy biosensor for human IgE detection by MEMS and cystamine-based SAM technologies. Sen. Actuators B Chem. 132, 340-348.

Jeon, B. J., Pyun, J. C., 2008. Reconstruction of the immunoaffinity layer of SPR biosensor by using proteolytic enzyme. BioChip J. 2, 269-273.

Jose, J., Jahnig, F., Meyer, T. F., 1995. Common structural features of IgA1 protease-like outer membrane protein autotransporters. Mol. Microbiol. 18, 378-380.

Jose, J., 2006. Autodisplay: efficient bacterial surface display of recombinant proteins. Appl. Microbiol. Biotechnol. 69, 607-614.

Jose, J., Meyer, T. F., 2007. The autodisplay story, from discovery to biotechnical and biomedical applications. Microbiol. Mol. Biol. Rev. 71, 600-619.

Josephy, P. D., Eling, T., Mason, R. P., 1982. The horseradish peroxidase-catalyzed oxidation of 3,5,3′,5′-tetramethylbenzidine. Free radical and charge-transfer complex intermediates. J. Biol. Chem. 257, 3669-3675.

Kanno, S., Yanagida, Y., Haruyama, T., Kobatake, E., Aizawa, M., 2000. Assembling of engineered IgG-binding protein on gold surface for highly oriented antibody immobilization. J. Biotechnol. 76, 207-214.

Kurosawa, S., Nakamura, M., Park, J. W., Aizawa, H., Yamada, K., Hirata, M., 2004. Evaluation of a high-affinity QCM immunosensor using antibody fragmentation and 2-methacryloyloxyethyl phosphorylcholine (MPC) polymer. Biosens. Bioelectron. 20, 1134-1139.

Liddell, E., 2001. Antibodies. in: Wild, D. (Ed.), The immunoassay handbook. Nature publishing group, London, pp. 118-139.

Lu, B., Smyth, M. R., Kennedy, R. O., 1996. Oriented immobilization of antibodies and its applications in immunoassays and immunosensors. Analyst 121, 29-32.

Luppa, P. B., Sokoll, L. J., Chan, D. W., 2001. Immunosensors-principles and application to clinical chemistry. Clin. Chim. Acta 314, 1-26.

Owaku, K., Goto, M., Ikariyama, Y., Aizawa, M., 1995. Protein A Langmuir-Blodgett film for antibody immobilization and its use in optical immunosensing. Anal. Chem. 67, 1613-1616.

Park, I. S., Kim, W. Y., Kim, N., 2000. Operational characteristics of an antibody-immobilized QCM system detecting *Salmonella* spp. Biosens. Bioelectron. 15, 167-172.

Schultheiss, E., Paar, C., Schwab, H., Jose, J., 2002. Functional esterase surface display by the autotransporter pathway in *Escherichia coli*. J. Mol. Catal., B Enzym. 18, 89-97.

Silin, V., Weetall, H., Vanderah, D. J., 1997. SPR studies of the non-specific adsorption kinetics of human IgG and BSA on gold surfaces modified by self-assembled monolayers (SAMs). J. Colloid. Interf. Sci. 186, 94-103.

Stubbs, D. D., Hunt, W. D., Lee, S. H., Doyle, D. F., 2002. Gas phase activity of anti-FITC antibodies immobilized on a surface acoustic wave resonator device. Biosens. Bioelectron. 17, 471-477.

Wessa, T., Rapp, M., Ache, H. J., 1999. New immobilization method for SAW-biosensors: covalent attachment of antibodies via CNBr. Biosens. Bioelectron. 14, 93-98.

Mirsky V M, Riepl M, Wolfbeis O S. Capacitive monitoring of protein immobilization and antigen-antibody reactions on monomolecular alkylthiol films on gold electrodes. Biosens. Bioelectron. 1997; 68: 1-6.

Berggren C, Bjarnason B, Johansson G. An immunological Interleukine-6 capacitive biosensor using perturbation with a potentiostatic step. Biosens. Bioelectron. 1998; 13: 1061-68.

Berggren C, Stalhandske P, Brundell J, Johansson G. A Feasibility study of a capacitive biosensor for direct detection of DNA hybridization. Electroanalysis 1999; 11: 156-60.

Berggren C, Bjarnason B, Johansson G. Capacitive biosensors. Electroanalysis 2001; 13: 173-80.

Dijksma M, Kamp B, Hoogvliet J C, van Bennekom W P. Development of an electrochemical immunosensor for direct detection of interferon-γ at the attomolar level. Anal. Chem. 2001; 73: 901-7.

Bard A J, Faulkner L R. Electrochemical Method Fundamentals and Applications, 2nd ed. New York: John Wiley & sons Ltd; 2001

Bart M, Stigter E C A, Stapert H R, de Jong G J, van Bennekom W P. On the response of a label-free interferon-r immunosensor utilizing electrochemical impedance spectroscopy. Biosens. Bioelectron. 2005; 21: 49-59.

Hu S Q, Xie Z M, Lei C X, Shen G L, Yu R Q. The integration of gold nanoparticles with semi-conductive oligomer layer for development of capacitive immunosensor. Sens. Actuators, B 2005; 106: 641-7.

Li J, Wu Z, Wang H, Shen G, Yu R. A reusable capacitive immunosensor with a novel immobilization procedure based on 1,6-hexanedithiol and nano-Au self-assembled layers. Sens. Actuators, B 2005; 110: 327-34.

Wu Z S, Li J S, Deng T, Luo M H, Shen G L, Yu R Q. A sensitive immunoassay based on electropolymerized films by capacitance measurements for direct detection of immunospecies. Anal. Biochem. 2005; 337: 308-15.

Fu Y, Xie Q, Jia X, Xu X, Meng W, Yao S. Electrosynthesized poly(1,6-hexanedithiol) as a new immobilization matrix for Au-nanoparticles-enhanced piezoelectric immunosensing. J. Electroanal. Chem. 2007; 603: 96-106.

Hu S Q, Wu Z Y, Zhou Y M, Cao Z X, Shen G L, Yu R Q. Capacitive immunosensor for transferrin based on an o-aminobenzenthiol oligomer layer. Anal. Chim. Acta 2002; 458: 297-304.

Li J, Wang H, Deng T, Wu Z, Shen G, Yu R. A plasma-polymerized film for capacitance immunosensing. Biosens. Bioelectron. 2004; 20: 841-7.

Yang L, Wei W, Gao X, Xia J, Tao H. A new antibody immobilization strategy based on electrodeposition of nanometer-sized hydroxyapatite for label-free capacitive immunosensor. Talanta 2005; 68: 40-6.

Liao H, Zheng Z, Li H, Nie L, Yao S. Preparation of the molecularly imprinted polymers-based capacitive sensor specific for tegafur and its characterization by electrochemical impedance and piezoelectric quartz crystal microbalance. Electrochim. Acta 2004; 49: 4101-7.

Zheng Z, Nie L, Yao S. Electrodeposited sol-gel-imprinted sensing film for cytidine recognition on Au-electrode surface. Talanta 2006; 69: 435-42.

Nader R, Paul M R. Inflammatory markers and coronary heart disease. Curr. Opin. Lipidol. 2002; 13: 383-9.

Hamann C H, Hamnett A, Vielstich W. Electrochemistry. New York: Wiley-VCH; 1998, pp. 244-7.

Benz I, Schmidt M A. Isolation and serologic characterization of AIDA-1, the adhesin mediating the diffuse adherence phenotype of diarrhea-associated *Escherichia coli* strain 2787. Infect Immun 1992; 60:13-8.

Maurer J, Jose J, Meyer T F. Autodisplay: one-component system for efficient surface display and release of soluble recombinant proteins from *Escherichia coli*. J Bacteriol 1997; 179:794-804.

Maurer J, Jose J, Meyer T F. Characterization of the essential transport function of the AIDA-I autotransporter and evidence supporting structural predictions. J Bacteriol, 1999; 181:7014-20.

Jose J, Betscheider D, Zangen D. Bacterial surface display library screening by target enzyme labeling: Identification of new human cathepsin G inhibitors. Anal Biochem 2005; 46:258-67.

Jose J, Bernhardt R, Hannemann F. Functional display of active bovine adrenodoxin on the surface of *E.coli* by chemical incorporation of the [2Fe±2S] cluster. Chembiochem 2001; 2:695-701.

Green N M. Avidin. Adv Protein Chem 1975; 29:85-133.

Green N M. Avidin and streptavidin. Methods Enzymol 1990; 184:51-67.

Wilchek M, Bayer E A. The avidin-biotin complex in bioanalytical applications. Anal Biochem 1988; 171:1-32.

Bayer E A, Wilchek M. Application of avidin-biotin technology to affinity-based separations. J Chromatogr 1990; 510:3-11.

Chen L, Schechter B, Arnon R, Wilchek M. Tissue selective affinity targeting using avidin-biotin system. Drug Dev Res 2000; 50:258-71.

Qureshi M H, Wong S L. Design, production, and characterization of a monomeric streptavidin and its application for affinity purification of biotinylated proteins. Protein Expr Purif 2002; 25:409-15

Howarth M, Chinnapen D J F, Gerrow K, Dorrestein P C, Grandy M R, Kelleher N L, Husseini A E I, Ting A T. A monovalent streptavidin with a single femtomolar biotin binding site. Nat Methods 2006; 3:267-73.

Jose J, Bernhardt R, Hannemann F. Cellular surface display of dimeric Adx and whole cell P450-mediated steroid synthesis on *E.coli*. J Biotechnol 2002; 95:257-68.

Koebnik R, Locher K P, van Gelder P. Structure and function of bacterial outer membrane proteins: barrels in a nutshell. Mol Microbiol 2000; 37:239-53.

Kubitschek H E. Cell volume increase in *Escherichia coli* after shifts to richer media. J Bacteriol 1990; 172:94-101.

Petzold A. et al., Neuroscience Letters, 2003, 336:167-170.

Steiner J. et al., J Neurol Neurosurg Psychiatry, 2006 77:1284-1287.

---

The invention claimed is:

1. A carrier comprising a layer bound to the surface of the carrier, wherein said layer comprises a recombinant fusion polypeptide oriented away from the carrier, wherein the layer is formed from outer membrane particles isolated from a gram negative bacterial host cell which expressed the recombinant polypeptide on its surface, wherein the recombinant polypeptide is anchored to the outer membrane particles, and, wherein the outer membrane particles further comprise liposaccharide (LPS), wherein said carrier has a hydrophobic surface and said outer membrane particles have a hydrophilic surface and a hydrophobic core, wherein hydrophobic interactions between the core of the outer membrane particle and the surface of the carrier lead to the formation of said layer, and wherein said outer membrane particles have a diameter of 1-1000 nm.

2. The carrier according to claim 1, wherein the surface is selected from metal surfaces, polymeric surfaces and glass surfaces.

3. The carrier according to claim 1, wherein the recombinant polypeptide is selected from antibodies, fragments and variants thereof, protein A, fragments and variants thereof, streptavidin, fragments and variants thereof, avidin, fragments and variants thereof, M proteins from Streptococci, fragments and variants thereof, protein G, fragments and variants thereof.

4. The carrier according to claim 1, wherein the recombinant polypeptide is selected from receptors, ligands, and enzymes.

5. The carrier according to claim 1, further comprising a binding molecule specifically bound to the recombinant polypeptide.

6. The carrier according to claim 1, which is a biosensor.

7. A method for detecting an analyte in a sample, comprising contacting a carrier according to claim 1 with a sample and determining the desired analyte.

8. The carrier according to claim 1, wherein said recombinant polypeptide and membrane components are bound to the carrier by a method comprising expressing a nucleic acid fusion in a host cell, wherein an expression product comprising a recombinant polypeptide is anchored on the surface of the host cell, preparing membrane particles from the host cell, and contacting the membrane particles with the surface of a carrier so that the membrane particles form a layer bound to the surface of said carrier, wherein the recombinant polypeptide is oriented away from the surface of the carrier.

9. The carrier according to claim 6, wherein said biosensor is a surface plasmom resonance (SPR) biosensor or a capacitive biosensor.

10. The carrier according to claim 1, wherein the surface of the carrier is a hydrophobic surface.

11. The carrier according to claim 10, wherein the outer membrane particles comprise a hydrophilic surface and a hydrophobic core, wherein the layer is formed from the outer membrane particles when hydrophobic interactions induce contact between the hydrophobic surface of the carrier and the core portion of the membrane particles.

12. The carrier according to claim 8, wherein said nucleic acid fusion comprises (i) a portion encoding a signal peptide (ii) a portion encoding the recombinant polypeptide to be displayed, (iii) a portion encoding a transmembrane linker, and (iv) a portion encoding the transporter domain of an autotransporter.

13. The carrier according to claim 1, wherein said outer membrane particles have a diameter of 50-500 nm.

* * * * *